US011377682B2

(12) United States Patent
Wu et al.

(10) Patent No.: US 11,377,682 B2
(45) Date of Patent: Jul. 5, 2022

(54) COMPOSITIONS AND METHODS FOR NUCLEIC ACID AMPLIFICATION

(71) Applicant: Ampliwise Inc., Santa Clara, CA (US)

(72) Inventors: Kai Wu, Mountain View, CA (US); Mindy Su, Cupertino, CA (US); Xing Su, Cupertino, CA (US)

(73) Assignee: Ampliwise Inc., Santa Clara, CA (US)

( * ) Notice: Subject to any disclaimer, the term of this patent is extended or adjusted under 35 U.S.C. 154(b) by 53 days.

(21) Appl. No.: 15/597,310

(22) Filed: May 17, 2017

(65) Prior Publication Data

US 2017/0327877 A1  Nov. 16, 2017

Related U.S. Application Data

(63) Continuation of application No. PCT/US2015/061255, filed on Nov. 18, 2015.

(60) Provisional application No. 62/082,534, filed on Nov. 20, 2014, provisional application No. 62/082,538, filed on Nov. 20, 2014, provisional application No. 62/082,541, filed on Nov. 20, 2014.

(51) Int. Cl.
*G01N 33/00* (2006.01)
*C12Q 1/6853* (2018.01)
*C12P 19/34* (2006.01)
*C12Q 1/6827* (2018.01)
*C12Q 1/686* (2018.01)
*C07H 21/04* (2006.01)

(52) U.S. Cl.
CPC ............ *C12Q 1/6853* (2013.01); *C12P 19/34* (2013.01); *C12Q 1/686* (2013.01); *C12Q 1/6827* (2013.01)

(58) Field of Classification Search
None
See application file for complete search history.

(56) References Cited

U.S. PATENT DOCUMENTS

| | | | |
|---|---|---|---|
| 6,090,592 A | 7/2000 | Adams et al. | |
| 8,304,183 B2 | 11/2012 | Sooknanan | |
| 2002/0081583 A1 | 6/2002 | Abe et al. | |
| 2002/0137058 A1 | 9/2002 | Mirkin et al. | |
| 2003/0170711 A1 | 9/2003 | Brown et al. | |
| 2007/0148642 A1* | 6/2007 | Kondo | C12Q 1/6883 435/6.11 |
| 2007/0154895 A1* | 7/2007 | Spaid et al. | G01N 33/54366 435/6.19 |
| 2009/0325169 A1 | 12/2009 | Walder et al. | |
| 2010/0105575 A1* | 4/2010 | Wang | C12Q 1/6827 506/12 |
| 2011/0256637 A1* | 10/2011 | Soh | C12Q 1/6827 436/501 |
| 2013/0295562 A1* | 11/2013 | Ma et al. | G01N 33/57426 435/6.11 |
| 2013/0310269 A1 | 11/2013 | So | |
| 2014/0162885 A1 | 6/2014 | Berka et al. | |
| 2014/0315209 A1* | 10/2014 | Lippe et al. | C12N 9/86 435/6.11 |
| 2020/0071751 A1* | 3/2020 | Daugharthy et al. | C12Q 1/6806 |

FOREIGN PATENT DOCUMENTS

| | | |
|---|---|---|
| WO | WO-2016081549 A1 | 5/2016 |
| WO | WO-2016081551 A1 | 5/2016 |
| WO | WO-2016081585 A1 | 5/2016 |

OTHER PUBLICATIONS

"Viruses", Wikipedia.com, accessed Nov. 24, 2012. (Year: 2012).*
"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," (Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
Sharon Begley, "Psst, the human genome was never completely sequenced", STS News, Jun. 20, 2017. (Year: 2017).*
Forster et al., "A human gut bacterial genome and culture collection for improved metagenomics analyses", Nature Biotechnology, vol. 37, Feb. 2019, pp. 186-192. (Year: 2019).*
"List of sequenced bacterial genomes", Wikipedia.com; accessed Jan. 24, 2014. (Year: 2014).*
Co-pending U.S. Appl. No. 15/597,305, filed May 17, 2017.
Co-pending U.S. Appl. No. 15/597,313, filed May 17, 2017.
International search report and written opinion dated Mar. 21, 2016 for PCT Application No. PCT/US15/61252.
International search report and written opinion dated Apr. 19, 2016 for PCT Application No. PCT/US15/61312.
International search report and written opinion dated Apr. 21, 2016 for PCT Application No. PCT/US15/61255.
Lin, et al. 3'-5' Exonucleolytic Activity of DNA Polymerases: Structural Features That Allow Kinetic Discrimination between Ribo- and Deoxyribonucleotide Residues. Biochemistry 40:8749-8755, 2001.

* cited by examiner

*Primary Examiner* — Bradley L. Sisson
(74) *Attorney, Agent, or Firm* — Dave Law Group LLC; Raj S. Dave

(57) ABSTRACT

The disclosure provides compositions and methods for amplifying and/or analyzing nucleic acids.

13 Claims, 29 Drawing Sheets

Specification includes a Sequence Listing.

5' ACGTTCGAGGTGGGTGACC 3' PM
5' ACGTTCGAGCTGGGTGACC 3' rM
5' ACGTTCGA*C*TGGGTGACC 3' r3M
5' ACGTTCGAGC*G*GGTGACC 3' 5Mr

|  | SS 2x EDTA | SS | DS, PM 2xEDTA | DS, PM 1x EDTA | DS PM | DS rM | DS r3M | DS 5rM |
|---|---|---|---|---|---|---|---|---|
| EDTA | 2x | 0 | 2x | 1x | 0 | 0 | 0 | 0 |
| Mosaic Probe | + | + | + | + | + | + | + | + |
| PM |  |  | + | + | + |  |  |  |
| rM |  |  |  |  |  | + |  |  |
| r3M |  |  |  |  |  |  | + |  |
| 5Mr |  |  |  |  |  |  |  | + |

*FIG. 2A*

| Sample ID | 1 | 2 | 3 | 4 | 5 | 6 | 7 | 8 |
|---|---|---|---|---|---|---|---|---|
| pH 9 | + | + | + | + | | | | |
| pH 7 | | | | | + | + | + | + |
| $MgCl_2$ | + | + | | | + | + | | |
| PM | 0.25x | 1x | 0.25x | 1x | 0.25x | 1x | 0.25x | 1x |

| Sample | 1 | 2 | 3 | 4 | 5 | 6 | 7 | 8 |
|---|---|---|---|---|---|---|---|---|
| Mosaic Probe | 1x | 1x | 1x | 1x | 1x | 1x | 1x | 1x |
| PM | 0 | 0.25x | 0.5x | 1x | | | | |
| rM | | | | | 0.5x | 1x | | |
| r3M | | | | | | | 1x | |
| 5Mr | | | | | | | | 1x |

*FIG. 4A*

Null Probe  5'-CCTGTTGTCCTCCAATTTGTCCTGGT-Phos 3'

5'-ACCAGGACAAATTGGAGGACAACAGG-Phos 3'  Target Nucleic Acid Molecule

FLUORESCENT STRAND  5'-AACCTGTTGTCCTCCAATTTGT-FAM-3'  ←801

QUENCH STRAND 1  5'-/5IABKFQ/ACAAATTGGAGGACAACAGGT-3'  ←803

QUENCH STRAND 2  5'-/5IABKFQ/ACAAATTGGAGGACAACAGGTddC-3'   ←804

*FIG. 8A*

| Priming Oligonucleotide | 1 | 2 | 3 |
|---|---|---|---|
| 1000 | + |   | + |
| 1050 |   | + | + |

*FIG. 11A*

```
                                                              G-forward
5'-                                                    ─────────────────→
CATGTGGACCCCGTGGTTGTGTTTGACTTCGCTAGCTTATACCCCAGCATTATCCAGGCCCATAACCTCTGTTTCACC
GGGTGACCAAAAGTTATTTTTTGTCCACGCCCATATTCGCGAAAGCCTGCTTGGCATCTTGCTGCG-3'
                                              ←─────────────────
                                                    A-reverse
```

*FIG. 14A*

```
                                          A-forward
                                     ─────────────────▶
ACCCTGGCGCTCGATGAAGTGGATCTGGCCGGGCTTCAACCATCCGTCNACTACTCGACGTTCGAGGTGGT
                                     ◀─────────────────
                                            G-reverse
```

*FIG. 14B*

| Detection of SNP A | |
|---|---|
| A-reverse | 5' GCAGCAAGATGCCAAGCAUU |
| A-forward | 5' GGCTTCAACCATCCGTCIUU |

| Detection of SNP G | |
|---|---|
| G-forward | 5' CCC ATA ACC TCT GTT TCA CC UU |
| G-reverse | 5' AC CTC GAA CGT CGA GTA GTUUU |

*FIG. 14C*

SEQUENCE LISTING

<160> NUMBER OF SEQ ID NOS: 28

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcagtcccaa atctccagtc actca                                           25

<210> SEQ ID NO 2
<211> LENGTH: 24
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 2
gggcaacata ccttgatagt ccag                                          24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 3
tcccaaatct ccagtcactc uu                                            22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 4
caacatacct tgatagtcca guu                                           23

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
tggtcaccac ctcgaacgt                                                19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acgttcgagc cgggtgacc                                                19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acgttcgaac tgggtgacc                                                19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acgttcgagc tgggtgacc                                                19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acgttcgagg tgggtgacc                                                19

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 10
cctgttgtcc tccaatttgt cctggt                                        26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
cctgttgtcc tccaatttgt cctggt                                        26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
accaggacaa attggaggac aacagg                                        26

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 13
aacctgttgt cctccaattt gt                                             22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
acaaattgga ggacaacagg t                                              21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
acaaattgga ggacaacagg tc                                             22

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tttggtgttt at                                                        12

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
gtgctataaa caccagcctc cca                                            23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgggaggctg gtgtttatag cac                                            23

<210> SEQ ID NO 19
<211> LENGTH: 13
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 19
caccagcctc cca                                                        13

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
cagaatatac atcctgtcac aattgtttt                                       29

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
caattgtgac ttt                                                        13

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cagaatatac atcctgtcac                                                 20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgggatattc cttaatcctg t                                               21

<210> SEQ ID NO 24
<211> LENGTH: 215
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (127)..(127)
<223> OTHER INFORMATION: a, c, t, g, unknown or other

<400> SEQUENCE: 24
catgtggacc ccgtggttgt gtttgacttc gctagcttat accccagcat tatccaggcc     60
cataacctct gtttcaccac cctggcgctc gatgaagtgg atctggccgg gcttcaacca    120

```
tccgtcnact actcgacgtt cgaggtggtg ggtgaccaaa agttatttt tgtccacgcc      180 catattcgcg aaagcctgct tggcatcttg ctgcg                                215
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 25

```
gcagcaagat gccaagcauu                                                  20
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (18)..(18)
<223> OTHER INFORMATION: Inosine

<400> SEQUENCE: 26

```
ggcttcaacc atccgtcnuu                                                  20
```

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 27

```
cccataacct ctgtttcacc uu                                               22
```

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 28

```
acctcgaacg tcgagtagtu uu                                               22
```

COMPOSITIONS AND METHODS FOR NUCLEIC ACID AMPLIFICATION

CROSS-REFERENCE

This application is a continuation of PCT International Application No. PCT/US2015/061255, filed Nov. 18, 2015, which claims priority to U.S. Provisional Patent Application No. 62/082,534 filed on Nov. 20, 2014, U.S. Provisional Patent Application No. 62/082,538 filed on Nov. 20, 2014 and U.S. Provisional Patent Application No. 62/082,541 filed on Nov. 20, 2014, which applications are herein incorporated by reference in their entireties for all purposes.

SEQUENCE LISTING

The instant application contains a Sequence Listing which has been submitted electronically in ASCII format and is hereby incorporated by reference in its entirety. Said ASCII copy, created on Jul. 7, 2017, is named 46846702301SL.txt and is 8,071 bytes in size.

BACKGROUND

Nucleic acid amplification methods permit amplification of nucleic acid molecules in a sample, such as a biological sample. A nucleic acid molecule can be amplified, via, for example, thermal cycling based approaches (e.g., polymerase chain reaction (PCR)) or via isothermal approaches. Nucleic acid amplification may also be useful in preparing a nucleic acid molecule for subsequent analysis in numerous applications related to nucleic acid analysis such as, for example in detecting target nucleic acid sequences, detecting rare nucleic acid molecules/sequences in a sample and/or preparing a nucleic acid molecule for a sequencing reaction. Thus, due to the applicability of nucleic acid amplification to a wide range of applications, there exists a need for compositions and methods useful for amplifying nucleic acid molecules and/or for analyzing amplified nucleic acid molecules that are generated from nucleic acid amplification.

SUMMARY

The disclosure provides probes, devices, priming oligonucleotides, compositions and methods for the amplification and analysis of nucleic acids.

An aspect of the disclosure provides a probe having a nucleic acid sequence that is complementary to a single-stranded target nucleic acid molecule. The nucleic acid sequence can have (i) at least one cleavable moiety, (ii) a detectable moiety, and (iii) a quencher. The quencher can quench the detectable moiety when the probe is not hybridized to the single-stranded target nucleic acid molecule.

In some embodiments, the probe may be single-stranded. In some embodiments, the probe may not capable of intramolecular hybridization. In some embodiments the probe may comprise a plurality of cleavable moieties. In some embodiments, the detectable moiety may be a fluorophore. In some embodiments, the detectable moiety may be adapted to provide a detectable signal upon hybridization of the probe to the single-stranded target nucleic acid molecule.

In some embodiments, the at least one cleavable moiety may be a ribose moiety. Additionally, a solution may contain the probe and may, for example comprise an alkaline buffer.

In some embodiments, the probe may comprise a nucleotide sequence A and a nucleotide sequence B flanking the at least one cleavable moiety. The nucleotide sequence A and nucleotide sequence B can each be complementary to a portion of the single-stranded target nucleic acid molecule. In some embodiments, the cleavable moiety may be cleavable upon hybridization of the probe to the single-stranded target nucleic acid molecule. In some embodiments, the cleavable moiety may be cleavable at alkaline conditions and/or cleavable without the aid of an enzyme.

In some embodiments, the probe may be adapted to hybridize to the single-stranded target nucleic acid molecule such that the at least one cleavable moiety is situated at a single nucleotide polymorphism (SNP) site of the single-stranded target nucleic acid molecule. In some embodiments, the at least one cleavable moiety is complementary with respect to a nucleotide at the SNP site.

Additionally, the probe may be immobilized on an array that comprises a substrate, such as, for example, a solid substrate. The solid substrate may comprise a material selected from the group consisting of a metal, a semi-metal, a glass, a polymer, a metal oxide, a silicon oxide and a silicon nitride. In some embodiments, the probe may be immobilized in a well of the array.

An additional aspect of the disclosure provides a method for detecting a single nucleotide polymorphism (SNP). The method can comprise providing a reaction mixture comprising a single-stranded target nucleic acid molecule and probe. The probe can have a nucleic acid sequence with (i) at least one cleavable moiety, (ii) a detectable moiety, and (iii) a quencher. Moreover, the probe can be complementary to the single-stranded target nucleic acid molecule and the quencher can quench the detectable moiety when the probe is not hybridized to the single-stranded target nucleic acid molecule. The method can further comprise hybridizing the probe to the single-stranded target nucleic acid molecule, where upon hybridization, the cleavable moiety is disposed adjacent to a nucleotide in a single nucleotide polymorphism (SNP) site of the single-stranded target nucleic acid molecule. The method can further comprise detecting a signal from the probe that is indicative of the presence of the nucleotide in the SNP site.

In some embodiments, providing the reaction mixture and hybridizing the probe to the single-stranded target nucleic acid molecule such that the cleavable moiety is disposed adjacent to a nucleotide in a SNP site of the single-stranded target nucleic acid molecule may be performed without the aid of an enzyme and/or without cycling a temperature of the reaction mixture. In some embodiments, the method further comprises maintaining a pH of the reaction mixture at above 7 such as, for example, from 8 to 11.

In some embodiments, the single-stranded target nucleic acid molecule may not contain a detectable moiety. In some embodiments, the cleavable moiety can be cleaved upon hybridization of the probe to the single-stranded target nucleic acid molecule. In some embodiments, the detectable moiety can be adapted to provide the signal upon hybridization of the probe to the single-stranded target nucleic acid molecule. The signal may be, for example, an optical signal, electrostatic signal, or electrochemical signal.

In some embodiments, the probe comprises a plurality of cleavable moieties. In some embodiments, the probe can comprise a nucleotide sequence A and a nucleotide sequence B flanking the at least one cleavable moiety. The nucleotide sequence A and nucleotide sequence B can each be complementary to a portion of the single-stranded target nucleic acid molecule. In some embodiments, the cleavable moiety may be complementary with respect to the nucleotide in the SNP site. In some embodiments, the probe may be immobilized on a substrate of an array. In some embodiments, the probe may be immobilized in a well of the array.

An additional aspect of the disclosure provides a method for detecting a single nucleotide polymorphism (SNP). The method can comprise providing a first reaction mixture comprising (i) a first strand of a target nucleic acid molecule and (ii) a first primer having a purine derivative at a nucleotide site of the first primer that corresponds to a nucleotide site of the first strand that is suspected of comprising a first nucleotide site of a single nucleotide polymorphism (SNP). The purine derivative can preferentially hybridize with a pyrimidine base of the first strand over other types of bases of the first strand. The method can further comprise providing a second reaction mixture comprising (i) a complementary strand of the first strand of the target nucleic acid molecule and (ii) a second primer having a pyrimidine derivative at a nucleotide site of the second primer that corresponds to a nucleotide site of the complementary strand that is suspected of comprising a second nucleotide site of the SNP. The pyrimidine derivative can preferentially hybridize with a purine base of the complementary strand over other types of bases of the complementary strand. The method can further comprise subjecting the first and second reaction mixtures to conditions such that the first primer is extendable upon hybridization to the first strand to yield a first nucleic acid product and the second primer is extendable upon hybridization to the complementary strand to yield a second nucleic acid product and determining relative quantities of the first and second nucleic acid products.

In some embodiments, the pyrimidine base of the first strand may be a cytosine base. In some embodiments, the purine base of the complementary strand may be an adenine base. In some embodiments, the purine derivative may not be a guanine. In some embodiments, the purine derivative can be hypoxanthine or a derivative thereof. In some embodiments, the pyrimidine derivative may not be thymine. In some embodiments, the pyrimidine derivative may be uracil or a derivative thereof. In some embodiments, the purine derivative may be replaceable by an adenine base with the aid of an enzyme having 3' to 5' exonuclease activity. In some embodiments, the pyrimidine derivative may be replaceable by a cytosine base with the aid of an enzyme having 3' to 5' exonuclease activity.

In some embodiments, the first and second reaction mixtures can be in separate containers. In some embodiments, each of the first and second reaction mixtures can comprise a detectable moiety such as, for example, an optically detectable moiety (e.g., SYBR green, EvaGeen, BEBO, BOXTO, an intercalating dye).

In some embodiments, determining relative quantities of the first and second nucleic acid products may be completed with the aid of a melting curve analysis. In some embodiments, determining relative quantities of the first and second nucleic acid products may be completed with the aid of a change in cycle threshold ($\Delta C_t$). In some embodiments, determining relative quantities of the first and second nucleic acid products may be completed with the aid of gel electrophoresis. In some embodiments, determining relative quantities of the first and second nucleic acid products may be completed with the aid of a computer processor that is programmed to compare the relative quantities of the first and second nucleic acid products. In some embodiments, a greater quantity of the first nucleic acid product in relation to the second nucleic acid product can be indicative of the presence of a purine base at the first nucleotide site of the SNP. In some embodiments, a greater quantity of the second nucleic acid product in relation to the first nucleic acid product can be indicative of the presence of a pyrimidine base at the second nucleotide site of the SNP.

An additional aspect of the disclosure provides an inactivatable priming oligonucleotide. The inactivatable priming oligonucleotide can comprise a priming region having (i) a nucleic acid sequence A that can be hybridizable to a single-stranded target nucleic acid molecule, where a 3' end of the nucleic acid sequence A is adapted to be extended in a primer extension reaction to form a complement nucleic acid strand of the single-stranded target nucleic acid molecule, and (ii) at least one cleavable moiety. The inactivatable priming oligonucleotide can further comprise a nucleic acid sequence B adjacent to the priming region that can exhibit sequence complementarity to the priming region.

In some embodiments, the 3' end of the nucleic acid sequence A may only be extendable at a temperature equal to or above a melting temperature of the nucleic acid sequence B. In some embodiments, the priming region may include, from 3' to 5', the nucleic acid sequence A, the cleavable moiety and a nucleic acid sequence A' that can be complementary to the single-stranded target nucleic acid molecule. In some embodiments, the nucleic acid sequence B may not complementary to the single-stranded target nucleic acid molecule. In some embodiments, the nucleic acid sequence B can be at least partially complementary to a complement of the single-stranded target nucleic acid molecule. In some embodiments, the nucleic acid sequence B can comprise a spacer that is not complementary to the priming region and/or the single-stranded target nucleic acid molecule. In some embodiments, the spacer cannot be copied by a polymerase. In some embodiments, the spacer may be a sequence of one or more nucleotides.

In some embodiments, the priming region can have a first melting temperature and the nucleic acid sequence B can have a second melting temperature that is less than the first melting temperature. In some embodiments, the first melting temperature may be at least about 50° C., 55° C., 60° C., 65° C., 70° C., 75° C. or 80° C. In some embodiments, the second melting temperature may be less than or equal to about 80° C., 75° C., 70° C., 65° C., 60° C., 55° C. or 50° C. In some embodiments, the second melting temperature may be less than first melting temperature by about 1° C. to 80° C., 5° C. to 30° C., or 10° C. to 20° C.

In some embodiments, the priming region may further comprise a nucleic acid sequence A'. In some embodiments, the nucleic acid sequence A can have a third melting temperature that is less than the first melting temperature upon cleavage of the cleavable moiety. In some embodiments, the third melting temperature may be less than the second melting temperature. In some embodiments, the third melting temperature may be less than or equal to about 80° C., 75° C., 70° C., 65° C., 60° C., 55° C. or 50° C.

In some embodiments, the at least one cleavable moiety may be a ribose. In some embodiments, the cleavable moiety may be photo cleavable. In some embodiments, the cleavable moiety may be enzymatically cleavable such as, for example, cleavable by an enzyme having endonuclease activity. In some embodiments, the cleavable moiety may be chemically cleavable. In some embodiments, the inactivatable priming oligonucleotide may comprise a plurality of cleavable moieties. In some embodiments, the inactivatable priming oligonucleotide may be a loop inactivatable priming oligonucleotide.

In some embodiments, the inactivatable priming oligonucleotide may be contained in a solution that may, in some embodiments, comprise an alkaline buffer.

An additional aspect of the disclosure provides an inactivatable priming oligonucleotide. The inactivatable priming oligonucleotide can comprise a priming region having (i) a nucleic acid sequence A that is hybridizable to a single-stranded target nucleic acid molecule, where the nucleic acid sequence A has a 3' end that is adapted to be extended in a primer extension reaction to form a complement nucleic acid strand of the single-stranded target nucleic acid molecule, and (ii) at least one cleavable moiety. The inactivatable priming oligonucleotide can also comprise a nucleic acid sequence B adjacent to the priming region, where the priming region has a first melting temperature and the nucleic acid sequence B has a second melting temperature that is less than the first melting temperature.

In some embodiments, the 3' end of the nucleic acid sequence A may only extendable at a temperature equal to or above the second melting temperature. In some embodiments, the priming region may include, 3' to 5', the nucleic acid sequence A, the cleavable moiety adjacent to the nucleic acid sequence A, and a nucleic acid sequence A' that is adjacent to the cleavable moiety. In some embodiments, the nucleic acid sequence A' may be complementary to the single-stranded target nucleic acid molecule. In some embodiments, the nucleic acid sequence B may not be complementary to the single-stranded target nucleic acid molecule. In some embodiments, the nucleic acid sequence B may be at least partially complementary to a complement of the single-stranded target nucleic acid molecule. In some embodiments, the nucleic acid sequence B may comprise a spacer that is not complementary to the priming region and/or the single-stranded target nucleic acid molecule. In some embodiments, the spacer may be a sequence of one or more nucleotides.

In some embodiments, the first melting temperature may be at least about 50° C., 55° C., 60° C., 65° C., 70° C., 75° C. or 80° C. In some embodiments, the second melting temperature may be less than or equal to about 80° C., 75° C., 70° C., 65° C., 60° C., 55° C. or 50° C. In some embodiments, the second melting temperature may be less than the first melting temperature by at least about 1° C. to 80° C., 5° C. to 30° C., or 10° C. to 20° C. In some embodiments, the nucleic acid sequence A can have a third melting temperature that is less than the first melting temperature upon cleavage of the cleavable moiety. In some embodiments, the third melting temperature may be less than the second melting temperature upon cleavage of the cleavable moiety. In some embodiments, the third melting temperature may be less than or equal to about 80° C., 75° C., 70° C., 65° C., 60° C., 55° C. or 50° C.

In some embodiments, the at least one cleavable moiety can be a ribose. In some embodiments, the cleavable moiety may be photo cleavable. In some embodiments, the cleavable moiety is enzymatically cleavable, such as, for example, cleavable by an enzyme having endonuclease activity. In some embodiments, the cleavable moiety may be chemically cleavable. In some embodiments, the inactivatable priming oligonucleotide comprises a plurality of cleavable moieties. In some embodiments, the inactivatable priming oligonucleotide can be a loop inactivatable priming oligonucleotide.

In some embodiments, the inactivatable priming oligonucleotide may be contained in a solution. Such a solution may comprise an alkaline buffer.

An additional aspect of the disclosure provides a method for inactivating an inactivatable priming oligonucleotide. The method can comprise providing a solution containing an inactivatable priming oligonucleotide comprising (a) a priming region having (i) a nucleic acid sequence A that is hybridizable to a single-stranded target nucleic acid molecule, where a 3' end of the nucleic acid sequence A is adapted to be extended in a primer extension reaction to form a complement nucleic acid strand of the single-stranded target nucleic acid molecule, and (ii) at least one cleavable moiety; and providing a nucleic acid sequence B adjacent to the priming region that exhibits sequence complementarity to the priming region. The method can further comprise cleaving the cleavable moiety, thereby inactivating the priming region of the inactivatable priming oligonucleotide.

In some embodiments, cleaving the cleavable moiety can be with the use of an enzyme such as, for example, with an endonuclease. In some embodiments, cleaving the cleavable moiety can be with the use of light. In some embodiments, cleaving the cleavable moiety can be via a pH of the solution that is greater than 7.

An additional aspect of the disclosure provides a method for inactivating an inactivatable priming oligonucleotide. The method can comprise providing a solution containing an inactivatable priming oligonucleotide comprising (a) a priming region having (i) a nucleic acid sequence A that is hybridizable to a single-stranded target nucleic acid molecule, where a 3' end of the nucleic acid sequence A is adapted to be extended in a primer extension reaction to form a complement nucleic acid strand of the single-stranded target nucleic acid molecule, and (ii) at least one cleavable moiety; and providing a nucleic acid sequence B adjacent to the priming region, where the priming region has a first melting temperature and the nucleic acid sequence B has a second melting temperature that is less than the first melting temperature. The method can further comprise cleaving the cleavable moiety, thereby inactivating the priming region of the inactivatable priming oligonucleotide.

In some embodiments, the priming region can comprise, from 3' to 5', the nucleic acid sequence A, the cleavable moiety adjacent to the nucleic acid sequence A, and a nucleic acid sequence A' that is adjacent to the cleavable moiety. In some embodiments, the method further comprises decreasing a temperature of the solution to equal to or below the second melting temperature. In some embodiments, the cleavable moiety can be cleaved at a temperature of the solution that is equal to or below the second melting temperature. In some embodiments, the method further comprises increasing the temperature of the solution to equal to or above the second melting temperature after cleaving the cleavable moiety.

In some embodiments, upon cleavage of the cleavable moiety, the nucleic acid sequence A may not stably hybridize with the single-stranded target nucleic acid molecule at a temperature equal to or above its melting temperature and/or the first melting temperature. In some embodiments, the first melting temperature may be at least about 50° C., 55° C., 60° C., 65° C., 70° C., 75° C. or 80° C. In some embodiments, the second melting temperature may be less than or equal to about 80° C., 75° C., 70° C., 65° C., 60° C., 55° C. or 50° C. In some embodiments, the second melting temperature may be less than the first melting temperature by about 1° C. to 80° C., 5° C. to 30° C., or 10° C. to 20° C. In some embodiments, the nucleic acid sequence A can have a third melting temperature that is less than the first melting temperature upon cleavage of the cleavable moiety. In some embodiments, the third melting temperature may be less than the second melting temperature. In some embodiments, the third melting temperature may be less than or equal to about 80° C., 75° C., 70° C., 65° C., 60° C., 55° C. or 50°

C. In some embodiments, the method further comprises increasing the temperature of the solution to equal to or above the third melting temperature.

In some embodiments, cleaving of the cleavable moiety may be with the use of an enzyme. In some embodiments, cleaving of the cleavable moiety may be with the use of light. In some embodiments, the cleaving of the cleavable moiety is via a pH of the solution that is greater than 7.

An additional aspect of the disclosure provides an activatable priming oligonucleotide. The activatable priming oligonucleotide can comprise a priming region having (i) a nucleic acid sequence A that is hybridizable to a single-stranded target nucleic acid molecule and (ii) at least one cleavable moiety, where the nucleic acid sequence A has a 3' end that is adapted to be extended in a primer extension reaction to form a complement nucleic acid strand of the single-stranded target nucleic acid molecule only upon cleavage of the cleavable moiety. The activatable priming oligonucleotide can also comprise a nucleic acid sequence B that is 3' to the priming region and exhibits sequence complementarity to the priming region.

In some embodiments, the priming region can include, from 5' to 3', the nucleic acid sequence A, the cleavable moiety, and a nucleic acid sequence A'. In some embodiments, the nucleic acid sequence A' may not be complementary to the single-stranded target nucleic acid molecule. In some embodiments, the nucleic acid sequence B may not be complementary to the single-stranded target nucleic acid molecule. In some embodiments, the nucleic acid sequence B may be at least partially complementary to a complement of the single-stranded target nucleic acid molecule. In some embodiments, the priming region can have a first melting temperature and the nucleic acid sequence B has a second melting temperature that is less than the first melting temperature. In some embodiments, the first melting temperature may be at least about 50° C., 55° C., 60° C., 65° C., 70° C., 75° C. or 80° C. In some embodiments, the second melting temperature may be less than or equal to about 80° C., 75° C., 70° C., 65° C., 60° C., 55° C. or 50° C. In some embodiments, the second melting temperature may be less than the first melting temperature by about 1° C. to 80° C., 5° C. to 30° C., or 10° C. to 20° C.

In some embodiments, the priming region can further comprise a nucleic acid sequence A'. In some embodiments, upon cleavage of the cleavable moiety, the nucleic acid sequence A can have a third melting temperature that is less than the first melting temperature. In some embodiments, the third melting temperature can be less than or greater than the second melting temperature. In some embodiments, the third melting temperature can be less than or equal to about 80° C., 75° C., 70° C., 65° C., 60° C., 55° C. or 50° C.

In some embodiments, the at least one cleavable moiety may be a ribose. In some embodiments, the cleavable moiety may be photo cleavable. In some embodiments, the cleavable moiety may be enzymatically cleavable such as, for example, cleavable by an endonuclease. In some embodiments, the cleavable moiety may be chemically cleavable. In some embodiments, the activatable priming oligonucleotide may comprise a plurality of cleavable moieties. In some embodiments, the activatable priming oligonucleotide may be a loop activatable priming oligonucleotide.

In some embodiments, the activatable priming oligonucleotide may be contained within a solution. Such a solution may comprise an alkaline buffer.

An additional aspect of the disclosure provides an activatable priming oligonucleotide. The activatable priming oligonucleotide can comprise a priming region having (i) a nucleic acid sequence A that is hybridizable to a single-stranded target nucleic acid molecule and (ii) at least one cleavable moiety, where the nucleic acid sequence A has a 3' end that is adapted to be extended in a primer extension reaction to form a complement nucleic acid strand of the single-stranded target nucleic acid molecule only upon cleavage of the cleavable moiety. The activatable priming oligonucleotide can further comprise a nucleic acid sequence B that is 3' to the priming region, where the priming region has a first melting temperature and the nucleic acid sequence B has a second melting temperature that is less than the first melting temperature.

In some embodiments, the priming region can include, from 5' to 3', the nucleic acid sequence A, the cleavable moiety, and a nucleic acid sequence A'. In some embodiments, the priming region nucleic acid sequence A' may not be complementary to the single-stranded target nucleic acid molecule. In some embodiments, the nucleic acid sequence B may not be complementary to the single-stranded target nucleic acid molecule. In some embodiments, the nucleic acid sequence B may be at least partially complementary to a complement of the single-stranded target nucleic acid molecule.

In some embodiments, the first melting temperature may be at least about 50° C., 55° C., 60° C., 65° C., 70° C., 75° C. or 80° C. In some embodiments, the second melting temperature may be less than or equal to about 80° C., 75° C., 70° C., 65° C., 60° C., 55° C. or 50° C. In some embodiments, the second melting temperature may be less than the first melting temperature by about 1° C. to 80° C., 5° C. to 30° C., or 10° C. to 20° C. In some embodiments, upon cleavage of the cleavable moiety, the nucleic acid sequence A can have a third melting temperature that is less than the first melting temperature. In some embodiments, the third melting temperature may be less than or greater than the second melting temperature. In some embodiments, the third melting temperature may be less than or equal to about 80° C., 75° C., 70° C., 65° C., 60° C., 55° C. or 50° C.

In some embodiments, the at least one cleavable moiety may be a ribose. In some embodiments, the cleavable moiety may be photo cleavable. In some embodiments, the cleavable moiety may be enzymatically cleavable such as, for example, cleavable by an endonuclease. In some embodiments, the cleavable moiety may be chemically cleavable. In some embodiments, the activatable priming oligonucleotide can comprise a plurality of cleavable moieties. In some embodiments, the activatable priming oligonucleotide can be a loop activatable priming oligonucleotide.

The activatable priming oligonucleotide can be contained in a solution. Such a solution may comprise an alkaline buffer.

An additional aspect of the disclosure provides a method for nucleic acid amplification. The method can comprise providing a solution containing an activatable priming oligonucleotide comprising a priming region having (i) a nucleic acid sequence A that is hybridizable to a single-stranded target nucleic acid molecule, (ii) at least one cleavable moiety and a nucleic acid sequence B that is 3' to the priming region and exhibits sequence complementarity to the priming region. The nucleic acid sequence A can have a 3' end that is adapted to be extended in a primer extension reaction to form a complement nucleic acid strand of the single-stranded target nucleic acid molecule only upon cleavage of the cleavable moiety. The method further comprises cleaving the cleavable moiety and performing the primer extension reaction using the nucleic acid sequence A to form the complement nucleic acid strand.

In some embodiments, cleaving the cleavable moiety can be with the use of an enzyme such as, for example, an endonuclease. In some embodiments, cleaving the cleavable moiety can be with the use of light. In some embodiments, cleaving the cleavable moiety can be via a pH of the solution that is greater than 7.

In some embodiments, the priming region can include, from 5' to 3', the nucleic acid sequence A, the cleavable moiety and a nucleic acid sequence A'. In some embodiments, the nucleic acid sequence A' may not be complementary to the single-stranded target nucleic acid molecule. In some embodiments, the nucleic acid sequence B may not be complementary to the single-stranded target nucleic acid molecule. In some embodiments, the nucleic acid sequence B may be at least partially complementary to a complement of the single-stranded target nucleic acid molecule.

In some embodiments, the priming region can have a first melting temperature and the nucleic acid sequence B can have a second melting temperature that is less than the first melting temperature. In some embodiments, the first melting temperature may be at least about 50° C., 55° C., 60° C., 65° C., 70° C., 75° C. or 80° C. In some embodiments, the second melting temperature can be less than or equal to about 80° C., 75° C., 70° C., 65° C., 60° C., 55° C. or 50° C. In some embodiments, the second melting temperature can be less than the first melting temperature by about 1° C. to 80° C., 5° C. to 30° C., or 10° C. to 20° C. In some embodiments, the priming region further comprises a nucleic acid sequence A'. In some embodiments, upon cleavage of the cleavable moiety, the nucleic acid sequence A can have a third melting temperature that is less than the first melting temperature. In some embodiments, the third melting temperature may be less than or greater than the second melting temperature. In some embodiments, the third melting temperature may be less than or equal to about 80° C., 75° C., 70° C., 65° C., 60° C., 55° C. or 50° C. In some embodiments, the method can further comprise, prior to performing the primer extension reaction, reducing the temperature of the solution to equal to or below the third melting temperature.

In some embodiments, the at least one cleavable moiety may be a ribose. In some embodiments, the activatable priming oligonucleotide may comprise a plurality of cleavable moieties. In some embodiments, the activatable priming oligonucleotide may be a loop activatable priming oligonucleotide.

An additional aspect of the disclosure provides a method for nucleic acid amplification. The method can comprise providing a solution containing an activatable priming oligonucleotide comprising a priming region having (i) a nucleic acid sequence A that is hybridizable to a single-stranded target nucleic acid molecule, (ii) at least one cleavable moiety and a nucleic acid sequence B that is 3' to the priming region. The priming region can have a first melting temperature and the nucleic acid sequence B can have a second melting temperature that is less than the first melting temperature. Moreover, the nucleic acid sequence A can have a 3' end that is adapted to be extended in a primer extension reaction to form a complement nucleic acid strand of the single-stranded target nucleic acid molecule only upon cleavage of the cleavable moiety. The method can further comprise cleaving the cleavable moiety and performing the primer extension reaction using the nucleic acid sequence A to form the complement nucleic acid strand.

In some embodiments, cleaving the cleavable moiety is with the use of an enzyme such as, for example, an endonuclease. In some embodiments, cleaving the cleavable moiety is with the use of light. In some embodiments, cleaving the cleavable moiety is via a pH of the solution that is greater than 7.

In some embodiments, the priming region can include, from 5' to 3', the nucleic acid sequence A, the cleavable moiety and a nucleic acid sequence A'. In some embodiments, the nucleic acid sequence A' may not be complementary to the single-stranded target nucleic acid molecule. In some embodiments, the nucleic acid sequence B may not be complementary to the single-stranded target nucleic acid molecule. In some embodiments, the nucleic acid sequence B may be at least partially complementary to a complement of the single-stranded target nucleic acid molecule.

In some embodiments, the first melting temperature may be at least about 50° C., 55° C., 60° C., 65° C., 70° C., 75° C. or 80° C. In some embodiments, the second melting temperature may be less than or equal to about 80° C., 75° C., 70° C., 65° C., 60° C., 55° C. or 50° C. In some embodiments, the second melting temperature may be less than the first melting temperature by about 1° C. to 80° C., 5° C. to 30° C., or 10° C. to 20° C. In some embodiments, upon cleavage of the cleavable moiety, the nucleic acid sequence A can have a third melting temperature that is less than the first melting temperature. In some embodiments, the third melting temperature can be less than or greater than the second melting temperature. In some embodiments, the third melting temperature may be less than or equal to about 80° C., 75° C., 70° C., 65° C., 60° C., 55° C. or 50° C. In some embodiments, prior to performing the primer extension reaction, the method further comprises reducing the temperature of the solution to equal to or below the third melting temperature.

In some embodiments, the at least one cleavable moiety may be a ribose. In some embodiments, the activatable priming oligonucleotide may comprise a plurality of cleavable moieties. In some embodiments, the activatable priming oligonucleotide may be a loop activatable priming oligonucleotide.

An additional aspect of the disclosure provides a reaction mixture that can comprise an activatable priming oligonucleotide and an inactivatable priming oligonucleotide. The activatable priming oligonucleotide can comprises a first priming region having a nucleic acid sequence A' that is hybridizable to a target nucleic acid molecule and at least one first cleavable moiety. The activatable priming oligonucleotide can become activated only upon cleavage of the first cleavable moiety, such that a 3' end of the nucleic acid sequence A' becomes extendable in a primer extension reaction to form a complement nucleic acid strand of the target nucleic acid molecule. Additionally, the inactivatable priming oligonucleotide can comprise a second priming region having a nucleic acid sequence A that is hybridizable to the target nucleic acid molecule and at least one second cleavable moiety. The inactivatable priming oligonucleotide can become inactivated upon cleavage of the second cleavable moiety, such that the nucleic sequence A does not form a stable complex with the target nucleic acid molecule to facilitate a primer extension reaction based on the target nucleic acid molecule sequence.

In some embodiments, the reaction mixture can further comprise the target nucleic acid molecule. In some embodiments, the activatable priming oligonucleotide can further comprise a nucleic acid sequence B' that is 3' to the priming region of the activatable priming oligonucleotide and exhibits sequence complementarity to the priming region of the activatable priming oligonucleotide. In some embodiments, the inactivatable priming oligonucleotide can further comprise a nucleic acid sequence B adjacent to the priming region of the inactivatable priming oligonucleotide that exhibits sequence complementarity to the priming region of the inactivatable priming oligonucleotide.

In some embodiments, the first cleavable moiety and/or the second cleavable moiety may be ribose. In some embodiments, the first cleavable moiety and/or second cleavable moiety are cleavable by an enzyme such as, for example, an endonuclease. In some embodiments, the first cleavable moiety and the second cleavable moiety may be cleavable by the same enzyme. In some embodiments, the inactivatable oligonucleotide may be inactivatable upon cleavage of the first cleavable moiety of the activatable oligonucleotide. In some embodiments, the activatable oligonucleotide may be activatable upon cleavage of the second cleavable moiety of the inactivatable oligonucleotide.

An additional aspect of the disclosure provides a method for nucleic acid amplification. The method can comprise providing a solution comprising a target nucleic acid molecule, an activatable priming oligonucleotide and an inactivatable priming oligonucleotide. The method further comprises performing successive nucleic acid amplification reactions. The successive nucleic acid amplification reactions can comprise at least a first phase followed by a second phase, where the first phase comprises amplification of a target nucleic acid molecule using at least a portion of the inactivatable priming oligonucleotide as a primer, where the second phase comprises amplification of the target nucleic acid molecule or a region thereof using at least a portion of the activatable priming oligonucleotide as another primer. The activatable priming oligonucleotide can be activated and the inactivatable priming oligonucleotide can be inactivated after the first phase. Moreover, the successive amplification reactions can yield amplified products of the target nucleic acid molecule.

In some embodiments, the activatable priming oligonucleotide and the inactivatable priming oligonucleotide can be activated and inactivated, respectively, by an enzyme having endonuclease activity. In some embodiments, the enzyme is thermal stable and/or activatable. In some embodiments, the enzyme is an RNase such as, for example, RNase HI, RNase HII or RNase HIII. In some embodiments, the successive nucleic acid amplification reactions can take place in a single reaction mixture. In some embodiments, the successive nucleic acid amplification reactions can take place in more than one reaction mixture. In some embodiments, the solution can further comprise at least one reverse primer.

In some embodiments, the activatable priming oligonucleotide can comprise a priming region having (i) a nucleic acid sequence A' that is hybridizable to the target nucleic acid molecule, (ii) at least one cleavable moiety and a nucleic acid sequence B' that is 3' to the priming region and exhibits sequence complementarity to the priming region. The nucleic acid sequence A' can have a 3' end that is adapted to be extended in a primer extension reaction to form a complement nucleic acid strand of the target nucleic acid molecule only upon cleavage of the cleavable moiety.

In some embodiments, the inactivatable priming oligonucleotide can comprise a priming region having (i) a nucleic acid sequence A that is hybridizable to the target nucleic acid molecule, (ii) at least one cleavable moiety and a nucleic acid sequence B adjacent to the priming region that exhibits sequence complementarity to the priming region. The nucleic acid sequence A can have a 3' end that is adapted to be extended in a primer extension reaction to form a complement nucleic acid strand of the target nucleic acid molecule.

In some embodiments, the inactivatable priming oligonucleotide can be inactivatable upon cleavage of the cleavable moiety of the activatable priming oligonucleotide. In some embodiments, the activatable priming oligonucleotide can be activatable upon cleavage of the cleavable moiety of the inactivatable priming oligonucleotide. In some embodiments, the method further comprises detecting the amplified products of the target nucleic acid molecule. The detecting can be completed via, for example, optical detection, electrostatic detection, or electrochemical detection.

An additional aspect of the disclosure provides a method for nucleic acid amplification. The method can comprise providing a reaction mixture comprising a target nucleic acid molecule, an activatable priming oligonucleotide and an inactivatable priming oligonucleotide, each of which is hybridizable to a different region of the target nucleic acid molecule. The method can further comprise, in the reaction mixture, selectively priming the target nucleic acid molecule with at least a portion of the activatable priming oligonucleotide or at least a portion of the inactivatable priming oligonucleotide. The method can further comprise performing a nucleic amplification reaction using the target nucleic acid molecule selectively primed with at least a portion of the activatable priming oligonucleotide or at least a portion of the inactivatable priming oligonucleotide to yield an amplified product(s) of the target nucleic acid molecule.

In some embodiments, the target nucleic acid molecule can be selectively primed in the reaction mixture and without removal of contents thereof. In some embodiments, the selectively priming the target nucleic acid molecule with at least a portion of the activatable priming oligonucleotide can be effectuated by an enzyme that activates the activatable priming oligonucleotide to permit a primer extension reaction to yield the amplified product(s). In some embodiments, the enzyme can have endonuclease activity.

In some embodiments, the selectively priming the target nucleic acid molecule with at least a portion of the activatable priming oligonucleotide can be effectuated by an enzyme that inactivates the inactivatable priming oligonucleotide such that it does not form a stable complex with the target nucleic acid molecule. In some embodiments, the enzyme can have endonuclease activity.

In some embodiments, the selectively priming the target nucleic acid molecule with the inactivatable priming oligonucleotide can be effectuated in the absence of an active enzyme having endonuclease activity.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "Fig." herein), of which:

FIG. 2A is a table summarizing various experiments as described in Example 1.

FIG. 4A is a table summarizing various experiments as described in Example 1.

FIG. 8A schematically depicts example strands of example double-stranded probes as described in Example 4 (FIG. 8A discloses SEQ ID NOS: 13-15, respectively, in order of appearance)

FIG. 10C also provides a schematic summarizing an example nucleic acid amplification reaction using both the example inactivatable and example activatable oligonucleotides depicted in FIG. 10A and FIG. 10B;

FIG. 11A is a table summarizing various experiments as described in Example 6.

FIG. 14A and FIG. 14B provide an example target nucleic acid sequence with an example SNP site (note that the top sequence of FIG. 14A is followed by the sequence in FIG. 14B, and the sequence end in FIG. 14B is followed by the second line of sequence in FIG. 14A, all together, they form a single continuous sequence) and an example method to detect a nucleotide in the SNP site as described in Example 5 (FIG. 14A and FIG. 14B disclose SEQ ID NO: 24); FIG. 14C provides example forward and reverse primers as described in Example 5 (FIG. 14C discloses SEQ ID NOS: 25-28, respectively, in order of appearance)

DETAILED DESCRIPTION

Figures 1A, 1B:
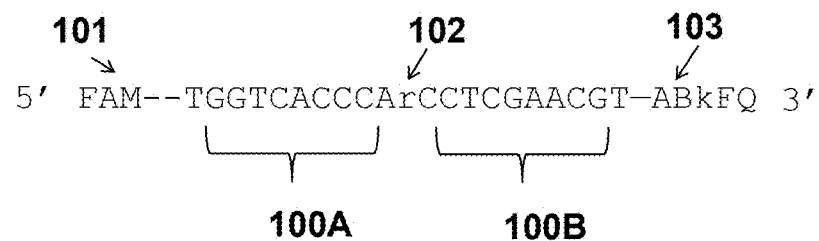
FIG. 1A is a schematic depicting an example probe as described in Example 1 (FIG. 1A discloses SEQ ID NO: 5)
FIG. 1B are example target nucleic acid molecules corresponding to the example probe in FIG. 1A (FIG. 1B discloses SEQ ID NOS: 6-9, respectively, in order of appearance)

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the singular form "a", "an" and "the" include plural references unless the context clearly dictates otherwise. For example, the term "a nucleic acid molecule" includes a plurality of nucleic acid molecules, including mixtures thereof.

As used herein, the terms "amplifying" and "amplification" are used interchangeably and generally refer to producing one or more copies of a nucleic acid. An "amplification reaction" generally refers to a reaction in which amplification of a nucleic acid occurs.

As used herein, the terms "anneal", "annealing", "hybridize" and "hybridizing" generally refer to the binding of one nucleic acid molecule (e.g., a primer or probe) with another nucleic acid molecule (e.g., a template nucleic acid molecule, a target nucleic acid molecule) via complementarity between the nucleic acid molecules.

As used herein, the term "cleavable moiety" generally refers to a labile species or a detachable group included in a nucleic acid molecule (e.g., a priming oligonucleotide, a probe) that can be cleaved such that a nucleic acid molecule is separated into a plurality of shorter nucleic acid molecules. A cleavable moiety may be cleaved by any suitable route, with non-limiting examples that include enzymatic cleavage, photo-cleavage and chemical cleavage (e.g., via an appropriate pH condition).

"Complementarity", "complementary" generally refer to the ability of a nucleic acid to form hydrogen bond(s) with another nucleic acid according to Watson-Crick base-pairing rules or other types of nucleic acid base-pairing rules. A "complement" of a nucleic acid strand generally refers to another strand of nucleic acid that is complementary to the nucleic acid strand. "Partially complementary" generally means that a portion of a first nucleic acid sequence will hydrogen bond (e.g., base-pair) with a portion of a second nucleic acid sequence. "Substantially complementary" or "substantial complementarity" generally refers to a degree of complementarity that is at least 60%, 65%, 70%, 75%, 80%, 85%, 90%, 95%, 97%, 98%, 99%, or 100% over a region of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more nucleotides.

As used herein, the term "cycle threshold" or "Ct" generally refers to the cycle during an amplification reaction in which an increase in a detectable signal due to amplified product reaches a statistically significant level above background signal.

As used herein, the terms "denaturing" and "denaturation" are used interchangeably and generally refer to the full or partial unwinding of the helical structure of a double-stranded nucleic acid, and in some embodiments the unwinding of the secondary structure of a single stranded nucleic acid.

As used herein, a "detectable moiety" generally refers to a composition that yields a detectable signal, the presence or absence of which can be used to detect the presence of a nucleic acid and/or copies of a nucleic acid. In some embodiments, a detectable moiety may be an optically detectable moiety such that the detectable moiety yields a detectable signal in the presence (or absence) of electromagnetic radiation, such as, for example, light. In some embodiments, a detectable moiety may be included in a probe. In some embodiments, a detectable moiety may be coupled with a quencher that, when in suitable proximity to the detectable moiety, minimizes or prevents the detectable moiety from yielding its detectable signal. In some embodiments, a detectable moiety may be a label that can identify a species associated with the detectable moiety.

As used herein, the term "melting temperature" generally refers to the temperature at which two single-stranded nucleic acid molecules that are hybridized and form a double-stranded molecule dissociate (e.g., via the thermal disruption of hydrogen bonding between hybridized, complementary bases) from each other. In some embodiments, a melting temperature can refer to a temperature at which about 5%, 10%, 15%, 20%, 25%, 30%, 35%, 40%, 45%, 50%, 55%, 60%, 65%, 70%, 75%, 80%, 85%, 90%, 95%, 99% or more identical nucleic acid strands of a population of identical double-stranded nucleic acid molecules dissociate from their complement strands. For example, the melting temperature of a double-stranded nucleic acid molecule may refer to the temperature at which about half of the molecules of the double stranded nucleic acid molecule dissociate into their component strands. In some embodiments, the melting temperature of a nucleic acid sequence may be about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., or higher.

As used herein, the term "nucleic acid" and "nucleic acid molecule" are used interchangeably and generally refer to a polymeric form of nucleotides of any length, either deoxyribonucleotides (dNTPs) or ribonucleotides (rNTPs), or analogs thereof. Nucleic acids may have any three dimensional structure, and may perform any function, known or unknown. Non-limiting examples of nucleic acids include deoxyribonucleic acid (DNA), ribonucleic acid (RNA), a peptide nucleic acid (PNA), a locked nucleic acid (LNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a detectable moiety. In some embodiments, a nucleic acid may be a primer that, in some embodiments, can be used to amplify another nucleic acid molecule.

As used herein, the term "primer" generally refers to a nucleic acid molecule that is capable of hybridizing with a template nucleic acid molecule and capable of being extended in a template-directed manner via the template nucleic acid molecule. A "priming oligonucleotide", as used herein, generally refers to an oligonucleotide that comprises a nucleic acid sequence that can function as a primer. Such a nucleic acid sequence may be included in a "priming region" of a priming oligonucleotide. In some embodiments, a primer can be single-stranded or partially double-stranded.

As used herein, the term "primer extension reaction" generally refers to the binding (e.g., "annealing") of a primer to a strand of nucleic acid, followed by incorporation of nucleotides to the primer (e.g., "extension" of or "extending" the primer), using the strand of nucleic acid as a template. A primer extension reaction may be completed with the aid of an enzyme, such as, for example a polymerase.

As used herein, the term "probe" generally refers to a nucleic acid molecule (e.g., oligonucleotide) that can yield a detectable signal (or absence thereof) upon hybridizing with a target nucleic acid molecule and/or amplification of the target nucleic acid molecule. In some embodiments, a probe may include a detectable moiety, a quencher and a cleavable moiety such that when the cleavable moiety is cleaved, the detectable moiety and quencher separate permitting the detectable moiety to yield its detectable signal.

As used herein, the term "reaction mixture" or "amplification reaction mixture" generally refers to a composition comprising one or more reagents necessary to complete a primer extension reaction and/or nucleic acid amplification, with non-limiting examples of such reagents that include one or more primers having specificity for a target nucleic acid, a polymerase, suitable buffers, co-factors (e.g., divalent and monovalent cations), nucleotides (e.g., deoxyribonucleotides (dNTPs)), and any other enzymes. In some embodiments, a reaction mixture can also comprise one or more probes and/or detectable moieties suitable for detecting a species in an amplification reaction.

As used herein, the terms "target nucleic acid" and "target nucleic acid molecule" are used interchangeably and generally refer to a nucleic acid molecule in a starting population of nucleic acid molecules having a target sequence whose presence, amount, and/or nucleotide sequence, or changes in one or more of these, are desired to be determined. In some embodiments, a target nucleic acid molecule may be double-stranded. In some embodiments, a target nucleic acid molecule may be single-stranded. For example, a single-stranded target nucleic acid molecule can include a strand of a double-stranded nucleic acid molecule. In some embodiments, a target nucleic acid molecule may be partially single-stranded and partially double-stranded. A target nucleic acid molecule may be a portion of a gene, a regulatory sequence, genomic DNA, cDNA, RNA including mRNA, miRNA, rRNA, or others. The target nucleic acid molecule may be a target nucleic acid molecule from a sample or a secondary target such as a product of an amplification reaction.

Some aspects of the disclosure provide probes and methods for using such probes to detect a single nucleotide polymorphism (SNP). Such probes may comprise a cleavable moiety that can be cleaved upon hybridization with a target nucleic acid molecule. Cleavage of the cleavable moiety can yield a detectable signal from a detectable moiety associated with a probe.

In one aspect, the disclosure provides a probe. The probe can include a nucleic acid sequence that is complementary to a single-stranded target nucleic acid molecule and has at least one cleavable moiety; a detectable moiety; and a quencher. The quencher can quench the detectable moiety when the probe is not hybridized to the single-stranded target nucleic acid molecule.

The probe may be single-stranded or double-stranded. Moreover, in some embodiments, the probe may not be capable of intramolecular hybridization. For example, the probe may not be capable of self-hybridization, such as where the probe adopts a configuration comprising at least a portion of its sequence hybridized with another portion of its sequence. In some embodiments, the probe may comprise a nucleotide sequence A and a nucleotide sequence B that flank the at least one cleavable moiety. Nucleotide sequence A and nucleotide sequence B can be each complementary to a portion of the single-stranded target nucleic acid molecule.

The cleavable moiety of the probe may be any suitable cleavable moiety with non-limiting examples of a cleavable moiety that include a ribose moiety, a disulfide moiety, an azide moiety, an enzymatically cleavable linker, a nucleophile/base sensitive linker, a reduction-sensitive linker, a photocleavable linker, an electrophile/acid sensitive linker, a metal-assisted cleavage linker, an oxidation sensitive linker and combinations thereof. In some embodiments, the probe may comprise a plurality of cleavable moieties. Moreover, the cleavable moiety of the probe may be cleavable by any suitable route. For example, the cleavable moiety of the probe may be cleavable upon hybridization of the probe to the single-stranded target nucleic acid molecule. In some embodiments, the cleavable moiety may be cleavable at alkaline conditions (e.g., a pH of greater than 7). For example, the cleavable moiety may be cleavable at a pH of about 7 to 14, about 8 to 11 or about 9 to 10. In some embodiments, the cleavable moiety may be cleavable at a pH of about 7.1, 7.5, 8.0, 8.5, 9.0, 9.5, 10.0, 10.5, 11.0, 11.5, 12.0, 12.5, 13.0, 13.5 or 14.0. Furthermore, the probe may be cleavable without the aid of an enzyme (e.g., a polymerase, enzyme comprising endonuclease activity, enzyme comprising 3' to 5' exonuclease activity, etc.).

In some embodiments, the probe may be adapted to hybridize to the single-stranded target nucleic acid molecule such that the cleavable moiety is situated at a single nucleotide polymorphism (SNP) site of the single-stranded target nucleic acid molecule. The cleavable moiety may be complementary or non-complementary with respect to a nucleotide at the SNP site. Complementarity of the cleavable moiety with the nucleotide in the SNP site may aid in rendering the cleavable moiety more labile. Conversely, weak or lack of complementarity of the cleavable moiety with the nucleotide in the SNP site may render the cleavable moiety less labile. Accordingly, the cleavable moiety of a probe designed to detect a SNP may be designed such that it is complementary to a particular nucleotide in the SNP site.

The detectable moiety of the probe may be any suitable detectable moiety including example detectable moieties described elsewhere herein. In some embodiments, the detectable moiety may be an optically detectable moiety such as, for example, a fluorophore or other dye. Additionally, the detectable moiety of the probe can be adapted to provide a detectable signal (e.g., an optical signal, electrochemical signal, electrostatic signal) upon hybridization of the probe to the single-stranded target nucleic acid molecule. Moreover, a detectable moiety may be positioned at any suitable location of the probe such as, for example, at the 3' end of the probe, at the 5' end of the probe, at a location between the 3' and 5' ends of the probe, on a strand of a double-stranded probe that does not contain a quencher, or at an opposite end of the probe from a quencher. A detectable moiety may be coupled to the probe directly or indirectly via a linker. Coupling of a detectable moiety may be achieved via any suitable route including covalent and/or non-covalent routes described elsewhere herein.

Furthermore, the quencher of the probe may be any suitable quencher with non-limiting examples of quenchers that include IABkFQ quencher, ABkFQ quencher, and black hole quencher (BHQ). Moreover, a quencher may be positioned at any suitable location of the probe such as, for example, at the 3' end of the probe, at the 5' end of the probe, at a location between the 3' and 5' ends of the probe, on a strand of a double-stranded probe that does not contain a detectable moiety, or at an opposite end of the probe from a detectable moiety. A quencher may be coupled to the probe directly or indirectly via a linker. Coupling of a quencher may be achieved via any suitable route including covalent and/or non-covalent routes described elsewhere herein.

An example of a probe is schematically shown in FIG. 1A. As shown in FIG. 1A, the example probe comprises, from 5' to 3', a detectable moiety (e.g., FAM fluorophore) 101, a cleavable moiety (e.g., a ribose moiety "rC") 102 and a quencher (e.g., ABkFQ quencher) 103. The probe also includes a nucleotide sequence 100A and a nucleotide sequence 100B that flank the cleavable moiety 102 and are complementary to a sequence on a target nucleic acid molecule. Upon hybridization of the probe to the sequence, the cleavable moiety 102 can be cleaved such that the detectable moiety 101 and quencher 103 separate, resulting a detectable signal from the detectable moiety 101 being generated. Additional example probes are provided in the Examples section provided below.

In some embodiments, the probe may be included in a solution such as, for example, an amplification reaction mixture. Such a reaction mixture may include the probe, the single-stranded target nucleic acid molecule and any additional reagents suitable for amplification of the single-stranded target nucleic acid molecule, as described elsewhere herein. Additional examples of solutions include water, a buffer, a solvent, a biological fluid, a fluid containing salts, a fluid containing nucleotides, a fluid containing enzymes, a fluid containing additives and combinations thereof. In some embodiments, the solution may comprise an alkaline buffer with non-limiting examples of such buffers that include a buffer comprising tris base, a buffer comprising sodium hydroxide, a buffer comprising potassium hydroxide, a buffer comprising ammonium hydroxide and a buffer comprising sodium carbonate. Alkaline conditions in the solution may aid in cleaving the cleavable moiety of the probe.

In some embodiments, the probe may be immobilized onto the substrate of an array. Such a substrate of an array may be a solid substrate that may comprise a material selected from the group consisting of a metal, a semi-metal, a glass, a polymer (e.g., an organic polymer), a metal oxide, a silicon oxide, a silicon nitride, combinations thereof and composites thereof. In some embodiments, the probe may be immobilized in a well of the substrate of an array, such as, for example, a well of a microwell plate. A probe may be immobilized to the substrate of an array via any suitable method including both covalent and non-covalent attachment. Covalent attachment of the probe to the array may be direct or indirect via a linker between the probe and the array. Non-covalent attachment may via, for example, van der Waals forces, ionic interactions, hydrophobic interactions, or binding of members of a binding pair (e.g., streptavidin/biotin).

Another aspect of the disclosure provides a method for detecting a single nucleotide polymorphism (SNP). The method can comprise providing a reaction mixture comprising a single-stranded target nucleic acid molecule and probe. The probe can have a nucleic acid sequence with at least one cleavable moiety; a detectable moiety; and a quencher. Moreover, the probe can be complementary to the single-stranded target nucleic acid molecule and the quencher can quench the detectable moiety when the probe is not hybridized to the single-stranded target nucleic acid molecule. The probe hybridized with the single-stranded target nucleic acid molecule, where upon hybridization, the cleavable moiety is disposed adjacent to a nucleotide in a single nucleotide polymorphism (SNP) site of the single-stranded target nucleic acid molecule. A signal can then be detected from the probe that is indicative of the presence of the nucleotide in the SNP site.

The hybridizing of the probe to the single-stranded target nucleic acid molecule and/or the detecting the signal from the probe may be performed without the aid of an enzyme (e.g., polymerase, enzyme with endonuclease activity, enzyme with 3' to 5' exonuclease activity) and/or without cycling a temperature of the reaction mixture. In some embodiments, the pH of the reaction may be maintained at alkaline conditions (e.g., at a pH above 7). For example, the pH of the reaction mixture may be maintained at a pH of about 7 to 14, about 8 to 11 or about 9 to 10. In some embodiments, the pH of reaction may be maintained at a pH of about 7.1, 7.5, 8.0, 8.5, 9.0, 9.5, 10.0, 10.5, 11.0, 11.5, 12.0, 12.5, 13.0, 13.5 or 14.0.

Additionally, the signal from the probe may be an optical signal, an electrostatic signal or an electrochemical signal as described elsewhere herein. In some embodiments, the single-stranded target nucleic acid molecule may not contain a detectable moiety. Moreover, the probe may be immobilized on the substrate of an array, as described elsewhere herein. For example, the probe may be immobilized in a well of the array.

The probe may include any additional features including additional features of the probes described elsewhere herein. For example, the probe may comprise a plurality of cleavable moieties and/or may comprise a nucleotide sequence A and a nucleotide sequence B flanking the cleavable moiety, and wherein the nucleotide sequence A and nucleotide sequence B are each complementary to a portion of the single-stranded target nucleic acid molecule. In addition, the cleavable moiety may be complementary or non-complementary with respect to the nucleotide in the SNP site. Moreover, the detectable moiety of the probe may have any suitable features including features of a detectable moiety of a probe as described elsewhere herein. For example, the detectable moiety may be adapted to provide the signal upon hybridization of the probe to the single-stranded target nucleic acid molecule. In addition, the cleavable moiety of the probe may have any suitable features including features of a cleavable moiety of a probe as described elsewhere herein. For example, the cleavable moiety may be cleaved upon hybridization of the probe to the single-stranded target nucleic acid molecule.

Additional aspects of the disclosure provide methods for detecting a single nucleotide polymorphism (SNP) via amplification of nucleic acids with primers that include purine or pyrimidine derivatives. Such purine or pyrimidine derivatives may preferentially hybridize with a particular type of nucleotide in a SNP site. A target nucleic acid molecule can be amplified in parallel reaction mixtures with one set of reaction mixtures including a primer comprising a purine derivative in its site corresponding to a SNP site of a target nucleic acid molecule and the other set of reaction mixtures including a primer comprising a pyrimidine derivative in its site corresponding to a SNP site of the target nucleic acid molecule. Amplification products can be detected in each reaction mixture and the results of detection compared.

An aspect of the disclosure provides a method for detecting a single nucleotide polymorphism (SNP). The method comprises providing a first reaction mixture comprising a first strand of a target nucleic acid molecule; and a first primer having a purine derivative at a nucleotide site of the first primer that corresponds to a nucleotide site of the first strand that is suspected of comprising a first nucleotide site of a single nucleotide polymorphism (SNP). The purine derivative can preferentially hybridize with a pyrimidine base of the first strand over other types of bases of the first strand. The method further comprises providing a second reaction mixture comprising a complementary strand of the first strand of the target nucleic acid molecule and a second primer having a pyrimidine derivative at a nucleotide site of the second primer that corresponds to a nucleotide site of the complementary strand that is suspected of comprising a second nucleotide site of the SNP, wherein the pyrimidine derivative preferentially hybridizes with an purine base of the complementary strand over other types of bases of the complementary strand. The first and second reaction mixture are then subjected to conditions such that the first primer is extendable upon hybridization to the first strand to yield a first nucleic acid product and the second primer is extendable upon hybridization to the complementary strand to yield a second nucleic acid product. Following the generation of the first and second nucleic acid products, the relative quantities of first and second nucleic acid products are then determined.

In some embodiments, the first and second reaction mixtures may be isolated from each other such, as for example, situated in separate containers. In addition, a greater quantity of the first nucleic acid product determined in relation to the second nucleic acid product can be indicative of the presence of a purine base at the first nucleotide site of the SNP. A greater quantity of the second nucleic acid product determined in relation to the first nucleic acid product can be indicative of the presence of a pyrimidine base at the second nucleotide site of the SNP.

The purine derivative of the first primer may be any suitable purine derivative including one of the natural purines (e.g., adenine or guanine) or an unnatural purine of a nucleic acid molecule. In some embodiments, though, the purine derivative of the first primer may not be guanine or may not be adenine. In such embodiments, the purine derivative of the first primer may be hypoxanthine or a derivative thereof. Hypoxanthine can be found in an inosine nucleotide. Moreover, in some embodiments, the purine derivative of the first primer can be replaceable by an adenine base or guanine with the aid of an enzyme, such as, for example an enzyme having 3' to 5' exonuclease activity or an endonuclease. Non-limiting examples of an enzyme having 3' to 5' exonuclease activity include Phusion polymerase, Pfu polymerase, DEEPVENT polymerase, exonuclease I, exonuclease III, exonuclease IV, exonuclease V, KOD polymerase, Q5 polymerase, Accura High-Fidelity Polymerase, Phi 29 polymerase, Bst polymerase, DNA polymerase I, T4 polymerase and T7 polymerase. Non-limiting examples of enzymes with endonuclease activity (e.g., an endonuclease) include deoxyribonuclease I, Type I restriction endonucleases, Type II restriction endonucleases, Type III restriction endonucleases, an RNase (e.g., RNase HI, RNase HII or RNase HIII), uracil N-glycosylase (UNG), T7 endonuclease, T4 endonuclease IV, Bal 31 endonuclease, S1 nuclease, Mung Bean nuclease, endonuclease I, endonuclease II and endonuclease R. In some embodiments, an enzyme with endonuclease activity may be thermal stable. In some embodiments, an enzyme with endonuclease activity may be activatable or inactivatable. Activation or inactivation of an endonuclease may be achieved, for example, via thermally labile chemical modifications. Inactivation or activation may also be achieved, for example with an aptamer or antibody.

Similarly, the pyrimidine derivative of the second primer may be any suitable pyrimidine derivative including one of the natural pyrimidines (e.g., thymine or cytosine) or may be an unnatural pyrimidine of a nucleic acid molecule. In some embodiments, though, the pyrimidine derivative of the second primer may not be thymine or cytosine. In such embodiments, the pyrimidine derivative of the second primer may be uracil or a derivative thereof. Moreover, in some embodiments, the purine derivative of the second primer can be replaceable by a thymine or cytosine base with the aid of an enzyme, such as, for example an enzyme having 3' to 5' exonuclease activity or an endonuclease. Additionally, the pyrimidine base of the first strand that the purine derivative of the first primer preferentially hybridizes with can be any pyrimidine base including cytosine and thymine. The purine base of the complementary strand that the pyrimidine derivative of the second primer preferentially hybridizes with can be any purine base including adenine and guanine.

In some embodiments, the first and/or second reaction mixtures may comprise a detectable moiety. The detectable moiety may be any suitable detectable moiety including examples types of detectable moieties described elsewhere herein. For example, the detectable moiety may be an optically detectable moiety, such as a fluorescent dye (e.g., SYBR green, EvaGreen, BEBO, BOXTO, an intercalating dye). The detectable moiety in a reaction mixture can aid in the detection of amplification products in the reaction mixture during amplification. Detection, via an appropriate mode of detection (including examples modes of detection described elsewhere herein), can aid in the determining of the relative quantities of the first and second nucleic acid products.

In some embodiments, the determining of the relative quantities of the first and second nucleic acid products may be with aid of a melting curve analysis. In a melting curve analysis, a mixture (e.g., an amplification reaction mixture) comprising double-stranded nucleic acid molecules (e.g., amplification products) can be heated and dissociation (e.g., denaturing) of the double-stranded nucleic acid molecules in the mixture can be measured against temperature. The temperature-dependent dissociation of strands of a double-stranded nucleic molecule can be measured using a detectable moiety that can intercalate or bind double-stranded nucleic acid molecules. For example, in the case of an intercalator (e.g., SYBR green) that fluoresces when bound to a double-stranded nucleic acid molecule, the dissociation of double-stranded nucleic acid molecules and release of bound intercalator during heating can be determined by a reduction in fluorescence that results. The free intercalator may not fluoresce (or may not fluoresce at the same wavelength as the bound species) and thus, a reduction in fluorescence may be used to indicate a dissociation of double-stranded nucleic acid molecules. The first derivative or negative first derivative of dissociation (e.g., negative first derivative of fluorescence) as a function of temperature may be plotted to determine a temperature of dissociation (e.g., temperature at which 50% dissociation occurs) via peaks in the plot. A nucleic acid molecule may be identified via the obtained dissociation profile and/or temperature of dissociation.

In some embodiments, the determining of the relative quantities of the first and second nucleic acid products may be with the aid of a change in cycle threshold ($\Delta C_t$). The $C_t$ value for each of the first and second nucleic acid products can be determined and a difference taken in order to determine the relative quantities of the first and second nucleic acid products.

In some embodiments, the determining of the relative quantities of the first and second nucleic acid products may be with the aid of any other suitable method including, for example, gel electrophoresis. In some embodiments, the determining of the relative quantities of the first and second nucleic acid products may be with the aid of a computer processor that is programmed to compare the relative quantities of the first and the second nucleic acid products. Such a computer processor may be included as part of a computer system as described elsewhere herein.

Figure 13A:
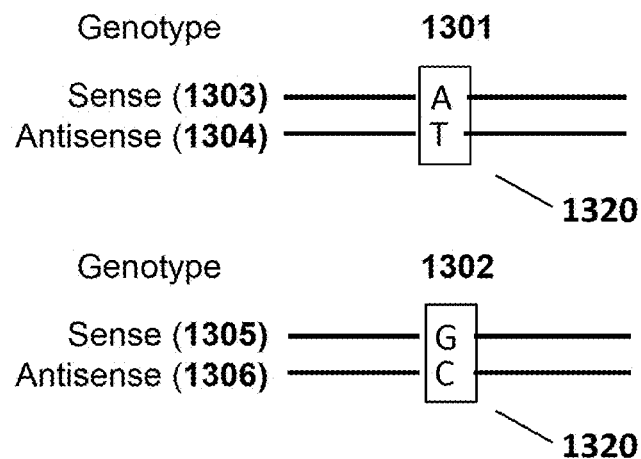
FIG. 13A is a schematic depicting an example single nucleotide polymorphism (SNP) in a nucleic acid molecule.
Figure 13B:
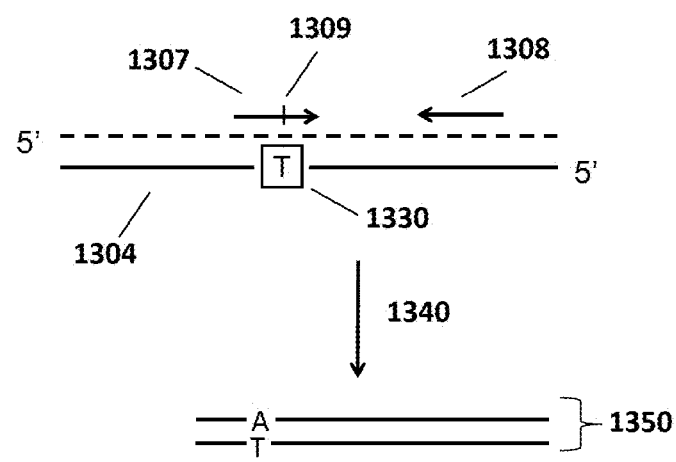
FIG. 13B and FIG. 13C are schematics depicting example methods for detecting the example SNPs depicted in FIG. 13A.
Figure 13C:
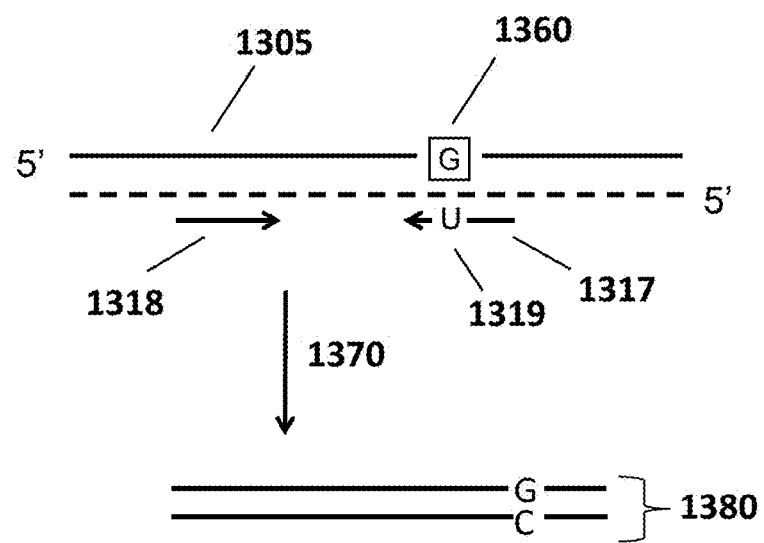

An example of detecting two genotypes corresponding to a SNP in a target nucleic acid molecule is schematically depicted in FIG. 13A-13C. As shown in FIG. 13A, a particular target nucleic acid may have a SNP site 1320 that in a first genotype 1301 comprises an adenine containing nucleotide ("A") in its sense strand 1303 and a thymine containing nucleotide ("T") in its antisense strand 1304. In a second genotype 1302, the target nucleic acid molecule comprises a guanine containing nucleotide ("G") in its sense strand 1305 and a cytosine containing nucleotide ("C") in its antisense strand in the SNP site 1320.

To detect first genotype 1301, the target nucleic acid molecule can be provided in a reaction mixture along with a forward primer 1307, a reverse primer 1308, a polymerase (e.g., Pfu polymerase) comprising 3' to 5' exonuclease activity and any other reagents necessary for amplification of the target nucleic acid molecule as depicted schematically in FIG. 13B. As shown in FIG. 13B, both the forward primer 1307 and reverse primer 1308 can comprise a tail that can be cleaved via the 3' to 5' exonuclease activity of the polymerase. The tails of the forward primer 1307 and reverse primer 1308 can aid in minimizing the generation of primer dimer by-products during amplification of the target nucleic acid molecule. In its tail, the forward primer 1307 can comprise an inosine nucleotide 1309 ("I") that can be removed by the polymerase with 3' to 5' exonuclease activity when bound to the thymine containing nucleotide in the SNP site 1330 of the antisense strand 1304 of the target nucleic acid molecule.

The inosine nucleotide 1309 comprises a hypoxanthine base that generally binds better with a cytosine containing nucleotide (a "preferred" complement nucleotide of the inosine nucleotide 1309) than the thymine containing nucleotide (a "non-preferred" complement nucleotide of inosine nucleotide 1309) at the SNP site 1330 of antisense strand 1304 of the target nucleic acid molecule. Due to the relatively weak binding of the inosine nucleotide 1309 and thymine containing nucleotide of the antisense strand 1304 of the target nucleic acid molecule, the 3' to 5' exonuclease activity of the polymerase can remove the inosine nucleotide 1309 from the forward primer 1307 during cleavage of the tail of forward primer 1307. Following cleavage of the tail from the forward primer 1307, the polymerase can then extend the 3' end of the forward primer 1307 such that the natural complement nucleotide (adenine-containing nucleotide "A") of the thymine containing nucleotide in the SNP site 1330 of the antisense strand 1304 is added to the forward primer 1307 at the SNP site 1330.

The temperature of the reaction mixture is cycled through annealing and extension temperatures as described elsewhere herein such that the forward primer 1307 anneals to the antisense strand 1304 of the target nucleic acid molecule, the tail comprising the inosine nucleotide 1309 is removed via the 3' to 5' exonuclease activity of the polymerase, and the 3' end of the forward primer 1307 is extended. Extension can result in the generation of an amplified double-stranded nucleic acid molecule comprising an adenine containing nucleotide in place of the inosine nucleotide 1309 in the sense strand SNP site of double-stranded nucleic acid molecule. Since the inosine nucleotide 1309 is removed by the polymerase, the double-stranded nucleic acid molecule can then be subject to multiple cycles of amplification 1340 using the forward primer 1307 and reverse primer 1308 to generate additional amplified double-stranded nucleic acid molecules 1350. The amplified double-stranded nucleic acid molecules 1350 can be detected and the genotype of the target nucleic acid molecule determined to be genotype 1301 based on the presence of amplified double-stranded nucleic acid molecules 1350.

In some cases, primer 1307 may be extended without cleavage of the inosine nucleotide 1309 of forward primer 1307. When this occurs, the reverse primer 1308 may anneal to the newly synthesized strand but the polymerase (e.g., Pfu polymerase) may lose or cease to have activity upon encountering the inosine nucleotide 1309 as a template nucleotide. This reduction or loss of polymerase activity can minimize the production of undesired amplification products comprising inosine nucleotide 1309. By way of example, if forward primer 1307 were used to amplify a nucleic acid strand comprising genotype 1302, inosine nucleotide 1309 would generally not be cleaved and instead present in an extended strand comprising forward primer 1307. However, as is discussed above, such an inosine nucleotide 1309 in the extended strand would result in the loss or inhibition of a polymerase upon contact with the inosine nucleotide 1309. Thus, forward primer 1307 can be used to selectively amplify a nucleic acid containing genotype 1301 over a nucleic acid comprising genotype 1302.

To detect second genotype 1302, the target nucleic acid can be provided in a reaction mixture along with a forward primer 1317, a reverse primer 1318, a polymerase (e.g., Pfu polymerase) comprising 3' to 5' exonuclease activity and any other reagents necessary for amplification of the target nucleic acid molecule as depicted schematically in FIG. 13C. As shown in FIG. 13C, both the forward primer 1317 and reverse primer 1318 can comprise a tail that can be cleaved via the 3' to 5' exonuclease activity of the polymerase. In its tail, the forward primer 1317 can comprise an uracil containing nucleotide 1319 ("U") that can be removed by the polymerase with 3' to 5' exonuclease activity when bound to the guanine containing nucleotide in the SNP site 1360 of the sense strand 1305 of the target nucleic acid molecule.

The uracil containing nucleotide 1319 comprises a uracil base that generally binds better with an adenine containing nucleotide (a "preferred" complement nucleotide of the uracil containing nucleotide 1319) than the guanine containing nucleotide (a "non-preferred" complement nucleotide of uracil containing nucleotide 1319) at the SNP site 1360 of sense strand 1305 of the target nucleic acid molecule. Due to the relatively weak binding of the uracil containing nucleotide 1319 and guanine containing nucleotide of the sense strand 1305 of the target nucleic acid molecule, the 3' to 5' exonuclease activity of the polymerase can remove the uracil containing nucleotide 1319 from the forward primer 1317 during cleavage of the tail of forward primer 1317. Following cleavage of the tail from the forward primer 1317, the polymerase can then extend the 3' end of the forward primer 1317 such that the natural complement nucleotide (cytosine-containing nucleotide "C") of the guanine containing nucleotide in the SNP site 1360 of the sense strand 1305 is added to the forward primer 1317 at the SNP site 1360.

The temperature of the reaction mixture can be cycled through annealing and extension temperatures as described elsewhere herein such that the forward primer 1317 anneals to the sense strand 1305 of the target nucleic acid molecule, the tail comprising the uracil containing nucleotide 1319 is removed via the 3' to 5' exonuclease activity of the polymerase, and the 3' end of the forward primer 1317 is extended. Extension can result in the generation of an amplified double-stranded nucleic acid molecule comprising a cytosine containing nucleotide in place of the uracil containing nucleotide 1319 in the antisense strand SNP site of double-stranded nucleic acid molecule. Since the uracil containing nucleotide 1319 is removed by the polymerase, the double-stranded nucleic acid molecule can then be subject to multiple cycles of amplification 1370 using the forward primer 1317 and reverse primer 1318 to generate additional amplified double-stranded nucleic acid molecules 1380. The amplified double-stranded nucleic acid molecules 1380 can be detected and the genotype of the target nucleic acid molecule determined to be genotype 1302 based on the presence of amplified double-stranded nucleic acid molecules 1380.

In some cases, forward primer 1317 may be extended without cleavage of the uracil nucleotide 1319 of forward primer 1317. When this occurs, the reverse primer 1318 may anneal to the newly synthesized strand but the polymerase (e.g., Pfu polymerase) may lose or cease to have activity upon encountering the uracil nucleotide 1319 as a template nucleotide. This reduction or loss of polymerase activity can minimize the production of undesired amplification products comprising uracil nucleotide 1319. By way of example, if forward primer 1317 were used to amplify a nucleic acid strand comprising genotype 1301, uracil nucleotide 1319 would generally not be cleaved and instead present in an extended strand comprising forward primer 1317. However, as is discussed above, such a uracil nucleotide 1319 in the extended strand would result in the loss or inhibition of a polymerase upon contact with the uracil nucleotide 1319. Thus, forward primer 1317 can be used to selectively amplify a nucleic acid containing genotype 1302 over a nucleic acid comprising genotype 1301.

The example methods for detecting genotypes 1301 and 1302 shown in FIGS. 13A-13C can be used simultaneously to detect the particular genotype in a nucleic acid sample. The nucleic acid sample can be split and provided to two amplification reaction mixtures. In addition to an appropriate reverse primer, a polymerase with 3' to 5' exonuclease activity and any other reagents necessary to amplify a target nucleic acid molecule in the nucleic acid sample, each of the reaction mixtures can comprise either forward primer 1307 or forward primer 1317. The reaction mixtures can then be subject to conditions suitable to amplify the target nucleic acid molecule in the nucleic acid sample. The relative levels of amplification products (corresponding to amplification via forward primer 1307 or forward primer 1317) in each reaction mixture can be used together to determine which genotype is present in the original nucleic acid sample. If the reaction mixture comprising forward primer 1307 generates a higher level of amplification products than the reaction mixture comprising forward primer 1317, then it can be generally determined that the nucleic acid sample comprises genotype 1301. If the reaction mixture comprising forward primer 1317 generates a higher level of amplification products than the reaction mixture comprising forward primer 1307, then it can be generally determined that the nucleic acid sample comprises genotype 1302.

Additional aspects of the disclosure provide inactivatable priming oligonucleotides and methods for inactivating such priming oligonucleotides. An inactivatable priming oligonucleotide can include a cleavable moiety and/or sequences with varied melting temperatures. Such inactivatable priming oligonucleotides can be inactivated via cleavage of the cleavable moiety and/or the manipulation of temperature.

An additional aspect of the disclosure provides an inactivatable priming oligonucleotide. The inactivatable priming oligonucleotide can comprise a priming region having a nucleic acid sequence A that is hybridizable to a single-stranded target nucleic acid molecule. The 3' end of the nucleic acid sequence A can be adapted to be extended in a primer extension reaction to form a complement nucleic acid strand of the single-stranded target nucleic acid molecule. The priming region can also include at least one cleavable moiety. In addition, the inactivatable priming oligonucleotide can also comprise a nucleic acid sequence B adjacent to the priming region that exhibits sequence complementarity to the priming region.

In another aspect, the disclosure provides an inactivatable priming oligonucleotide. The inactivatable priming oligonucleotide can comprise a priming region having a nucleic acid sequence A that is hybridizable to a single-stranded target nucleic acid molecule. The 3' end of the nucleic acid sequence A can be adapted to be extended in a primer extension reaction to form a complement nucleic acid strand of the single-stranded target nucleic acid molecule. The priming region can also include at least one cleavable moiety. In addition, the inactivatable priming oligonucleotide can also comprise a nucleic acid sequence B adjacent to the priming region. The priming region can have a first melting temperature and the nucleic acid sequence B can have a second melting temperature that is less than the first melting temperature.

An inactivatable priming oligonucleotide described herein may be a loop inactivatable priming oligonucleotide in that its sequence may comprise regions that are complementary to each other. Such regions of a loop inactivatable priming oligonucleotide can hybridize with one another to form a loop structure (e.g., a hairpin structure) in the inactivatable priming oligonucleotide. For example, all or a portion of a nucleic acid sequence B may exhibit sequence complementarity to a priming region of an inactivatable priming oligonucleotide.

Moreover, in some embodiments, the 3' end of a nucleic acid sequence A may only be extendable at a temperature equal to or above a melting temperature of a nucleic acid sequence B. In some embodiments, a priming region of an inactivatable priming oligonucleotide may include, from 3' to 5', a nucleic acid sequence A, a cleavable moiety, an a nucleic acid sequence A' that is complementary to a single-stranded target nucleic acid molecule. A nucleic acid sequence A' may or may not be complementary to a single-stranded target nucleic acid molecule. In some embodiments, a priming region can have a first melting temperature and a nucleic acid sequence B can have a second melting temperature that is less than the first melting temperature.

A first melting temperature of a priming region may be any suitable melting temperature. For example, a first melting temperature of a priming region may be from about 50° C. to about 80° C., from about 60° C. to about 75° C., or from about 65° C. to about 70° C. In some embodiments, a first melting temperature of a priming region may be at least about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or higher, or lower depending upon the particular inactivatable priming oligonucleotide. A second melting temperature of a nucleic acid sequence B may be any suitable melting temperature can be less than a first melting temperature of a priming region. For example, a second melting temperature of a nucleic acid sequence B may be less than or equal to about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C. depending upon the particular inactivatable priming oligonucleotide.

In some embodiments, a second melting temperature of a nucleic acid sequence B may be less than a first melting temperature of a priming region by about 1° C. to about 80° C., from about 5° C. to about 30° C., or from about 10° C. to about 20° C. In some embodiments, a second melting temperature of a nucleic acid sequence B may be less than a first melting of a priming region by about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44°

C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C.

In some embodiments, a priming region may comprise additional sequences to a nucleic acid sequence A. For example, a priming region may comprise a nucleic acid sequence A'. In such embodiments, a nucleic acid sequence A may have a third melting temperature that may be less than a first melting temperature of a priming region as a whole and/or a second melting temperature of a nucleic acid sequence B upon cleavage of the cleavable moiety. A third melting temperature of a nucleic acid sequence A may be any suitable melting temperature. In some embodiments, a third melting temperature of a nucleic acid sequence A may less than or equal to about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C. depending upon the particular inactivatable priming oligonucleotide. In some embodiments, a third melting temperature of a nucleic acid sequence A may be less than a first melting temperature of a priming region and/or a second melting temperature of a nucleic acid sequence B by about 1° C. to about 80° C., from about 5° C. to about 30° C., or from about 10° C. to about 20° C.

Moreover, a nucleic acid sequence B may or may not be complementary to the single-stranded target nucleic acid molecule and/or a complement of the single-stranded target nucleic acid molecule. In some embodiments, a nucleic acid sequence B may be at least partially complementary to a complement of the single-stranded target nucleic acid molecule. In some embodiments, a nucleic acid sequence B may comprise a spacer that is not complementary to a priming region and/or a single-stranded target nucleic acid molecule. Such a spacer may be a region of the inactivatable priming oligonucleotide that cannot be copied via a polymerase during a primer extension reaction. For example, the spacer may be a sequence of one, two, three, four, five, six, seven, eight, nine, ten, eleven, twelve, thirteen, fourteen, fifteen, sixteen, seventeen, eighteen, nineteen, twenty or more nucleotides. Such a sequence of oligonucleotides may comprise one or more species that inhibits the action of a polymerase with non-limiting examples that include dSpacer (abasic furan), Spacer C3, hexanediol spacer, Spacer 9, Spacer 12 and Spacer 18.

A cleavable moiety of a priming region of an inactivatable priming oligonucleotide may be any suitable species. In some embodiments, an inactivatable priming oligonucleotide may comprise a plurality of cleavable moieties. Non-limiting examples of cleavable moieties that can be included in a priming region of an inactivatable priming oligonucleotide include ribose, a disulfide linkage, a diazobenzene derivative (e.g., cleavable with $Na_2S_2O_4$), a hydrazone-based linker, a photocleavable spacer (e.g., PC spacer), a thermally cleavable imine base/isocyanate adduct, an azide containing linker, a levulinoyl ester-based linker and an allyl-linker. Moreover, a cleavable moiety of a priming region of an inactivatable priming oligonucleotide may be cleavable by any suitable route. For example, a cleavable moiety of a priming region of an inactivatable priming oligonucleotide may be photo cleavable (e.g., via exposure of the cleavable moiety to light), enzymatically cleavable (e.g., via the action of an enzyme such as an endonuclease, restriction enzyme, ribonuclease (e.g., RNase HI, RNase HII, RNase HIII)) or chemically cleavable (e.g., via an appropriate reducing agent, pH condition or other condition in a reaction mixture). In some embodiments, the cleavable moiety of a priming region of an inactivatable priming oligonucleotide may be cleavable at an alkaline pH.

In some embodiments, an inactivatable priming oligonucleotide may be included in a solution such as, for example, an amplification reaction mixture. Such a reaction mixture may include the inactivatable priming oligonucleotide, the single-stranded target nucleic acid molecule and any additional reagents suitable for amplification of the single-stranded target nucleic acid molecule, as described elsewhere herein. Additional examples of types of additional types of example solutions described elsewhere herein may also include an inactivatable priming oligonucleotide. For example, a solution comprising an inactivatable priming oligonucleotide may comprise an alkaline buffer.

An additional aspect of the disclosure provides a method for inactivating an inactivatable priming oligonucleotide. The method includes providing a solution containing an inactivatable priming oligonucleotide comprising a priming region having a nucleic acid sequence A that is hybridizable to a single-stranded target nucleic acid molecule. The 3' end of the nucleic acid sequence A can be adapted to be extended in a primer extension reaction to form a complement nucleic acid strand of the single-stranded target nucleic acid molecule. The priming region can also include at least one cleavable moiety. The inactivatable priming oligonucleotide can also include a nucleic acid sequence B adjacent to the priming region that exhibits sequence complementarity to the priming region. The method further comprises cleaving the cleavable moiety, which cleaving inactivates the priming region of the inactivatable priming oligonucleotide.

An additional aspect of the disclosure provides a method for inactivating an inactivatable priming oligonucleotide. The method includes providing a solution containing an inactivatable priming oligonucleotide comprising a priming region having a nucleic acid sequence A that is hybridizable to a single-stranded target nucleic acid molecule. The 3' end of the nucleic acid sequence A can be adapted to be extended in a primer extension reaction to form a complement nucleic acid strand of the single-stranded target nucleic acid molecule. In addition, the priming region can also include at least one cleavable moiety. The inactivatable priming oligonucleotide can also include a nucleic acid sequence B adjacent to the priming region. The priming region can have a first melting temperature and the nucleic acid sequence B can have a second melting temperature that is less than the first melting temperature. The method further comprises cleaving the cleavable moiety, which cleaving inactivates the priming region of the inactivatable priming oligonucleotide.

The solution in which inactivatable priming oligonucleotide inactivation takes place may be any suitable solution, including an amplification reaction mixture in which a single-stranded target nucleic acid molecule is amplified. In some embodiments, a priming region can have a first melting temperature and a nucleic acid sequence B has a second melting temperature that is less than the first melting temperature. In some embodiments, a cleavable moiety can be cleaved at a temperature of the solution that is equal to or below a second melting temperature of a nucleic acid sequence B. Thus, a method can further comprise decreasing the temperature of a solution below or equal to a second melting temperature of a nucleic acid sequence B. After decreasing the temperature of a solution to equal to or below a second melting temperature of a nucleic acid sequence B and cleaving a cleavable moiety, the temperature of the solution can then be increased to a temperature equal to or above a first melting temperature of a priming region. In some embodiments, a nucleic acid sequence A may not stably hybridize with a single-stranded target nucleic acid molecule at a temperature equal to or above its melting temperature and/or a first melting temperature.

Moreover, in some embodiments, a priming region may comprise, from 3' to 5', a nucleic acid sequence A, a cleavable moiety adjacent to the nucleic acid sequence A, and a nucleic acid sequence A' that is adjacent to the cleavable moiety. In some embodiments, a priming region may have a first melting temperature that is higher than a second melting temperature of a nucleic acid sequence B. In some embodiments, a priming region may comprise an additional sequence to a nucleic acid sequence A (e.g., a nucleic acid sequence A'). In such embodiments, a nucleic acid sequence A may have a third melting temperature that, upon cleavage of the cleavable moiety, can be less than a first melting temperature of a priming region and, in some embodiments, also lower than a second melting temperature of a nucleic acid sequence B. In some embodiments, a method may further comprise increasing the temperature of a solution to a temperature equal to or above a third melting temperature of a nucleic acid sequence A. Such a temperature increase may aid in preventing a cleaved nucleic acid sequence A of an inactivatable priming oligonucleotide from annealing to a single-stranded target nucleic acid molecule.

A first melting temperature of a priming region, a second melting temperature of a nucleic acid sequence B and, where appropriate a third melting temperature of a nucleic acid sequence A may be any suitable melting temperature. For example, a first melting temperature of a priming region may be at least about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or higher, or lower depending upon the particular inactivatable priming oligonucleotide. In some embodiments, a second melting temperature of a nucleic acid sequence B may be less than or equal to about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C. In some embodiments, a third melting temperature of a nucleic acid sequence A may be less than or equal to about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C. In some embodiments, a second melting temperature of a nucleic acid sequence B may be less than a first melting temperature of a priming region by about 1° C. to about 80° C., from about 5° C. to about 30° C., or from about 10° C. to about 20° C. In some embodiments, a third melting temperature of a nucleic acid sequence A may be less than a first melting temperature of a priming region and/or a second melting temperature of a nucleic acid sequence B by about 1° C. to about 80° C., from about 5° C. to about 30° C., or from about 10° C. to about 20° C.

A cleavable moiety of a priming region of an inactivatable priming oligonucleotide may be any suitable cleavable moiety for an inactivatable priming oligonucleotide, including examples described elsewhere herein (e.g., ribose). In some embodiments, an inactivatable priming oligonucleotide may comprise a plurality of cleavable moieties. Moreover, a cleavable moiety of a priming region of an inactivatable priming oligonucleotide may be cleaved by any suitable method. For example, a cleavable moiety of a priming region of an inactivatable priming oligonucleotide may be cleaved with one or more of the use of an enzyme (e.g., an endonuclease including example endonucleases described elsewhere herein, such as RNase HI, RNase HII, RNase HIII, nicking restriction endonucleases, Nb, BbvCI, NtAlwI, NbBsmI, BsaI, SapI, NbBsrDI), with the use of light, with the use of a reducing agent (e.g., DTT or TCEP) and with the use of a solution pH that is greater than 7 (e.g., an alkaline solution). In some embodiments, an inactivatable priming oligonucleotide may be a loop inactivatable priming oligonucleotide as described elsewhere herein.

Figure 9A:
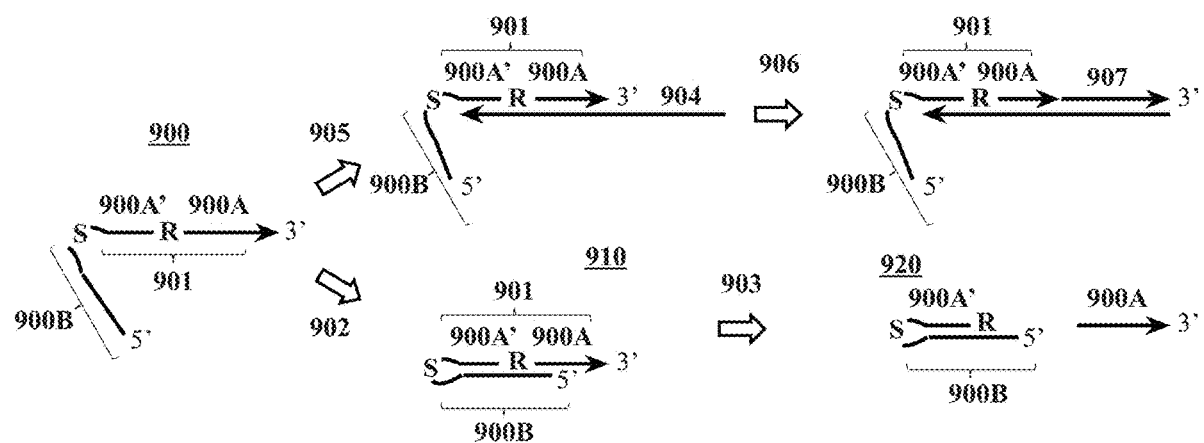
FIG. 9A schematically depicts an example inactivatable priming oligonucleotide and its function in an amplification reaction.

An example of an inactivatable priming oligonucleotide, an example method for nucleic acid amplification with such an inactivating priming oligonucleotide and an example method for inactivating the inactivatable priming oligonucleotide are schematically depicted in FIG. 9A. As shown in FIG. 9A, inactivatable priming oligonucleotide 900 includes, from 3' to 5', a nucleic acid sequence 900A, a cleavable moiety (e.g., ribose R), a nucleic acid sequence 900A' and a nucleic acid sequence 900B. Nucleic acid sequences 900A and 900A' and the cleavable moiety R are included in a priming region 901 of the priming oligonucleotide. Nucleic acid sequence 900B is complementary to the priming region 901 and non-complementary to the single-stranded target nucleic acid molecule 904. Moreover, nucleic acid sequence 900B includes a spacer region S that is a sequence of nucleotides that is not complementary to priming region 901 or the single-stranded target nucleic acid molecule 904. The spacer S can prevent sequence 900B from functioning as a template in a nucleic acid amplification reaction via the action of a polymerase. Moreover, the melting temperature of nucleic acid sequence 900B is less than the melting temperature of the priming region 901.

As shown in FIG. 9A, at a temperature 902 equal to or below the melting temperature of nucleic acid sequence 900B, nucleic acid sequence 900B is hybridized to the priming region 901 resulting in the priming oligonucleotide adopting a loop oligonucleotide structure 910. The cleavable moiety R is cleaved 903 and nucleic acid sequence 900A is released from loop oligonucleotide 910 via cleavage 903 of the cleavable moiety R to generate an inactivated structure 920. Cleavage can be achieved via any suitable route, for example, via the action of an enzyme (e.g., a thermal stable and/or activatable enzyme having endonuclease activity, such as RNase HI, RNase HII or RNase HIII). Free nucleic acid sequence 900A does not stably hybridize with the single-stranded target nucleic acid molecule 904 at a temperature equal to or higher than its melting temperature. Thus, the priming region of the inactivatable priming oligonucleotide is inactivated.

As shown in FIG. 9A, at a temperature 905 that is equal to or higher than the melting temperature of nucleic acid sequence 900B, nucleic acid 900B denatures from priming region 901 and the priming region 901 can prime its complementary sequence on a single-stranded target nucleic acid molecule 904. As shown in FIG. 9A, nucleic acid sequences 900A' and 900A are complementary to the target nucleic acid molecule 904. Via the action of a polymerase, the single-stranded target nucleic acid molecule 904 can be extended 906 in a primer extension reaction to generate a nucleic acid product 907. Following generation of the nucleic acid product 907, the cleavable moiety R can be cleaved to remove nucleic acid sequences 900A' and 900B to generate a "sticky end" on the nucleic acid product 907.

Additional aspects of the disclosure provide activatable priming oligonucleotides and methods use of such primers in a nucleic acid amplification reaction. An activatable priming oligonucleotide can include a cleavable moiety and/or sequences with varied melting temperatures. Such activatable priming oligonucleotides can be activated via cleavage of the cleavable moiety and/or the manipulation of temperature.

Another aspect of the disclosure provides an activatable priming oligonucleotide. The activatable priming oligonucleotide can include a priming region having a nucleic acid sequence A that is hybridizable to a single-stranded target nucleic acid molecule and at least one cleavable moiety. The nucleic acid sequence A can have a 3' end that is adapted to be extended in a primer extension reaction to form a complement nucleic acid strand of the single-stranded target nucleic acid molecule only upon cleavage of the cleavable moiety. In addition, the activatable priming oligonucleotide can include a nucleic acid sequence B that is 3' to the priming region and exhibits sequence complementarity to the priming region.

An additional aspect of the disclosure provides an activatable priming oligonucleotide. The activatable priming oligonucleotide can include a priming region having a nucleic acid sequence A that is hybridizable to a single-stranded target nucleic acid molecule and at least one cleavable moiety. The nucleic acid sequence A can have a 3' end that is adapted to be extended in a primer extension reaction to form a complement nucleic acid strand of the single-stranded target nucleic acid molecule only upon cleavage of the cleavable moiety. In addition, the activatable priming oligonucleotide can include a nucleic acid sequence B that is 3' to the priming region. The priming region can have a first melting temperature and the nucleic acid sequence B can have a second melting temperature that is less than the first melting temperature.

An activatable priming oligonucleotide described herein may be a loop activatable priming oligonucleotide in that its sequence may comprise regions that are complementary to each other. Such regions of a loop activatable priming oligonucleotide can hybridize with one another to form a loop structure (e.g., hairpin structure) in the activatable priming oligonucleotide. For example, all or a portion of a nucleic acid sequence B may exhibit sequence complementarity to a priming region of an activatable priming oligonucleotide. Moreover, a nucleic acid sequence B may or may not be complementary to a single-stranded target nucleic acid molecule and/or a complement of the single-stranded nucleic acid molecule. In some embodiments, a nucleic acid sequence B may be at least partially complementary to a complement of a target nucleic acid molecule.

In some embodiments, a nucleic acid sequence B may comprise a spacer that is not complementary to a priming region and/or a single-stranded target nucleic acid molecule. Such a spacer may be a region of the activatable priming oligonucleotide that cannot be copied via a polymerase during a primer extension reaction. For example, the spacer may be a sequence of one, two, three, four, five, six, seven, eight, nine, ten, eleven, twelve, thirteen, fourteen, fifteen, sixteen, seventeen, eighteen, nineteen, twenty or more nucleotides. Such a sequence of oligonucleotides may comprise one or more species that inhibits the action of a polymerase with non-limiting examples that include dSpacer (abasic furan), Spacer C3, hexanediol spacer, Spacer 9, Spacer 12 and Spacer 18.

In embodiments, a priming region of an activatable priming oligonucleotide may include, from 5' to 3', a nucleic acid sequence A, a cleavable moiety and a nucleic acid sequence A'. A nucleic acid sequence A' may or may not be complementary to a single-stranded target nucleic acid molecule. In some embodiments, a priming region of an activatable priming oligonucleotide can have a first melting temperature and a nucleic acid sequence B can have a second melting temperature that is less than the first melting temperature.

A first melting temperature of a priming region may be any suitable melting temperature. For example, a first melting temperature of a priming region may be from about 50° C. to about 80° C., from about 60° C. to about 75° C., or from about 65° C. to about 70° C. In some embodiments, a first melting temperature of a priming region may be at least about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or higher, or lower depending upon the particular activatable priming oligonucleotide.

A second melting temperature of a nucleic acid sequence B may be any suitable melting temperature and can be less than a first melting temperature of a priming region. For example, a second melting of a nucleic acid sequence B may be less than or equal to about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C. depending upon the particular activatable priming oligonucleotide. In some embodiments, a second melting temperature of a nucleic acid sequence B may be less than a first melting temperature of a priming region. For example, a second melting of a nucleic acid sequence B may be less than a first melting temperature of a priming region by about 1° C. to about 80° C., from about 5° C. to about 30° C., or from about 10° C. to about 20° C. In some embodiments, a second melting temperature of a nucleic acid sequence B may be less than a first melting temperature of a priming region by about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C.

In some embodiments, a priming region may comprise additional sequences to a nucleic acid sequence A. For example, a priming region may comprise a nucleic acid sequence A'. In such embodiments, upon cleavage of a cleavable moiety, a nucleic acid sequence A may have a third melting temperature that may be less than the melting temperature of the priming region as a whole and/or the melting temperature of a nucleic acid sequence B. A third melting temperature of a nucleic acid sequence A may be any suitable melting temperature and can be less than the first melting temperature and/or second melting temperature. In some embodiments, the third melting temperature may be less than the first melting temperature but higher than the second melting temperature. In some embodiments, a third melting temperature of a nucleic acid sequence A may less than or equal to about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70°

C., 71° C., 72° C., 73° C., 74° C., 75° C., 76° C., 77° C., 78° C., 79° C., 80° C. depending upon the particular activatable priming oligonucleotide. In some embodiments, a third melting temperature of a nucleic acid sequence A may be less than a first melting temperature of a priming region and/or a second melting temperature of a nucleic acid sequence B by about 1° C. to about 80° C., from about 5° C. to about 30° C., or from about 10° C. to about 20° C.

A cleavable moiety of a priming region of an activatable priming oligonucleotide may be any suitable species. In some embodiments, an activatable priming oligonucleotide may comprise a plurality of cleavable moieties. Non-limiting examples of cleavable moieties that can be included in a priming region of an activatable priming oligonucleotide include ribose, a disulfide linkage, a diazobenzene derivative (e.g., cleavable with $Na_2S_2O_4$), a hydrazone-based linker, a photocleavable spacer (e.g., PC spacer), a thermally cleavable imine base/isocyanate adduct, an azide containing linker, a levulinoyl ester-based linker and an allyl-linker. Moreover, a cleavable moiety of a priming region of an activatable priming oligonucleotide may be cleavable by any suitable route. For example, a cleavable moiety of a priming region of an activatable priming oligonucleotide may be photo cleavable (e.g., via exposure of the cleavable moiety to light), enzymatically cleavable (e.g., e.g., via the action of an enzyme such as an endonuclease, restriction enzyme, ribonuclease (e.g., RNase HI, RNase HII, RNase HII)) or chemically cleavable (e.g., via a reducing agent (e.g., DTT, TCEP), appropriate pH condition or other condition in a reaction mixture). In some embodiments, the cleavable moiety of a priming region of an activatable priming oligonucleotide may be cleavable at an alkaline pH.

In some embodiments, an activatable priming oligonucleotide may be included in a solution such as, for example, an amplification reaction mixture. Such a reaction mixture may include the activatable priming oligonucleotide, a single-stranded target nucleic acid molecule and any additional reagents suitable for amplification of the single-stranded target nucleic acid molecule, as described elsewhere herein. Additional examples of types of additional types of example solutions described elsewhere herein may also include an activatable priming oligonucleotide. For example, a solution comprising an activatable priming oligonucleotide may comprise an alkaline buffer.

An additional aspect of the disclosure provides a method for nucleic acid amplification. The method comprises providing a solution containing an activatable priming oligonucleotide comprising a priming region having a nucleic acid sequence A that is hybridizable to a single-stranded target nucleic acid molecule and at least one cleavable moiety. The activatable priming oligonucleotide also can include a nucleic acid sequence B that is 3' to the priming region and exhibits sequence complementarity to the priming region wherein. The nucleic acid sequence A can have a 3' end that is adapted to be extended in a primer extension reaction to form a complement nucleic acid strand of the single-stranded target nucleic acid molecule only upon cleavage of the cleavable moiety. The method further comprises cleaving the cleavable moiety and performing the primer extension reaction using the nucleic acid sequence A to form the complement nucleic acid strand.

Another aspect of the disclosure provides a method for nucleic acid amplification. The method comprises providing a solution containing an activatable priming oligonucleotide comprising a priming region having a nucleic acid sequence A that is hybridizable to a single-stranded target nucleic acid molecule and at least one cleavable moiety. The activatable priming oligonucleotide can also include a nucleic acid sequence B that is 3' to the priming region. The priming region can have a first melting temperature and the nucleic acid sequence B has a second melting temperature that is less than the first melting temperature. Moreover, the nucleic acid sequence A can have a 3' end that is adapted to be extended in a primer extension reaction to form a complement nucleic acid strand of the single-stranded target nucleic acid molecule only upon cleavage of the cleavable moiety. The method further comprises cleaving the cleavable moiety and performing the primer extension reaction using the nucleic acid sequence A to form the complement nucleic acid strand.

The solution in which activatable priming oligonucleotide activation takes place may be any suitable solution, including an amplification reaction mixture in which a single-stranded target nucleic acid molecule is amplified. In some embodiments, a priming region of an activatable priming oligonucleotide may include, from 5' to 3', a nucleic acid sequence A, a cleavable moiety and a nucleic acid sequence A'. A nucleic acid sequence A' may or may not be complementary to the single-stranded target nucleic acid molecule. Moreover, in some embodiments, a nucleic acid sequence B may or may not be complementary to a single-stranded target nucleic acid molecule and/or a complement of the single-stranded target nucleic acid molecule. In some embodiments, a priming region of an activatable priming oligonucleotide can have a first melting temperature and a nucleic acid sequence B can have a second melting temperature that is less than the first melting temperature.

In some embodiments, a priming region may comprise an additional sequence to a nucleic acid sequence A (e.g., a nucleic acid sequence A'). In such embodiments, upon cleavage of a cleavable moiety, a nucleic acid sequence A may have a third melting temperature that can be less than a first melting temperature of a priming region and, in some embodiments, lower or higher than a second melting temperature of a nucleic acid sequence B. In some embodiments, a method may further comprise, prior to cleavage of a cleavable moiety and/or performing a primer extension reaction, reducing the temperature of a solution to temperature to equal to or below a third melting temperature. Such a temperature reduction may aid in allowing a cleaved nucleic acid sequence A of an activatable priming oligonucleotide to anneal to a single-stranded target nucleic acid molecule for a primer extension reaction.

A first melting temperature of a priming region, a second melting temperature of a nucleic acid sequence B and, where appropriate a third melting temperature of a nucleic acid sequence A may be any suitable melting temperature. For example, a first melting temperature of a priming region may be at least about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or higher, or lower depending upon the particular activatable priming oligonucleotide. In some embodiments, a second melting temperature of a nucleic acid sequence B may be less than or equal to about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C. In some embodiments, a third melting temperature of a nucleic acid sequence A may be less than or equal to about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70°

C., 71° C., 72° C., 73° C., 74° C., 75° C., 76° C., 77° C., 78° C., 79° C., 80° C. In some embodiments, a second melting temperature of a nucleic acid sequence B may be less than a first melting temperature of a priming region by about 1° C. to about 80° C., from about 5° C. to about 30° C., or from about 10° C. to about 20° C. In some embodiments, a third melting temperature of a nucleic acid sequence A may be less than a first melting temperature of a priming region and/or a second melting temperature of a nucleic acid sequence B by about 1° C. to about 80° C., from about 5° C. to about 30° C., or from about 10° C. to about 20° C.

A cleavable moiety of a priming region of an activatable priming oligonucleotide may be any suitable cleavable moiety for an activatable priming oligonucleotide, including examples described elsewhere herein (e.g., ribose). In some embodiments, an activatable priming oligonucleotide may comprise a plurality of cleavable moieties. Moreover, a cleavable moiety of a priming region of an activatable priming oligonucleotide may be cleaved by any suitable method. For example, a cleavable moiety of a priming region of an activatable priming oligonucleotide may be cleaved with one or more of the use of an enzyme (e.g., an endonuclease including example endonucleases described elsewhere herein, such as RNase HI, RNase HII, RNase HIII, nicking restriction endonucleases, Nb, BbvCI, NtAlwI, NbBsmI, BsaI, SapI, NbBsrDI), with the use of light and with the use of solution pH that is greater than 7 (e.g., an alkaline solution). In some embodiments, an activatable priming oligonucleotide may be a loop activatable priming oligonucleotide as described elsewhere herein.

Figure 9B:
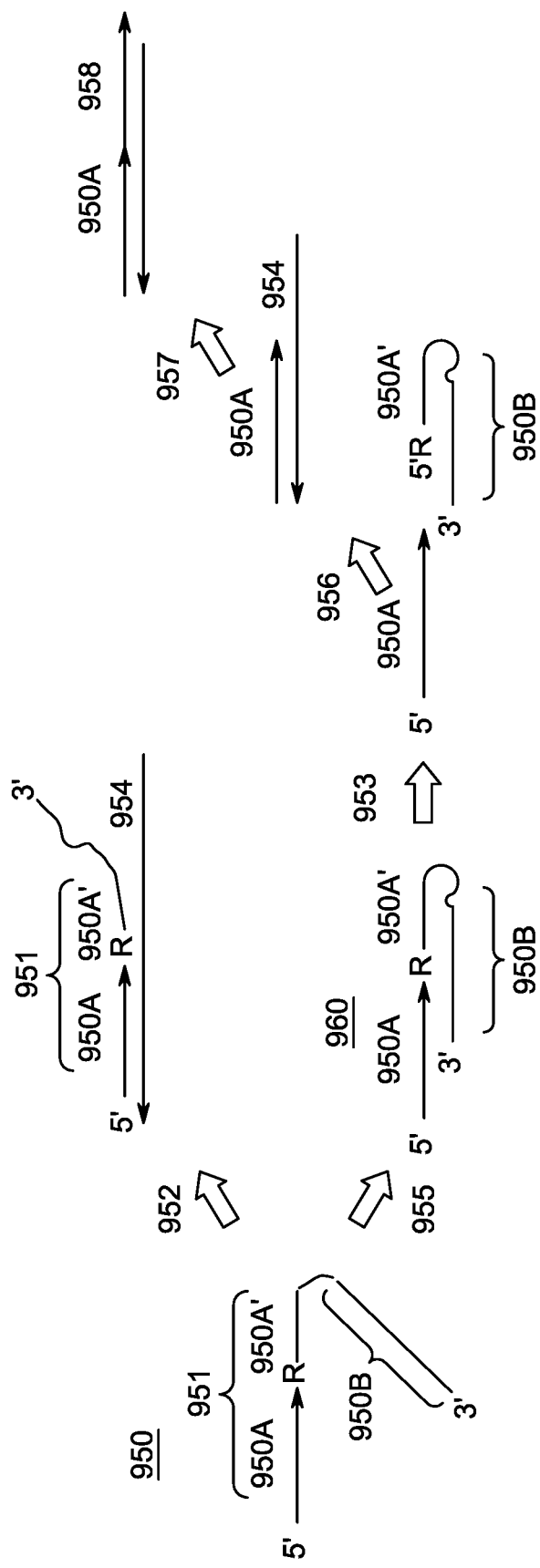
FIG. 9B schematically depicts an example activatable priming oligonucleotide and its function in an amplification reaction.

An example of an activatable priming oligonucleotide, activating such an activatable priming oligonucleotide and an example method for amplifying a single-stranded target nucleic acid molecule with the example activatable priming oligonucleotide are schematically depicted in FIG. 9B. As shown in FIG. 9B, activatable priming oligonucleotide 950 includes, from 5' to 3', a nucleic acid sequence 950A, a cleavable moiety (e.g., ribose R), a nucleic acid sequence 950A' and a nucleic acid sequence 950B. Nucleic acid sequences 950A and 950A' and the cleavable moiety R are included in a priming region 951 of the priming oligonucleotide. Nucleic acid sequence 950A' is not complementary to the single-stranded target nucleic acid molecule 954. Nucleic acid sequence 950B is complementary to the priming region 951 and non-complementary to the single-stranded target nucleic acid molecule 954. The melting temperature of nucleic acid sequence 950B is less than the melting temperature of the priming region 951.

As shown in FIG. 9B, at a temperature 952 that is equal to or higher than the melting temperature of nucleic acid sequence 950B, nucleic acid 950B denatures from priming region 951 and nucleic acid sequence 950A of the priming region 951 can prime its complementary sequence on a single-stranded target nucleic acid molecule 954. However, as nucleic acid sequences 950A' and 950B are non-complementary to the single-stranded target nucleic acid molecule 954, the 3' end of the priming region cannot be extended in a primer extension reaction via the action of a polymerase. Thus, without activation, the activatable priming oligonucleotide 950 cannot participate in an amplification reaction that amplifies the single-stranded target nucleic acid molecule 954.

As shown in FIG. 9B, at a temperature 955 equal to or below the melting temperature of nucleic acid sequence 950B, nucleic acid sequence 950B is hybridized to the priming region 951 resulting in the priming oligonucleotide adopting a loop oligonucleotide structure 960. The cleavable moiety R of the loop oligonucleotide 960 can be cleaved 953 and nucleic acid sequence 950A is released from loop oligonucleotide 960. Cleavage can be achieved via any suitable route, for example, via the action of an enzyme (e.g., a thermal stable enzyme and/or activatable enzyme having endonuclease activity, such as RNase HI, RNase HII or RNase HIII). Cleavage of the cleavable moiety R activates the priming oligonucleotide by releasing nucleic acid sequence 950A. As shown in FIG. 9B, at a temperature equal to or below its melting temperature, the free nucleic acid sequence 950A can prime 956 single-stranded target nucleic acid molecule 954. The annealed nucleic acid sequence 950A can then be extended 957 in a primer extension reaction to generate a nucleic acid product 958.

Additional aspects of the disclosure provide reaction mixtures comprising both activatable and inactivatable priming oligonucleotides and methods for using both activatable and inactivatable priming oligonucleotides in a series of amplification reactions. Such amplification reactions can occur in a single reaction mixture by modulating the conditions and/or reagents in the reaction mixture over the course of time. Amplification of a target nucleic acid molecule in the presence of activatable and inactivatable priming oligonucleotides can, in some embodiments, permit the completion of a nested amplification reaction. Such a nested amplification reaction can be performed in a single amplification reaction mixture or can be performed in a multiple amplification reaction mixtures.

An additional aspect of the disclosure provides a reaction mixture comprising an activatable priming oligonucleotide and an inactivatable priming oligonucleotide. The activatable priming oligonucleotide can comprise a priming region having a nucleic acid sequence A' that is hybridizable to the target nucleic acid molecule and at least one first cleavable moiety. The activatable priming oligonucleotide can become activated only upon cleavage of the first cleavable moiety, such that a 3' end of the nucleic acid sequence A' becomes extendable in a primer extension reaction to form a complement nucleic acid strand of the target nucleic acid molecule. The inactivatable priming oligonucleotide can comprise a priming region having a nucleic acid sequence A that is hybridizable to the target nucleic acid molecule and at least one second cleavable moiety. The inactivatable priming oligonucleotide can become inactivated upon cleavage of the second cleavable moiety, such that the nucleic sequence A does not form a stable complex with the target nucleic acid molecule to facilitate a primer extension reaction based on the target nucleic acid molecule sequence.

In some embodiments, the activatable priming oligonucleotide can further comprise a nucleic acid sequence B' that is 3' to the priming region of the activatable priming oligonucleotide and that exhibits sequence complementarity to the priming region of the activatable priming oligonucleotide. Similarly, in some embodiments, the inactivatable priming oligonucleotide can further comprise a nucleic acid sequence B adjacent to the priming region of the inactivatable priming oligonucleotide that exhibits sequence complementarity to the priming region of the inactivatable priming oligonucleotide.

The reaction mixture may also comprise the target nucleic acid molecule and may include any other reagents necessary (e.g., polymerase, endonuclease, co-factors, dNTPs, suitable buffer, additional primers, etc.) for amplifying the target nucleic acid molecule. Moreover, the reaction mixture may also include a detectable moiety that can be used to detect amplification products in the reaction mixture. In some embodiments, the first cleavable moiety and/or the second cleavable moiety may be cleavable by an enzyme. In some embodiments, the first cleavable moiety and the second cleavable moiety are cleavable by the same enzyme. Such and an enzyme may be any suitable enzyme (e.g., an endonuclease including example endonucleases described elsewhere herein, activatable enzyme (e.g., an activatable endonuclease)) and, thus, may also be included in the reaction mixture. In the case where an enzyme is an activatable enzyme, the enzyme may be initially provided in the reaction mixture and subsequently activated to cleave the first and/or second cleavable moieties. Moreover, the first and second cleavable moieties may be any suitable cleavable moiety including an example type of cleavable moiety described elsewhere herein. For example, the first and/or second cleavable moiety may be ribose.

The inactivatable priming oligonucleotide may be inactivatable upon cleavage of the first cleavable moiety of the activatable priming oligonucleotide. Similarly, the activatable priming oligonucleotide may be activatable upon cleavage of the second cleavable moiety of the inactivatable priming oligonucleotide. For example, the first cleavable moiety of the activatable priming oligonucleotide and the second cleavable moiety of the inactivatable priming oligonucleotide may be cleavable via the same cleavage method (e.g., via the same enzyme). Upon cleavage of the first cleavable moiety of the activatable priming oligonucleotide, the second cleavable moiety of the inactivatable priming oligonucleotide may also be cleaved. As described elsewhere herein, cleavage of the second cleavable moiety can inactivate the inactivatable priming oligonucleotide. Additionally, upon cleavage of the second cleavable moiety of the inactivatable priming oligonucleotide, the first cleavable moiety of the activatable priming oligonucleotide may also be cleaved. As described elsewhere herein, cleavage of the first cleavable moiety can activate the activatable priming oligonucleotide. In some embodiments, cleavage of the first and second cleavable moieties may be simultaneous or may be sequential. In some embodiments, an enzyme (an activatable endonuclease) may be activated or inactivated to inactivate the inactivatable primer and activate the activatable primer.

An additional aspect of the disclosure provides a method for nucleic acid amplification. The method comprises providing a solution comprising a target nucleic acid molecule, an activatable priming oligonucleotide and an inactivatable priming oligonucleotide and performing successive nucleic acid amplification reactions to yield amplified products of the target nucleic acid molecule. The successive nucleic acid amplification reactions can comprise at least a first phase followed by a second phase, where the first phase can comprise amplification of a target nucleic acid molecule using at least a portion of the inactivatable priming oligonucleotide as a primer, and where the second phase can comprise amplification of the target nucleic acid molecule or a region thereof using at least a portion of the activatable priming oligonucleotide as another primer. Moreover, the activatable priming oligonucleotide can be activated and the inactivatable priming oligonucleotide can be inactivated after the first phase.

In some embodiments, the activatable priming oligonucleotide can comprise a priming region having a nucleic acid sequence A' that is hybridizable to the target nucleic acid molecule and at least one cleavable moiety. The activatable priming oligonucleotide can also comprise a nucleic acid sequence B' that is 3' to the priming region of the activatable oligonucleotide and exhibits sequence complementarity to the priming region. The nucleic acid sequence A' can have a 3' end that is adapted to be extended in a primer extension reaction to form a complement nucleic acid strand of the target nucleic acid molecule only upon cleavage of the cleavable moiety.

In some embodiments, the inactivatable priming oligonucleotide can comprise a priming region having a nucleic acid sequence A that is hybridizable to the target nucleic acid molecule and at least one cleavable moiety. The inactivatable priming oligonucleotide can also include a nucleic acid sequence B adjacent to the priming region of the inactivatable priming oligonucleotide that exhibits sequence complementarity to the priming region. The nucleic acid sequence A can have a 3' end that is adapted to be extended in a primer extension reaction to form a complement nucleic acid strand of the target nucleic acid molecule. Furthermore, in some embodiments, the inactivatable priming oligonucleotide may be inactivatable upon cleavage of the first cleavable moiety of the activatable priming oligonucleotide as described elsewhere herein. Similarly, the activatable priming oligonucleotide may be activatable upon cleavage of the second cleavable moiety of the inactivatable priming oligonucleotide as described elsewhere herein. In some embodiments, the inactivatable priming oligonucleotide may be inactivatable simultaneously with activation of the activatable priming oligonucleotide.

In some embodiments, the successive nucleic acid amplification reactions can take place in a single reaction mixture. Alternatively, the successive nucleic acid amplification reactions can take place in more than one reaction mixture. Moreover, the solution may include any other reagents necessary (e.g., polymerase, endonuclease, co-factors, dNTPs, suitable buffer, additional primers, etc.) for amplifying the target nucleic acid molecule. Moreover, the solution may also include a detectable moiety that can be used to detect amplification products. In some embodiments, the solution comprises at least one reverse primer. Additionally, the activatable priming oligonucleotide and the inactivatable priming oligonucleotide may be activated and inactivated, respectively, by an enzyme. Such an enzyme may be included in the solution (or subsequently provided) and may be, for example, a thermal stable enzyme and/or an enzyme having endonuclease activity. Examples of enzymes having endonuclease activity are described elsewhere herein (e.g., an RNase, such as RNase HI, RNase HII or RNase HIII).

In some embodiments, the method further comprises detecting the amplified products of the target nucleic acid molecule. Detection of the amplified products may be via any suitable route including methods of detection described elsewhere herein. For example, the detection of the amplified products may be via optical detection, electrostatic detection or electrochemical detection. In some embodiments, a detectable moiety may aid in detection of amplified products.

An additional aspect of the disclosure provides a method for nucleic acid amplification. The method comprises providing a reaction mixture comprising a target nucleic acid molecule, an activatable priming oligonucleotide and an inactivatable priming oligonucleotide. Each of the activatable priming oligonucleotide and the inactivatable priming oligonucleotide can be hybridizable to a different region of the target nucleic acid molecule. The method further comprises, in the reaction mixture, selectively priming the target nucleic acid molecule with at least a portion of the activatable priming oligonucleotide or at least a portion of the inactivatable priming oligonucleotide. The method further comprises performing a nucleic amplification reaction using the target nucleic acid molecule selectively primed with at least a portion of the activatable priming oligonucleotide or at least a portion of the inactivatable priming oligonucleotide to yield an amplified product(s) of the target nucleic acid molecule.

In some embodiments, the target nucleic acid molecule can be selectively primed in the reaction mixture without removal of contents thereof. In some embodiments, selectively priming the target nucleic acid molecule with at least a portion of the activatable priming oligonucleotide can be effectuated by an enzyme that activates the activatable priming oligonucleotide to permit a primer extension reaction to yield the amplified product(s). Such an enzyme may be any suitable enzyme such as, for example, an enzyme with endonuclease activity as described elsewhere herein. Moreover, in some embodiments, selectively priming the target nucleic acid with at least a portion of the activatable priming oligonucleotide can be effectuated by an enzyme that inactivates the inactivatable priming oligonucleotide such that it does not form a stable complex with the target nucleic acid molecule. Such an enzyme may be any suitable enzyme such as, for example, an enzyme with endonuclease activity as described elsewhere herein.

In some embodiments, selectively priming the target nucleic acid molecule with the inactivatable priming oligonucleotide can be effectuated in the absence of an enzyme such as, for example, an enzyme with endonuclease activity as described elsewhere herein. In some embodiments, selectively priming the target nucleic acid molecule with the inactivatable priming oligonucleotide can be effectuated in the absence of an active enzyme such as, for example, an active (e.g., an activated) enzyme having endonuclease activity as described elsewhere herein. Such a condition can prevent inactivation of the inactivatable priming oligonucleotide.

Figure 10A:
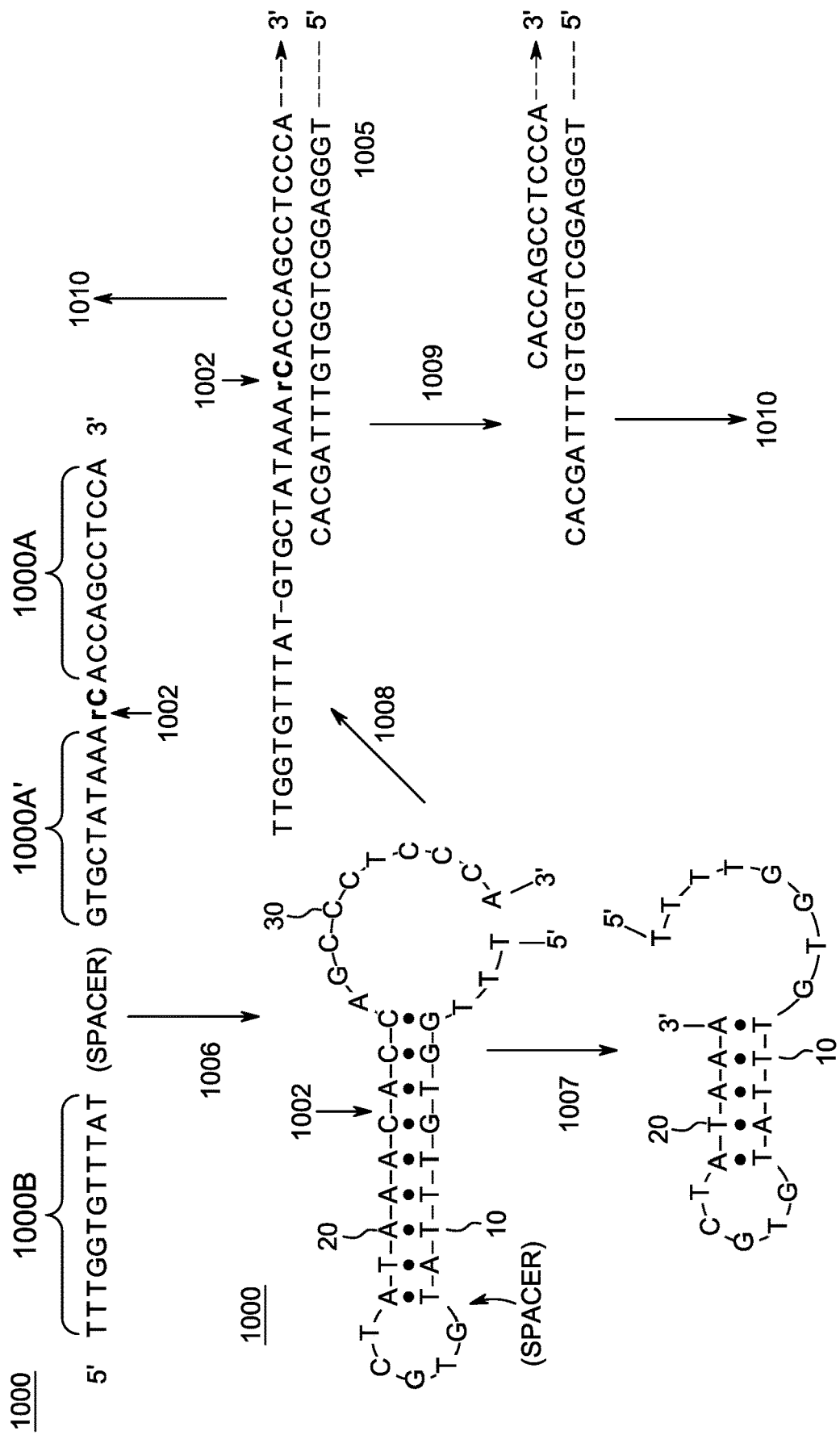
FIG. 10A schematically depicts an example inactivatable priming oligonucleotide and its function in an amplification reaction (FIG. 10A discloses SEQ ID NOS: 16-17, 16-19 and 18, respectively, in order of appearance)
Figure 10B:
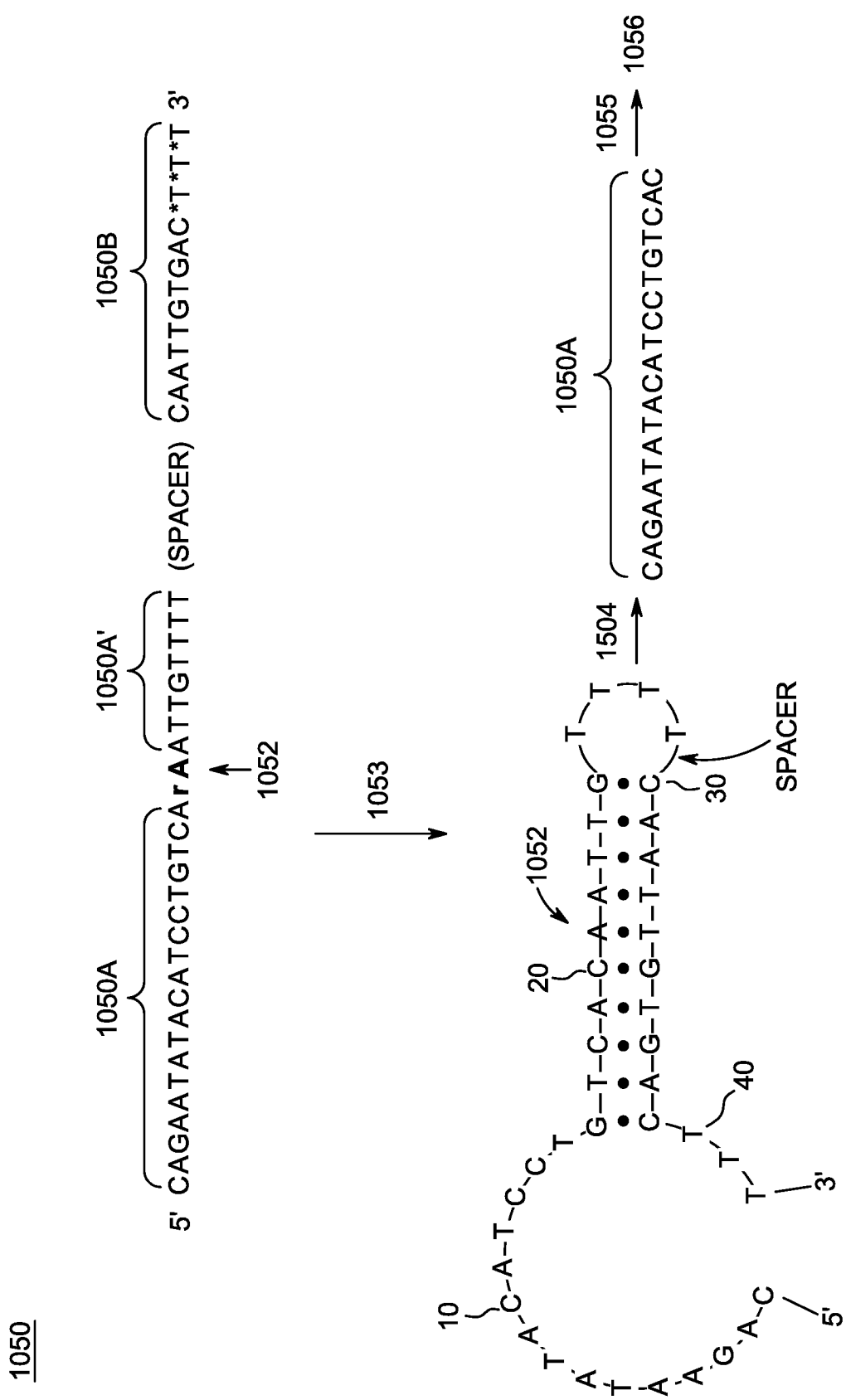
FIG. 10B schematically depicts an example activatable priming oligonucleotide and its function in an amplification reaction (FIG. 10B discloses SEQ ID NOS: 20-22, respectively, in order of appearance)
Figure 10C:
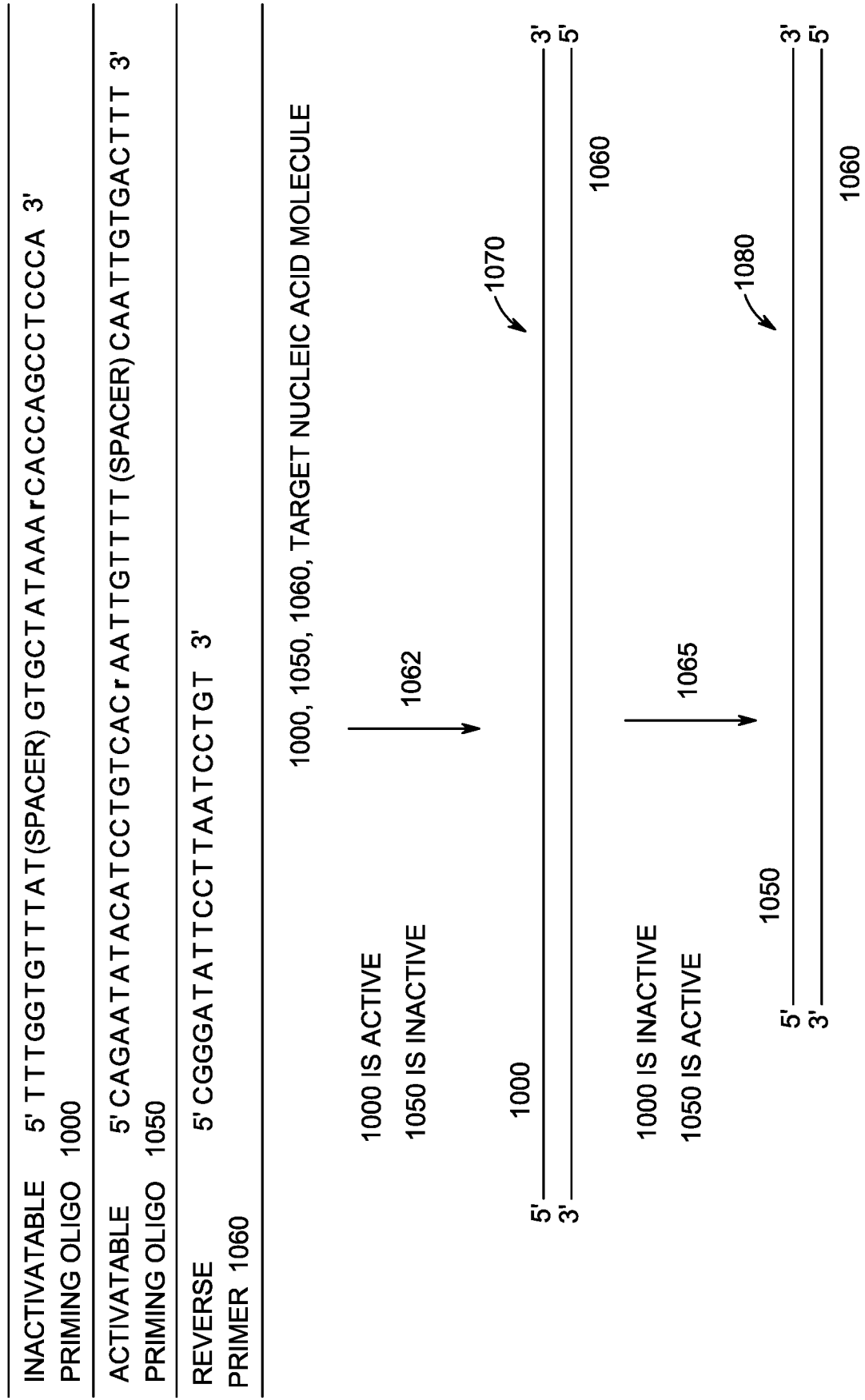
FIG. 10C provides a table summarizing the sequences of the example inactivatable and example activatable priming oligonucleotides depicted in FIG. 10A and 10B (FIG. 10C discloses SEQ ID NOS: 16-17, 20-21 and 23, respectively, in order of appearance)

Examples of activatable and inactivatable priming oligonucleotides along with their example use in a single-reaction mixture, nested amplification reaction are schematically depicted in FIG. 10A-10C. FIG. 10A schematically depicts an inactivatable priming oligonucleotide 1000 that comprises, from 3' to 5', a nucleic acid sequence 1000A, cleavable moiety 1002 (e.g., a ribose moiety "rC"), a nucleic acid sequence 1000A' and a nucleic acid sequence 1000B. The priming region of the inactivatable priming oligonucleotide 1000 includes nucleic acid sequence 1000A, cleavable moiety 1002 and nucleic acid sequence 1000A'. The nucleic acid sequence 1000B includes a spacer region and is not complementary to the target nucleic acid molecule 1005. The spacer region of nucleotide sequence 1000B is not complementary to itself or the priming region. Moreover, the nucleotide sequence 1000B is at least partially complementary to the priming region.

At a temperature 1008 that is equal to or above the melting temperature of nucleic acid sequence 1000B (e.g., approximately 60° C. for nucleic acid sequence 1000B shown in FIG. 10A), the inactivatable priming oligonucleotide 1000 can adopt a linear configuration. The linear inactivatable priming oligonucleotide can prime a single-stranded target nucleic acid molecule 1005 and participate in a primer extension reaction upon appropriate temperature conditions. The primer extension reaction can generate an amplified product of the single stranded target nucleic acid molecule 1005. The amplification products comprise a single-stranded region at a 5' end that corresponds to nucleic acid sequence 1000B. Such a single-stranded region may be useful as a "sticky end" in a downstream hybridization event (e.g., immobilization to an array, etc.) 1010. Alternatively, the amplified product can be further processed by cleaving 1009 the cleavable moiety 1002 to generate a single-stranded region at a 3' end that may also be useful as a "sticky end" in a downstream hybridization event 1010. In some embodiments, cleavage may be via an enzyme, such as an enzyme with endonuclease activity (e.g., an RNase such as RNase HII or RNase HIII).

At a temperature 1006 that is equal to or below the melting temperature of nucleic acid sequence 1000B, the inactivatable priming oligonucleotide 1000 adopts a loop oligonucleotide configuration. In its loop oligonucleotide configuration, the cleavable moiety 1002 of inactivatable priming oligonucleotide can be cleaved 1007 to release nucleic acid sequence 1000A and inactivate inactivatable priming oligonucleotide 1000. In some embodiments, cleavage may be via an enzyme, such as an enzyme with endonuclease activity (e.g., an RNase such as RNase HII or RNase HIII, an activatable endonuclease). The released nucleic acid sequence 1000A does not stably hybridize with the single-stranded target nucleic acid molecule 1000 at a temperature equal to or higher than its melting temperature.

An amplification reaction mixture can include inactivatable priming oligonucleotide 1000 and can be subject to appropriate conditions such that primer functionality of the inactivatable priming oligonucleotide 1000 is active. Amplification via the inactivatable priming oligonucleotide can proceed for a desired number of cycles and/or to a point where a desired amount of amplified product is generated. At that point, the inactivatable priming oligonucleotide 1000 can be inactivated by bringing the reaction mixture to appropriate temperature condition (e.g., a temperature at or below the melting temperature of nucleic acid sequence 1000B) and cleavage conditions (e.g., activation of an activatable endonuclease, to inactivate the inactivatable priming oligonucleotide 1000 from participating in further rounds of amplification.

FIG. 10B schematically depicts an activatable priming oligonucleotide 1050 that comprises, from 5' to 3', a nucleic acid sequence 1050A, cleavable moiety 1052 (e.g., a ribose moiety "rA"), a nucleic acid sequence 1050A' and a nucleic acid sequence 1050B. The priming region of the activatable priming oligonucleotide 1050 includes nucleic acid sequence 1050A, cleavable moiety 1052 and nucleic acid sequence 1050A'. The nucleic acid sequences 1050A' and 1050B are not complementary to the target nucleic acid molecule (not shown) and are separated by a spacer region. The spacer region is not complementary to itself. Moreover, nucleotide sequence 1050B is at least partially complementary to the priming region.

At a temperature that is equal to or above the melting temperature of nucleic acid sequence 1050B' (e.g., approximately 70° C. for nucleic acid sequence 1050B shown in FIG. 10B), the activatable priming oligonucleotide 1050 can adopt a linear configuration. The linear activatable priming oligonucleotide can prime a single-stranded target nucleic acid molecule via its nucleic acid sequence 1050A. However, due to the presence of the non-complementary nucleic acid sequence 1050B and nucleic acid sequence 1050A' at the 3' end of the priming region, the priming region cannot be extended in a primer extension reaction. Thus, the activatable priming oligonucleotide is inactive.

At a temperature 1053 that is equal to or below the melting temperature of nucleic acid sequence 1050B, the activatable priming oligonucleotide 1050 adopts a loop oligonucleotide configuration. In its loop oligonucleotide configuration, the cleavable moiety 1052 of activatable priming oligonucleotide can be cleaved 1054 to release nucleic acid sequence 1050A and activate activatable priming oligonucleotide 1050. In some embodiments, cleavage may be via an enzyme, such as an enzyme with endonuclease activity (e.g., an RNase such as RNase HII or RNase HIII, an activatable endonuclease). At a temperature at or below its melting temperature, the released nucleic acid sequence 1050A can hybridize with a single-stranded target nucleic acid molecule (not shown) and function as a primer in a primer extension reaction. Extension 1055 of the 3' end of hybridized nucleic acid sequence 1050A in a primer extension reaction can generate an amplified product 1056 of the single stranded target nucleic acid molecule.

An amplification reaction mixture can include activatable priming oligonucleotide 1050 and can be subject to appropriate conditions such that primer functionality of the activatable priming oligonucleotide 1050 is activated. Amplification via the activatable priming oligonucleotide can proceed for a desired number of cycles and/or to a point where a desired amount of amplified product is generated.

FIG. 10C schematically depicts an example nested amplification reaction using inactivatable priming oligonucleotide 1000 and activatable priming oligonucleotide 1050 to amplify a target nucleic acid molecule in a single reaction mixture. The linear sequences of inactivatable priming oligonucleotide 1000 and activatable priming oligonucleotide 1050 are shown in the table in FIG. 10C. The sequence of an example reverse primer 1060 used with both priming oligonucleotides is also shown in the table. The priming region of inactivatable priming oligonucleotide 1000 is complementary to a region of the target nucleic acid molecule that is 5' to the region of the target nucleic acid molecule to which the nucleic acid sequence 1050A of activatable priming oligonucleotide 1050 is complementary. Thus, the priming region of inactivatable priming oligonucleotide 1000 can be considered a forward "outer" primer and the nucleic acid sequence 1050A of the activatable priming oligonucleotide 1050 can be considered a forward "inner" primer.

Inactivatable priming oligonucleotide 1000, activatable priming oligonucleotide 1050, reverse primer 1060 and a target nucleic acid molecule can be provided in a reaction mixture in addition to any other reagents (e.g., polymerase, endonuclease, dNTPs, co-factors, suitable buffer, etc.) necessary for amplifying the target nucleic acid molecule. The target nucleic acid molecule can be amplified in successive amplification reactions. In a first phase of the successive amplification reactions, inactivatable priming oligonucleotide 1000 is active and can selectively prime its target sequence on a strand of the target nucleic acid molecule. Along with reverse primer 1060, the target nucleic acid molecule can be amplified 1062 in one or more amplification cycles via inactivatable priming oligonucleotide 1000 (as shown in FIG. 10A) to generate a first amplified product 1070.

After a desired number of amplification cycles and/or when a desired amount of the first amplified product 1070 is generated, an enzyme (e.g., an enzyme with endonuclease activity, such as, for example, RNase HI, RNase HII or RNase HIII, an activatable enzyme with endonuclease activity) can be added 1065 to the reaction mixture or activated in the reaction mixture (in cases where it is included in the initial reaction mixture) to cleave the cleavable moiety 1002 of inactivatable priming oligonucleotide 1000 and cleave the cleavable moiety 1052 of activatable priming oligonucleotide 1050. Cleavage of cleavable moiety 1002 inactivates priming oligonucleotide 1000 such that it can no longer participate in amplification of the target nucleic acid molecule as shown in FIG. 10A. Moreover, cleavage of cleavable moiety 1052 activates activatable priming oligonucleotide 1050 such that its nucleic acid sequence 1050A can amplify the target nucleic acid molecule as shown in FIG. 10B. Along with reverse primer 1060, the target nucleic acid molecule can be amplified 1065 in one or more amplification cycles via activated activatable priming oligonucleotide 1050 (as shown in FIG. 10B) to generate a second amplified product 1080. The second amplified product 1080 is shorter in length than the first amplified product 1070 as the nucleic acid sequence 1050A of the activatable priming oligonucleotide functions as an "inner" primer. In some embodiments, the reaction mixture may also include a detectable moiety that can be used to detect first amplification products 1070 and/or second amplification products 1080. In some embodiments, detection of the first amplification products 1070 and second amplification products 1080 may be achieved, for example, via gel electrophoresis or other suitable detection modality described herein.

In general, nucleic acid amplification may occur in a reaction mixture in which the nucleic acid molecule to be amplified is provided along with any additional reagents (e.g., forward primers, reverse primers, polymerases, dNTPs, co-factors, suitable buffers, etc.) necessary for amplification of the nucleic acid molecule. The reaction mixture may then be subjected to conditions (e.g., appropriate temperatures, addition/removal of heat, buffer concentrations, etc.) suitable for amplifying the nucleic acid molecule. For example, a single or double-stranded target nucleic acid molecule may be provided in a reaction mixture that also comprises additional reagents (e.g., a forward primers and reverse primers described elsewhere herein, a polymerase, dNTPs, co-factors, buffers, any other enzymes (e.g., a reverse transcriptase to generate cDNA from RNA, a ligase, etc.) necessary for amplification of the single or double-stranded target nucleic acid molecule. In some embodiments, the temperature of the reaction mixture may be cycled repeatedly through a denaturation temperature (e.g., to denature, separate or melt double-stranded nucleic acid molecules into component nucleic acid strands), an annealing temperature (e.g., to anneal or hybridize a primer to each of the component nucleic acid strands) and an extension temperature (e.g., to extend or add nucleotides to the annealed primers in a primer extension reaction via the action of a polymerase) in order to amplify the single-stranded or double-stranded target nucleic acid molecule.

The cycling of the temperature of a reaction mixture may be achieved, for example, with the aid of any suitable thermocycler instrument or other type of device capable of cyclical heating, including for example, a convection-based heating device. In some embodiments, denaturation of a double-stranded nucleic acid molecule may be achieved via a denaturing agent, such as, for example an alkaline agent (e.g. sodium hydroxide (NaOH)).

In some cases, amplification of a nucleic acid may be achieved isothermally such as, for example, without a change in temperature of a reaction mixture. In some embodiments, a method for nucleic acid amplification described herein may be completed without cycling the temperature of an amplification reaction mixture. For example, multiple amplification cycles may be performed without cycling the temperature of a reaction mixture.

A nucleic acid amplification reaction can include the use and action of a polymerase. During a primer extension reaction, a polymerase can generally add, in template-directed fashion, nucleotides to the 3' end of a primer annealed to a single-stranded nucleic acid molecule. Any suitable polymerase may be used for a primer extension reaction, including commercially available polymerases. Non-limiting examples of polymerases include Taq polymerase, Tth polymerase, Tli polymerase, Pfu polymerase, VENT polymerase, DEEPVENT polymerase, EX-Taq polymerase, LA-Taq polymerase, Expand polymerases, Sso polymerase, Poc polymerase, Pab polymerase, Mth polymerase, Pho polymerase, Phusion polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof.

In some embodiments, a suitable denaturation temperature may be, for example, about 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 93° C., 94° C., 95° C., 96° C., 97° C., 98° C., 99° C., 100° C., 101° C., 102° C., 103° C., 104° C., 105° C. or higher. In some embodiments, a suitable denaturation time for a single amplification cycle may be, for example, about 0.1 seconds ("s"), 0.5 s, 1 s, 2 s, 3 s, 4 s, 5 s, 6 s, 7 s, 8 s, 9 s, 10 s, 11 s, 12 s, 13 s, 14 s, 15 s, 16 s, 17 s, 18 s, 19 s, 20 s, 21 s, 22 s, 23 s, 24 s, 25 s, 26 s, 27 s, 28 s, 29 s, 30 s, 31 s, 32 s, 33 s, 34 s, 35 s, 36 s, 37 s, 38 s, 39 s, 40 s, 41 s, 42 s, 43 s, 44 s, 45 s, 46 s, 47 s, 48 s, 49 s, 50 s, 51 s, 52 s, 53 s, 54 s, 55 s, 56 s, 57 s, 58 s, 59 s, 1 minute, 2 minutes, 3 minutes, 4 minutes, 5 minutes or longer.

In some embodiments, a suitable annealing temperature may be, for example, about 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or higher. In some embodiments, an annealing temperature may be at ambient temperature (e.g., room temperature). In some embodiments, a suitable annealing time for a single amplification cycle may be, for example, about 0.1 s, 0.5 s, 1 s, 2 s, 3 s, 4 s, 5 s, 6 s, 7 s, 8 s, 9 s, 10 s, 11 s, 12 s, 13 s, 14 s, 15 s, 16 s, 17 s, 18 s, 19 s, 20 s, 21 s, 22 s, 23 s, 24 s, 25 s, 26 s, 27 s, 28 s, 29 s, 30 s, 31 s, 32 s, 33 s, 34 s, 35 s, 36 s, 37 s, 38 s, 39 s, 40 s, 41 s, 42 s, 43 s, 44 s, 45 s, 46 s, 47 s, 48 s, 49 s, 50 s, 51 s, 52 s, 53 s, 54 s, 55 s, 56 s, 57 s, 58 s, 59 s, 1 minute, 2 minutes, 3 minutes, 4 minutes, 5 minutes or longer.

In some embodiments, a suitable extension temperature may be, for example, about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or higher. In some embodiments, a suitable extension time for a single amplification cycle may be, for example, about 0.1 s, 0.5 s, 1 s, 2 s, 3 s, 4 s, 5 s, 6 s, 7 s, 8 s, 9 s, 10 s, 11 s, 12 s, 13 s, 14 s, 15 s, 16 s, 17 s, 18 s, 19 s, 20 s, 21 s, 22 s, 23 s, 24 s, 25 s, 26 s, 27 s, 28 s, 29 s, 30 s, 31 s, 32 s, 33 s, 34 s, 35 s, 36 s, 37 s, 38 s, 39 s, 40 s, 41 s, 42 s, 43 s, 44 s, 45 s, 46 s, 47 s, 48 s, 49 s, 50 s, 51 s, 52 s, 53 s, 54 s, 55 s, 56 s, 57 s, 58 s, 59 s, 1 minute, 2 minutes, 3 minutes, 4 minutes, 5 minutes or longer.

Any suitable type of nucleic acid amplification reaction may be used to amplify a nucleic acid molecule. One example of a nucleic acid amplification reaction is a polymerase chain reaction (PCR) that relies on repeated cycles of primer annealing, primer extension and denaturing of amplified nucleic acid molecules as described above. Additional non-limiting examples of types of nucleic acid amplification reactions include reverse transcription, ligase chain reaction, nested amplification, multiplex amplification, helicase-dependent amplification, asymmetric amplification, rolling circle amplification, multiple displacement amplification (MDA); and variants of PCR that include real-time PCR, hot start PCR, inverse PCR, methylation-specific PCR, allele-specific PCR, assembly PCR, asymmetric PCR, miniprimer PCR, multiplex PCR, nested PCR, overlap-extension PCR, digital PCR, emulsion PCR, dial-out PCR, helicase-dependent PCR, nested PCR, thermal asymmetric interlaced PCR, and touchdown PCR.

In various aspects described herein, a method may comprise detecting one or more nucleic acid molecules described herein, such as, for example amplified products of a target nucleic acid molecule, double-stranded nucleic acid molecules, single-stranded nucleic acid molecules, target nucleic acid molecules, inactivatable priming oligonucleotides and activatable priming oligonucleotides. Detection of any type of nucleic acid molecule described herein may be achieved via any suitable detection method or modality. The particular type of detection method or modality used may depend, for example, on the particular species being detected, other species present during detection, whether or not a detectable moiety is present, the particular type of detectable moiety to-be-used and/or the particular application.

Non-limiting examples of detection methods include optical detection, spectroscopic detection, electrostatic detection and electrochemical detection. Accordingly, a nucleic acid molecule described herein may be detected by detecting signals (e.g., signals indicative of an optical property, a spectroscopic property, an electrostatic property or an electrochemical property of the nucleic acid molecule or an associated detectable moiety) that are indicative of the presence or absence of the nucleic acid molecule. Optical detection methods include, but are not limited to, visual inspection (e.g., detection via the eye, observing an optical property or optical event without the aid of an optical detector), fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, amperometry.

In some embodiments, detection of a nucleic acid molecule described herein may be achieved with the aid of a detectable moiety. A detectable moiety may be linked or coupled with a nucleic acid molecule, including covalently and non-covalently (e.g., including intercalation of a double-stranded nucleic acid molecule). Moreover, a detectable moiety may be included in a reaction mixture that is used for nucleic acid amplification, as described elsewhere herein. In some embodiments, a method for nucleic acid amplification described herein may include a real-time nucleic acid amplification reaction (e.g., real time PCR reaction) whereby amplification products are detected during or after the amplification of a nucleic acid molecule. Non-limiting examples of detectable moiety include optically-responsive species (e.g., optically-responsive dyes, optically-responsive oligonucleotide probes (e.g., TaqMan probes, TaqMan Tamara probes, TaqMan MGB probes, Lion probes, molecular beacons)) and radiolabels (e.g., $^{14}C$, $^{123}I$, $^{124}I$, $^{125}I$, $^{131}I$, $^{99m}Tc$, $^{35}S$, or $^{3}H$).

In some embodiments, a detectable moiety may be an optically-responsive dye. (e.g., a fluorescent dye) that generates (or fails to generate a signal) when subjected to the appropriate conditions. Non-limiting examples of dyes include SYBR green, SYBR blue, DAPI, propidium iodine, Hoeste, SYBR gold, EvaGreen, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), SYBR Green, Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

Figure 12:
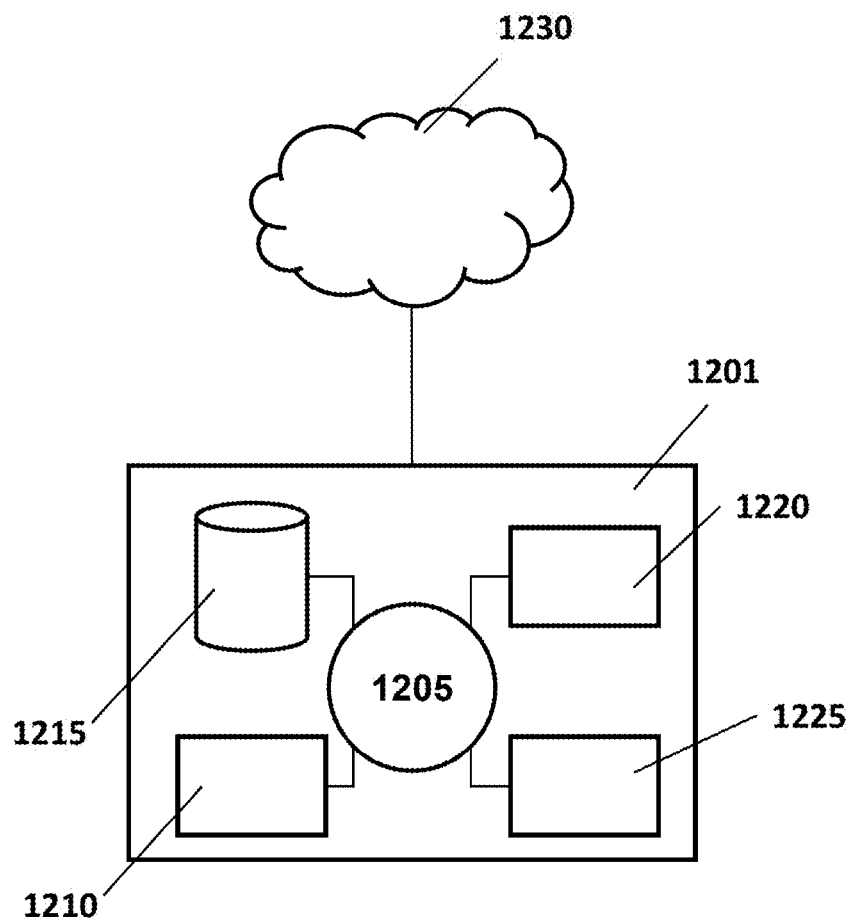
FIG. 12 schematically depicts an example computer system.

Methods described herein may be completed with the aid of a computer processor. In some embodiments, the computer processor may be included as part of a computer system. For example, as shown in FIG. 12, the computer processor 1205 (e.g., a central processing unit (CPU)) may be included as part of computer system 1201 and can be a single core or multi core processor, or a plurality of processors for parallel processing. The computer system 1201 can also include memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 (e.g., keyboards, mice, sounds systems, microphones, printers, or other input or output devices) can be in communication with the computer processor 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230, in some embodiments, may be a telecommunication and/or data network. The network 1230 can include one or more computer servers, which can enable distributed computing, such as cloud computing. The network 1230, in some embodiments with the aid of the computer system 1201, can implement a peer-to-peer network, which may enable devices coupled to the computer system 1201 to behave as a client or a server.

The computer processor 1205 can execute a sequence of machine-readable instructions, which can be embodied in a program or software. The instructions may be stored in a memory location, such as the memory 1210. Examples of operations performed by the computer processor 1205 can include fetch, decode, execute, and writeback. The storage unit 1215 can store files, such as drivers, libraries and saved programs. The storage unit 1215 can store programs generated by users and recorded sessions, as well as output(s) associated with the programs. The storage unit 1215 can store user data, e.g., user preferences and user programs. The computer system 1201, in some embodiments, can include one or more additional data storage units that are external to the computer system 1201, such as an additional storage unit that is located on a remote server that is in communication with the computer system 1201 through an intranet or the Internet.

The computer system 1201 can communicate with one or more remote computer systems through the network 1230. For instance, the computer system 1201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1201 via the network 1230. In some embodiments, a remote computer system can be operated by a battery that can be charged wirelessly. Communication with a remote computer system may be achieved, for example, wirelessly (e.g., via Wi-Fi, WiMAX, Bluetooth, light or microwave).

Methods described herein and instructions for operating the detection cell, detector and any other component of the system (e.g., pumps) can be implemented by way of machine (e.g., computer processor) executable code stored on an electronic storage location of the computer system 1201, such as, for example, on the memory 1210 or electronic storage unit 1215. The machine executable or machine readable code can be provided in the form of software. During use, the code can be executed by the processor 1205. In some embodiments, the code can be retrieved from the storage unit 1215 and stored on the memory 1210 for ready access by the processor 1205. In some situations, the electronic storage unit 1215 can be precluded, and machine-executable instructions are stored on memory 1210. The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

EXAMPLES

Example 1: Testing of Example Probe

A single-stranded test probe was evaluated against four target nucleic acid molecules. The test probe is schematically depicted in FIG. 1A. As shown in FIG. 1A, the test probe included, from 5' to 3', a detectable moiety 101 (e.g., FAM fluorescent dye), a nucleotide sequence 100A, a cleavable moiety (e.g., a ribose moiety "rC") 102, a nucleic acid sequence 100B and a quencher 103 (e.g., ABkFQ quencher). The four target nucleic acid molecules PM, rM, r3M and 5Mr are schematically depicted in FIG. 1B. Target nucleic acid molecule PM included a sequence perfectly complementary to the test probe; target nucleic acid molecule rM included a single mismatch in its site corresponding to the cleavable moiety 102 of the probe; target nucleic acid molecule r3M included two mismatches—one in its site corresponding to the cleavable moiety 102 of the probe and one 3' of the first mismatch; and target nucleic acid molecule 5Mr included two mismatches—one in its site corresponding to the cleavable moiety 102 of the probe and one 5' of the first mismatch.

In a first set of eight experiments, the probe was evaluated against the various target nucleic acid molecules ("DS") and a no template control ("SS") in varied concentrations of EDTA. A summary of the various reaction mixtures is tabulated in FIG. 2A. Each reaction mixture had a volume of 20 µL and included the test probe (0.1 µM), appropriate target nucleic acid molecule (0.1 µM), appropriate concentration of EDTA (1×EDTA=1.25 mM) along with a common reagent mixture. The common reagent mixture contained 1× Thermopol buffer (including 2 mM $MgCl_2$, pH 8.8) from New England Biolabs (NEB) and 50 mM $K_2SO_4$. The reaction mixtures did not include a polymerase or any other type of enzyme. The reaction mixtures were subject to a thermal cycling program of 10 cycles of 1 second ("s") denaturing at 98° C., 30 s annealing at 60° C. and 5 s extension at 72° C. After each cycle, the fluorescence of each reaction mixture was measured.

Figure 2B:
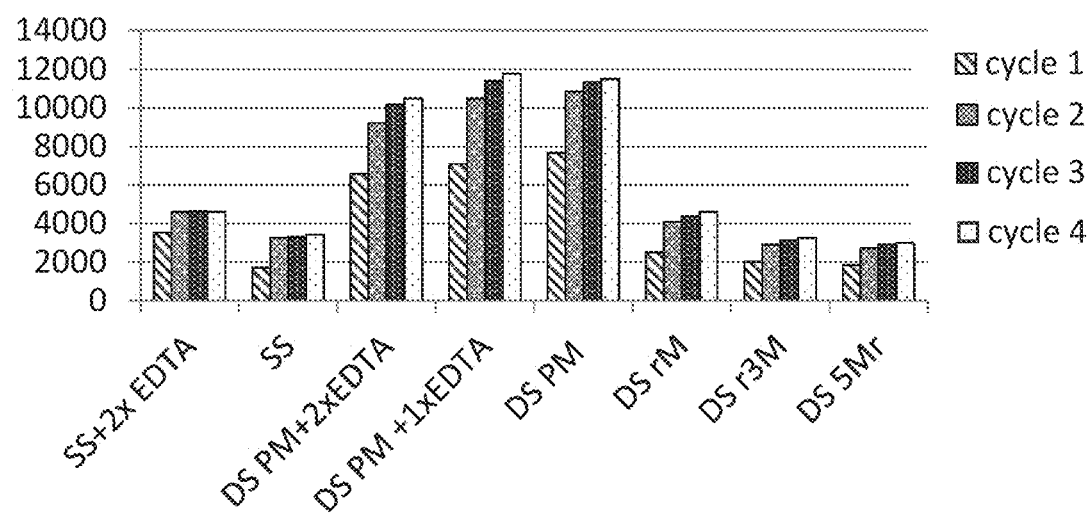
FIG. 2B is a bar chart graphically summarizing the results of various experiments described in Example 1.

The results of the first set of eight experiments is shown in FIG. 2B. As shown in FIG. 2B, fluorescent signals were higher when reaction mixtures included a target nucleic molecule and when a perfectly matching target nucleic acid molecule was used. Results shown in FIG. 2B suggest that hybridization of the probe with its target nucleic acid molecule to form a double-stranded complex can yield a higher signal. Moreover, results in FIG. 2B also suggest that a probe that binds a target nucleic acid molecule that does not include mismatches in and around its site corresponding to the cleavable moiety of the probe can yield higher signals.

In a second set of eight experiments, the probe was evaluated against varied concentrations of the PM target nucleic acid molecule at varied concentrations, at varied pH, with or without the presence of $MgCl_2$ and upon heating reaction mixtures to varied temperatures. A summary of the various reaction mixtures (1-8) is tabulated in FIG. 3B. Each reaction mixture had a volume of 20 µL and included the test probe (0.1 µM), PM target nucleic acid molecule (1×=0.1 µM) and $MgCl_2$ (at 2 mM where $MgCl_2$ was included) along with a common reagent mixture. The common reagent mixture contained 20 mM TrisHCl (at pH 7 or pH 9) and 50 mM $K_2SO_4$. The reaction mixtures did not include a polymerase or any other type of enzyme. The reaction mixtures were heated in a thermocycler to a temperature of either 60° C. or 70° C. Fluorescence of each reaction mixture was measured at multiple time points during heating.

Figures 3A, 3B:
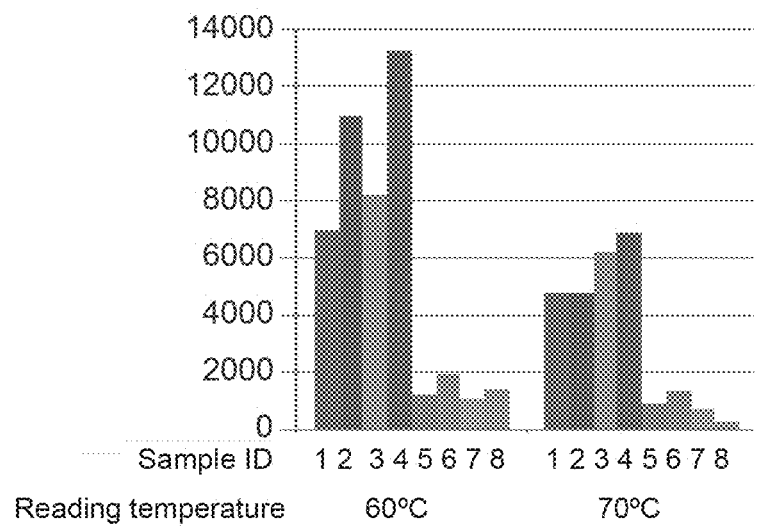
FIG. 3A is a table summarizing various experiments as described in Example 1.
FIG. 3B is a bar chart graphically summarizing the results of various experiments described in Example 1.

The results of the second set of experiments are shown in FIG. 3B. As shown in FIG. 3B, signals were higher when greater concentrations of target nucleic acid molecule were tested, at the higher pH condition of 9, where $MgCl_2$ was not present and at the lower heating temperature. Data in FIG. 3B suggest that signal can be target nucleic acid molecule concentration dependent, higher signals can be achieved at alkaline conditions and that divalent cations in a reaction mixture may be inhibitory.

In a third set of eight experiments, the probe was evaluated against the various target nucleic acid molecules at varied concentrations and at varied temperatures. A summary of the various reaction mixtures is tabulated in FIG. 4A. Each reaction mixture had a volume of 20 μL and included the test probe (0.1 μM), appropriate target nucleic acid molecule (1×=0.1 μM), along with a common reagent mixture. The common reagent mixture contained 1× Thermopol buffer (including 2 mM $MgCl_2$, pH 8.8) from New England Biolabs (NEB) and 50 mM $K_2SO_4$. The reaction mixtures did not include a polymerase or any other type of enzyme. The reaction mixtures were heated in a thermocylcer at 90° C. for 10 s and fluorescence of each reaction mixture measured. Afterwards, the temperature of the reaction mixtures was reduced by step reduction to temperatures of 70° C., 60° C., 45° C., 35° C. and 25° C. After each temperature reduction, the fluorescence of each reaction mixture was measured.

Figure 4B:
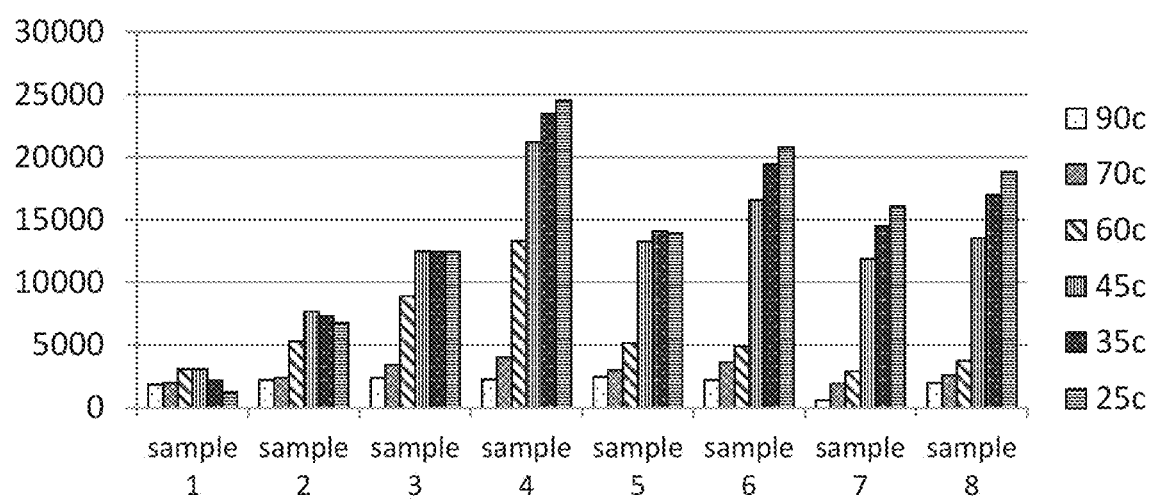
FIG. 4B is a bar chart graphically summarizing the results of various experiments described in Example 1.

The results of the third set of experiments is shown in FIG. 4B. As shown in FIG. 4B, fluorescent signal varied with temperature and also with the concentration of target nucleic acid molecule. Data in FIG. 4B suggest that signal can be target nucleic acid molecule concentration and temperature dependent.

Example 2: Testing of Example Probe

Figures 5A, 5B, 5C:
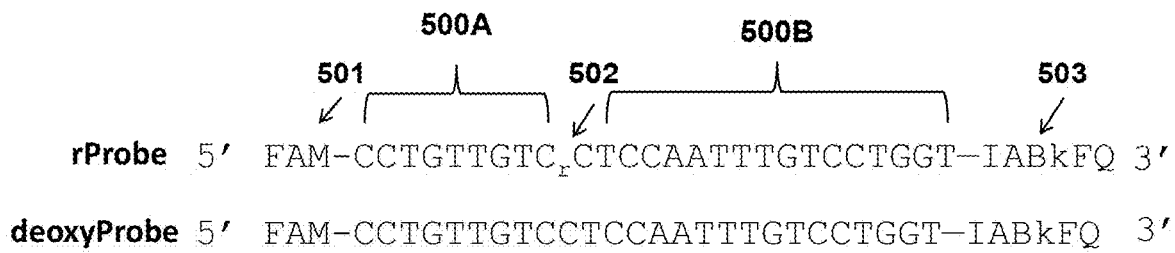
FIG. 5A schematically depicts example probes as described in Example 2 (FIG. 5A discloses SEQ ID NOS: 10-11, respectively in order of appearance)
FIG. 5B is a schematic depicting an example null probe as described in Example 2 (FIG. 5B discloses SEQ ID NO: 11)
FIG. 5C is a schematic depicting an example target nucleic acid molecule as described in Example 2 (FIG. 5C discloses SEQ ID NO: 12)

Two single-stranded test probes were evaluated against a target nucleic acid molecule. The first test probe ("rProbe") is schematically depicted in FIG. 5A. As shown in FIG. 5A, the test probe included, from 5' to 3', a detectable moiety 501 (e.g., FAM fluorescent dye), a nucleotide sequence 500A, a cleavable moiety (e.g., a ribose moiety "rC") 502, a nucleic acid sequence 500B and a quencher 503 (e.g., IABkFQ quencher). The second test probe ("deoxyProbe") was structurally the same as the first test probe, except that it did not comprise the cleavable moiety 502 and instead had a standard deoxy base at the same position as the cleavable moiety 502 of the first test probe. The target nucleic acid molecule is schematically depicted in FIG. 5C and was perfectly complementary to both test probes.

In a first set of 24 experiments, the first test probe was evaluated against different enzyme conditions (no enzyme (buffer only), Pfu polymerase, Phusion polymerase, 2× Phusion Master Mix, RNase HII, Pfu polymerase+RNase HII, Phusion polymerase+RNase HII, 2× Phusion Master Mix+RNase HII) without target nucleic acid molecule, with target nucleic acid molecule and with target nucleic acid molecule in the presence of a null probe (same probe as the "deoxyProbe" without a detectable moiety or quencher, schematically depicted in FIG. 5B). Each reaction mixture had a volume of 20 μL and included the first test probe (0.2 μM), target nucleic acid molecule if present (0.22 μM), null probe if present (0.22 μM), appropriate concentration of enzyme(s), along with a buffer. Where appropriate, the concentrations of the enzymes were as follows: Pfu=0.02 units/μL Phusion=0.02 units/μL and RNase HII=0.1 units/μL. The buffer contained 20 mM Tris-HCl, 10 mM $(NH_4)SO_4$, 10 mM KCl, 50 mM $K_2SO_4$, 2 mM $MgSO_4$, 0.1% Triton-X-100 at pH 8.8. The reaction mixtures were incubated at 37° C. for 15 min, then at 65° C. for 15 min, then subject to a thermal cycling program of 5 cycles 95° C. for 1 minute and 58° C. and 1 min. For reaction mixtures including the template nucleic acid molecule, the first test probe and target nucleic acid molecule were subject to a preliminary incubation at 55° C. for 5 min and then were cooled to 4° C. During the 58° C. phase of cycling, the fluorescence of each reaction mixture was measured.

Figure 6A:
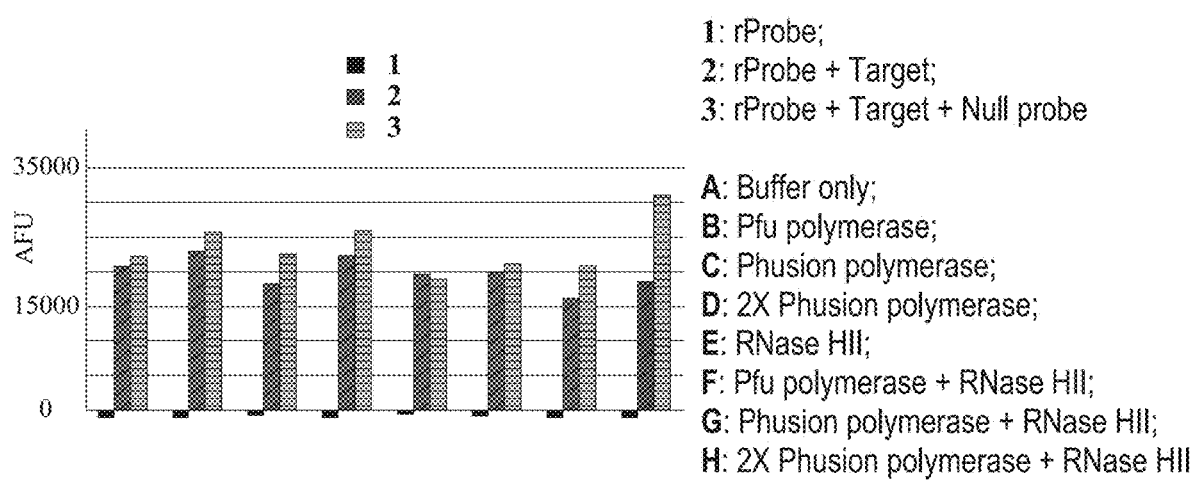
FIG. 6A and FIG. 6B are bar charts graphically summarizing the results of various experiments described in Example 2.

The results of the first set of experiments is shown in FIG. 6A. The data shown in FIG. 6A shows the average fluorescence signal (arbitrary fluorescence units) measured across the 5 cycles with correction/normalization of a reference dye (ROX 1×). Results for experiments including only the test probe (no target nucleic acid molecule) are indicated with "R" in the bar chart shown in FIG. 6A. Results for experiments including the test probe and target nucleic acid molecule (no null probe) are indicated with "R+T" in the bar chart FIG. 6A. Results for experiments including the test probe, target nucleic acid molecule and null probe are indicated with "R+T+N" in the bar chart in FIG. 6A. As shown in FIG. 6A, the signals are noticeably higher when the target nucleic acid molecule was included in reaction mixtures. Moreover, the presence of the null probe (as a competitor) did not appear to reduce observed signals. Data in FIG. 6A indicate that the first test probe can yield a signal when hybridized with a target nucleic acid molecule and that binding of the probe to the target nucleic acid molecule may be irreversible as the null probe did not appear to effect observed signal.

In a second set of 12 experiments, the first test probe and second test probe were evaluated against different enzyme conditions (no enzyme (buffer only), Phusion polymerase, RNase HII, Phusion 2× Master Mix, Taq Polymerase and Phusion 2× Mix+RNase HII) with target nucleic acid molecule. Each reaction mixture had a volume of 20 μL and included the appropriate test probe (0.2 μM), target nucleic acid molecule (0.22 μM), appropriate concentration of enzyme(s), along with a buffer. The concentrations of the enzymes were as follows Taq polymerase=0.075 units/μL, Phusion polymerase=0.02 units/μL and RNase HII=0.10 units/μL. The buffer for Phusion polymerase and RNase HII reactions contained 20 mM Tris-HCl, 10 mM $(NH_4)SO_4$, 10 mM KCl, 50 mM $K_2SO_4$, 2 mM $MgSO_4$, 0.1% Triton-X-100 at pH 8.8. The buffer for Taq polymerase reactions contained 1×Taq buffer from New England Biolabs. The reaction mixtures were incubated at 37° C. for 1 min, then at 65° C. for 1 min, then at 95° C. for 30 s, and the fluorescence of each reaction mixture measured at 60° C. Prior to incubations, test probe and target nucleic acid molecule were subject to a preliminary incubation at 55° C. for 5 min and then were cooled to 4° C.

Figure 6B:
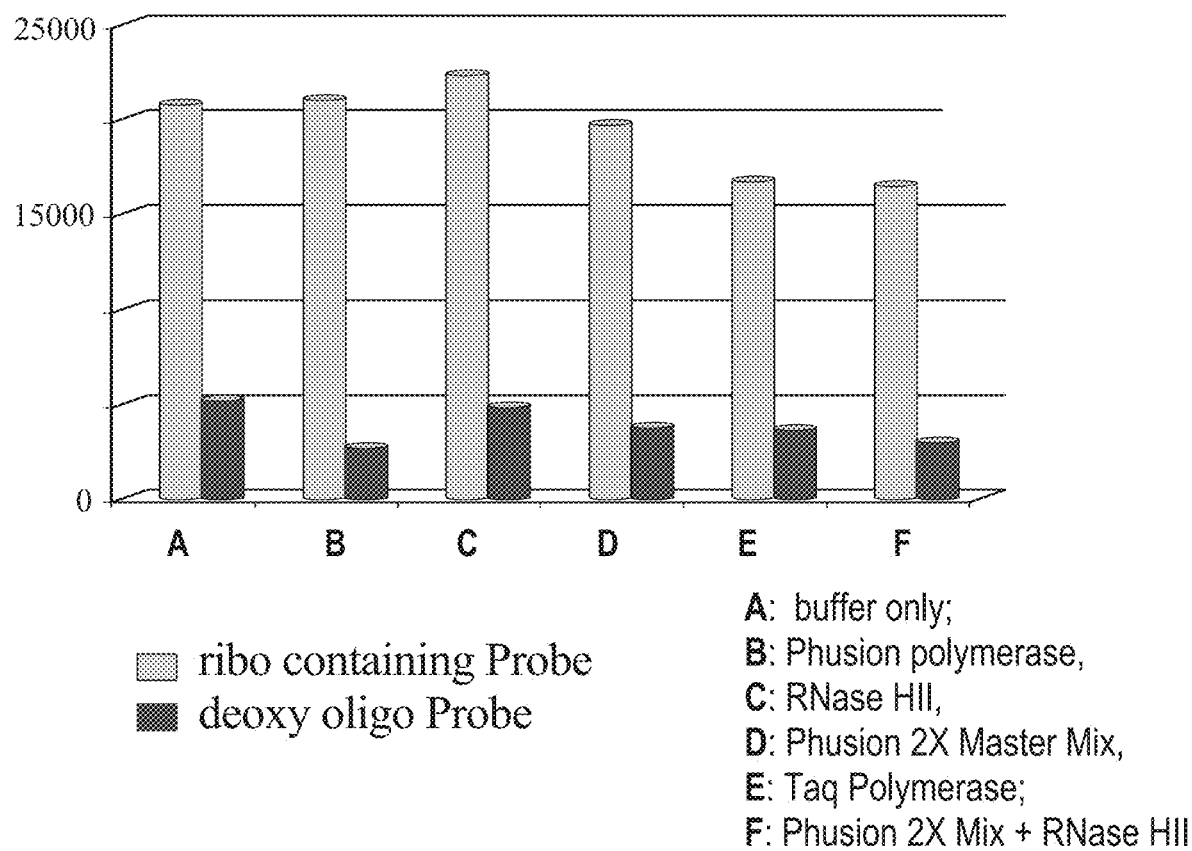

The results of the first set of experiments is shown in FIG. 6B. The data shown in FIG. 6B shows the fluorescence signal (arbitrary fluorescence units) measured across at 60° C. for each reaction mixture corrected/normalized to a reference dye (ROX 1×). As shown in FIG. 6B, the signals are noticeably higher for reaction mixtures containing the first test probe when compared to those containing the second test probe. Moreover, signals did not vary significantly for each probe tested despite the use of enzymes with different properties or even where an enzyme was not present (e.g., buffer only condition). Data in FIG. 6B suggest that the first test probe may yield a detectable signal in the absence of an enzyme and that functionality of the first test probe may not be dependent on the functionality of a particular type of enzyme (e.g., an enzyme with 3' or 5' exonuclease activity).

Example 3: Testing of Example Probes

Figure 7A:
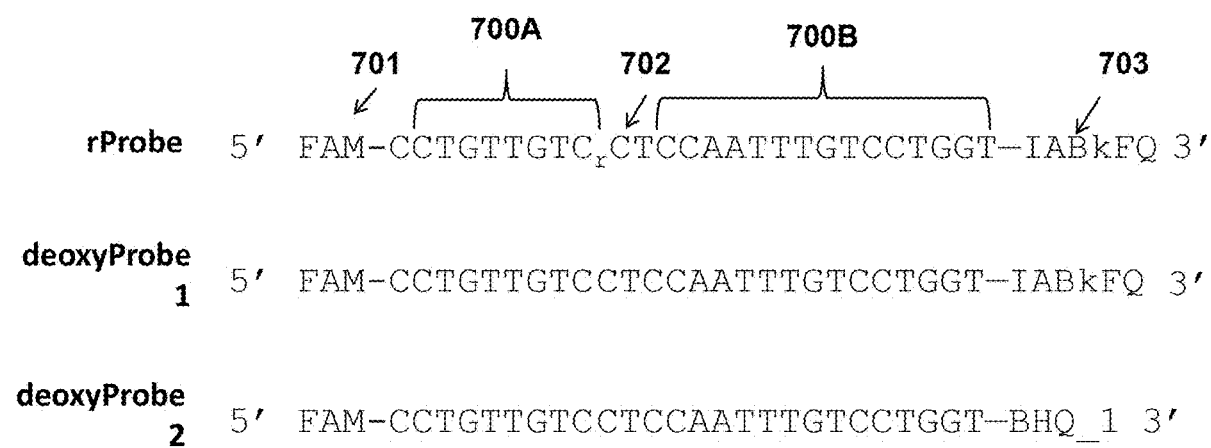
FIG. 7A schematically depicts example probes as described in Example 3 (FIG. 7A discloses SEQ ID NOS: 10-11 and 11, respectively in order of appearance)

Three test probes were evaluated against a target nucleic acid molecule. The three rest probes, "rProbe", "deoxyProbe1" and "deoxyProbe2" are schematically depicted in FIG. 7A. As shown in FIG. 7A, the rProbe test probe included, from 5' to 3', a detectable moiety 701 (e.g., FAM fluorescent dye), a nucleotide sequence 700A, a cleavable moiety (e.g., a ribose moiety "rC") 702, a nucleic acid sequence 700B and a quencher 703 (e.g., IABkFQ quencher). The deoxyProbe1 was structurally the same as the rProbe test probe, except that it did not comprise the cleavable moiety 702 and instead had a standard deoxy base at the same position as the cleavable moiety 702 of the rProbe. The deoxyProbe2 was structurally the same as the deoxyPRobe1 except that is had a BHQ 13 quencher instead of the IABkFQ quencher.

The three test probes were each provided to a 20 µL reaction mixture and evaluated in an amplification reaction of a target nucleic acid molecule. The reaction mixture included about 1000 copies of the target nucleic acid molecule; 0.3 µM of a forward primer (5'-GCA GTC CCA AAT CTC CAG TCA CTC A-3'(SEQ ID NO: 1)) and 0.3 µM of a reverse primer (5'-GGG CAA CAT ACC TTG ATA GTC CAG-3' (SEQ ID NO: 2)); 0.15 µM of deoxyProbe 1 or 2 or 0.1 µM of rProbe, 10 mM Tris-HCl, pH 8.3; 50 mM KCl; 1.5 mM MgCl$_2$; 0.2 mM dNTP mix; 1× reference Rox dye; and 0.0375 U/µL Taq polymerase. The amplification reactions were carried out in a real-time thermocycler, where the reaction mixture was preheated at 98° C. for 20 s, followed by 45 cycles of a temperature cycling program that included cycles of 95° C. for 7 s, 59° C. for 35 s and 72 C for 15 s. Signal in the reaction mixture was monitored during the 59° C. stage of each cycle of the temperature cycling program.

Figure 7B:
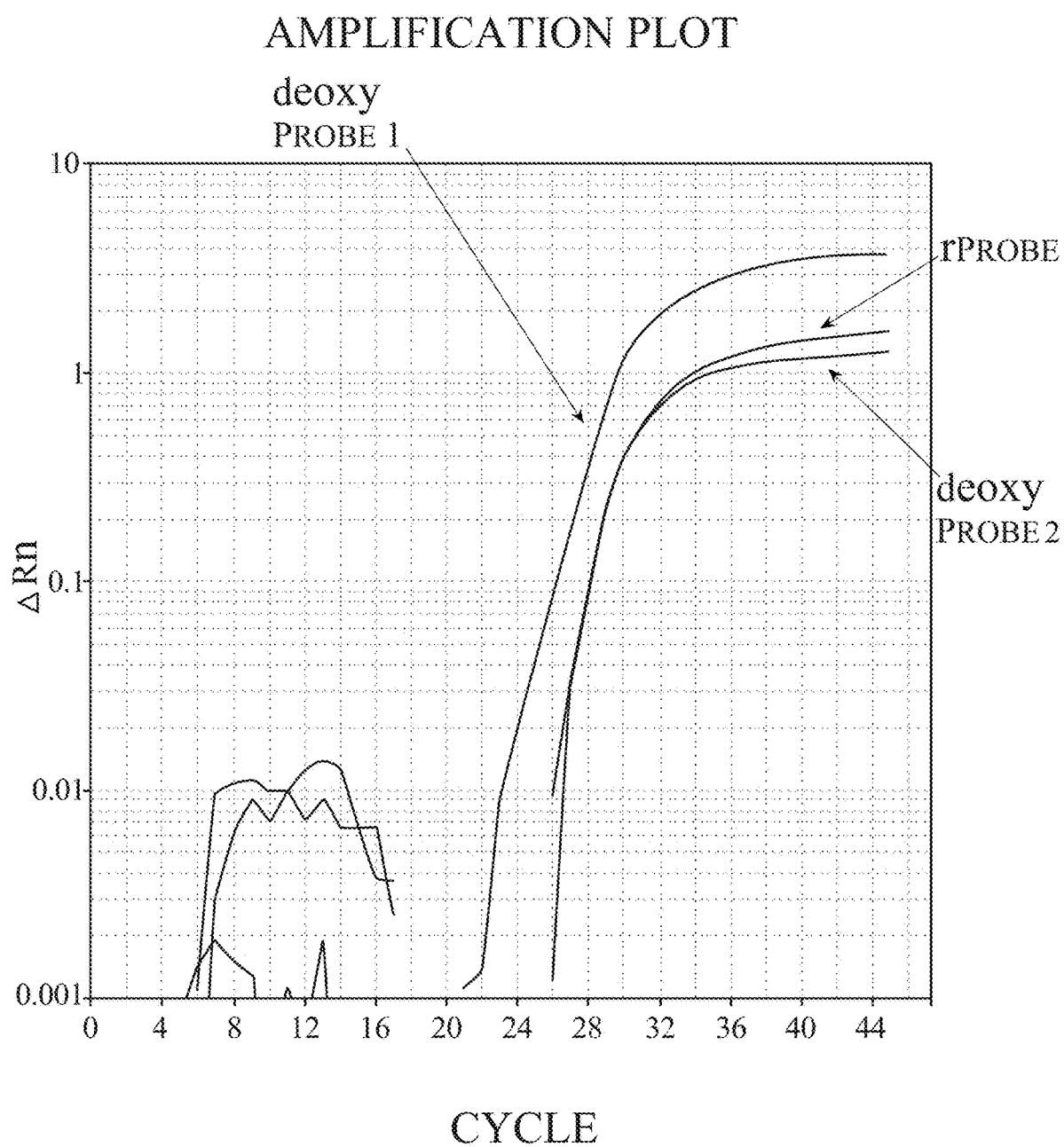
FIG. 7B graphically summarizes the results of various experiments described in Example 3.

The results of the experiments are shown in FIG. 7B. FIG. 7B depicts an amplification plot showing change in signal (ΔRn) vs cycle number at log scale. As shown in FIG. 7b, the rProbe test probe demonstrated similar performance as deoxyProbe2 in term of signal strength and signal conversion efficiency. As the amplification reactions were carried out in the presence of Taq polymerase, the data in FIG. 7B suggest that the rProbe test probe can function with similar efficiency as the deoxyProbe2 in the presence of a polymerase having 5' exonuclease activity.

Example 4: Testing of Example Probes

Two double-stranded test probes and an rProbe comprising a cleavable moiety were evaluated against a target nucleic acid molecule. The two double-stranded probes included a "Fluorescent Strand" hybridized with one of two quench strands, "Quench Strand 1" or "Quench Strand 2" as depicted in FIG. 8A. As shown in FIG. 8A, the Fluorescent strand included, from 5' to 3', a nucleic acid sequence and a detectable moiety 801 (e.g., FAM fluorescent dye)). Quench Strand 1, included, from 5' to 3', a quencher 803 (e.g., IABkFQ quencher) and a sequence complementary to the sequence of the Fluorescent strand. Quench Strand 2 was structurally the same as Quench Strand 2, except that it also included a terminator (e.g., dideoxycytosine (ddC)) nucleotide 804 at its 3' end. When provided to a reaction mixture as single strands, the two component strands of each of the double-stranded test probes hybridized together to form their respective double-stranded test probe.

The strands of each of the double-stranded test probes or the rProbe were provided to a 20 µL reaction mixture and each of the three test probes evaluated in an amplification reaction of a target nucleic acid molecule. The reaction mixture included about 1000 copies of the target nucleic acid molecule; 0.4 µM of forward primer (5'-TCC CAA ATC TCC AGT CAC TCdUdU-3' (SEQ ID NO: 3)) and 0.4 µM of reverse primer (5'-CAA CAT ACC TTG ATA GTC CAGdUdU-3' (SEQ ID NO: 4)); 0.15 µM of Fluorescent strand and Quench Strand 1 or Quench Strand 2, or 0.1 µM of rProbe; and 1× Phusion Master Mix (Thermo). The amplification reactions were carried out in a real-time thermocycler, where the reaction mixtures were preheated at 98° C. for 20 s, followed by 45 cycles of a temperature cycling program that included cycles of 96° C. for 10 s, 60° C. for 35 s and 72° C. for 15 s. Signal in the reaction mixture was monitored during the 60° C. stage of each cycle of the temperature cycling program.

Figure 8B:
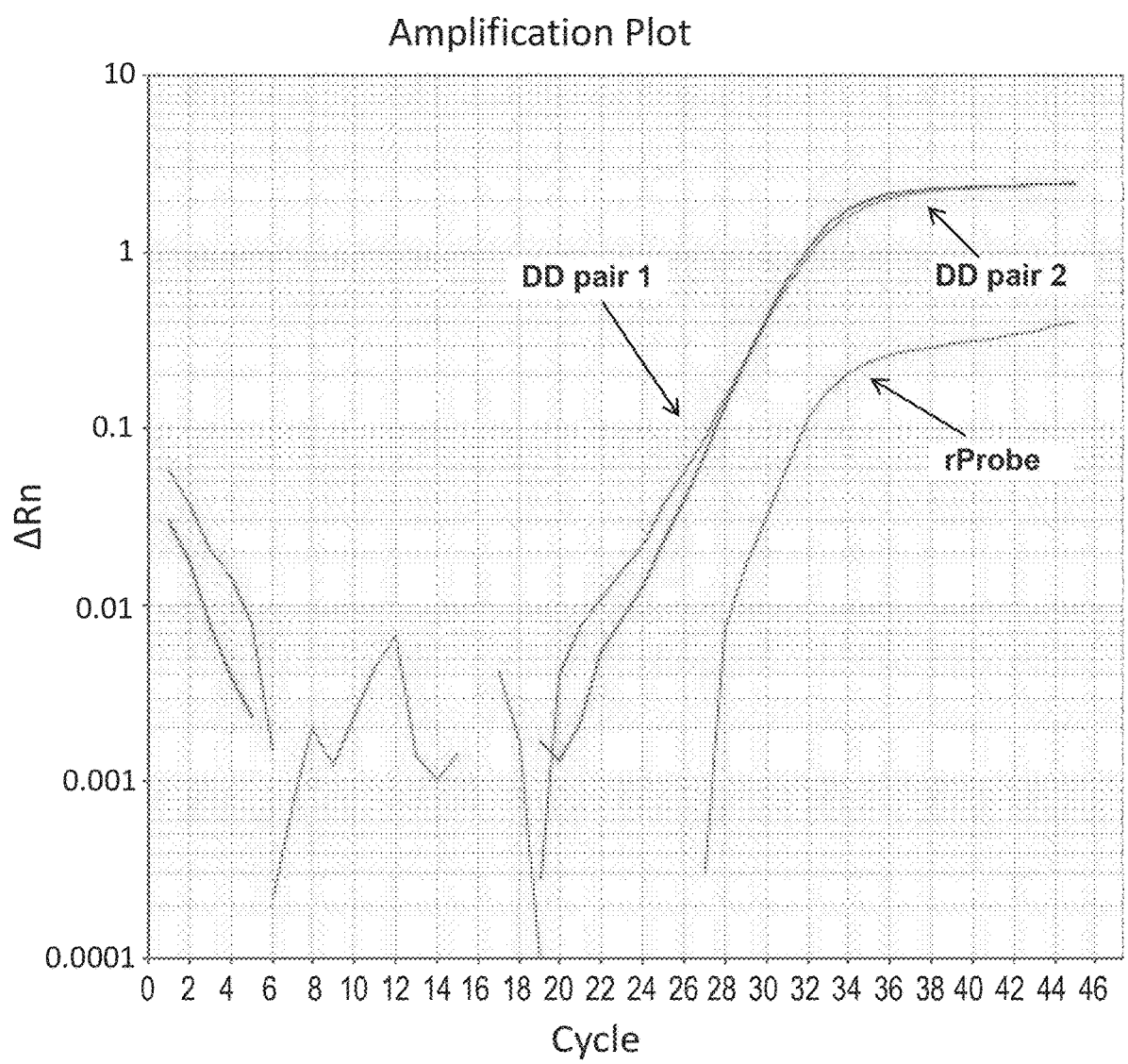
FIG. 8B graphically summarizes the results of various experiments described in Example 4.

The results of the experiments are shown in FIG. 8B. The double-stranded test probe comprising the Fluorescent Strand and Quench Strand 1 is indicated with "DD Pair 1" and the double-stranded test probe comprising the Fluorescent Strand and Quench Strand 2 is indicated with "DD Pair 2" in FIG. 8B. The rProbe test probe is indicated as "rProbe" in FIG. 8B. FIG. 8B depicts an amplification plot showing change in signal (ΔRn) vs cycle number at log scale. As shown in FIG. 8B, the two double-stranded test probes exhibited similar performance and were quantitative. Moreover, rProbe also appeared to function quantitatively in the absence of 5' exonuclease activity. Thus, the results shown in FIG. 8B suggest that a double-stranded probe can be used quantitatively to detect amplification products in the absence of 5' exonuclease activity.

Example 5: Detecting Single Nucleotide Polymorphisms (SNPs)

A target nucleic acid molecule comprising a SNP site was investigated and is shown in FIG. 14A. A nucleotide site of the SNP site is indicated by the "N" nucleotide in the box shown in FIG. 14A. As shown in FIG. 14C, a forward primer ("A-forward") comprising, at its 3'end, the sequence "IUU" was used to detect an "A/T" SNP at the SNP site N. The inosine nucleotide is a purine derivative that can be used to detect a purine base in the SNP site. The corresponding reverse primer ("A-reverse") used to detect an A/T SNP at the SNP site and comprising, at its 3' end, the sequence "UU" is also shown in FIG. 14C.

Moreover, as shown in FIG. 14C, a reverse primer ("G-reverse") comprising, at its 3' end, the sequence "UUU" was used to detect an "C/G" SNP at the SNP site N. The most 5' of the 3 U nucleotides is a pyrimidine derivative that can be used to detect a pyrimidine base in the SNP site. The corresponding forward primer ("G-forward") used to detect an C/G SNP at the SNP site and comprising, at its 3' end, the sequence "UU" is also shown in FIG. 14C.

Each primer set (A-forward/A-reverse or G-forward/G-reverse) was evaluated in discriminating its target SNP (A/T vs. C/G) in a series of six reaction mixtures (A-F). Two of the six reaction mixtures included either 100 or 1000 copies of the target nucleic acid molecule in FIG. 14A with the target SNP for the primer set tested in the SNP site (e.g., "A" replaced for N in the SNP site for the A-forward/A-reverse primer set, "G" replaced for N in the SNP site for the G-forward/G-reverse primer set). The other four reaction mixtures for each set included 1000, 10000, 100000 or 1000000 copies of the target nucleic acid molecule in FIG. 14A with the non-target SNP for the primer set tested in the SNP site (e.g., "G" replaced for N in the SNP site for the A-forward/A-reverse primer set, "A" replaced for N in the SNP site for the G-forward/G-reverse primer set).

Each reaction mixture had a total volume of 20 µL. Each reaction mixture included the appropriate number of copies of the appropriate target nucleic acid molecule (A in the SNP site or G in the SNP site), the respective forward and reverse primers at 0.25 µM, 200 µM dNTPs, 0.02 units/µL Phusion DNA polymerase and buffer from New England Biolabs, and SYBR Green (at a concentration of 0.3×) and ROX (at a concentration of 1×) fluorescent dyes obtained from Life Technologies. To complete amplification of the target nucleic acid molecules, each reaction mixture was subject to a thermal cycling program that included an initial denaturation step at 98° C. for 10 s, followed by 45 cycles of 98° C. for 1 s, 60° C. for 30 s and 72° C. for 10 s.

Figure 14D:
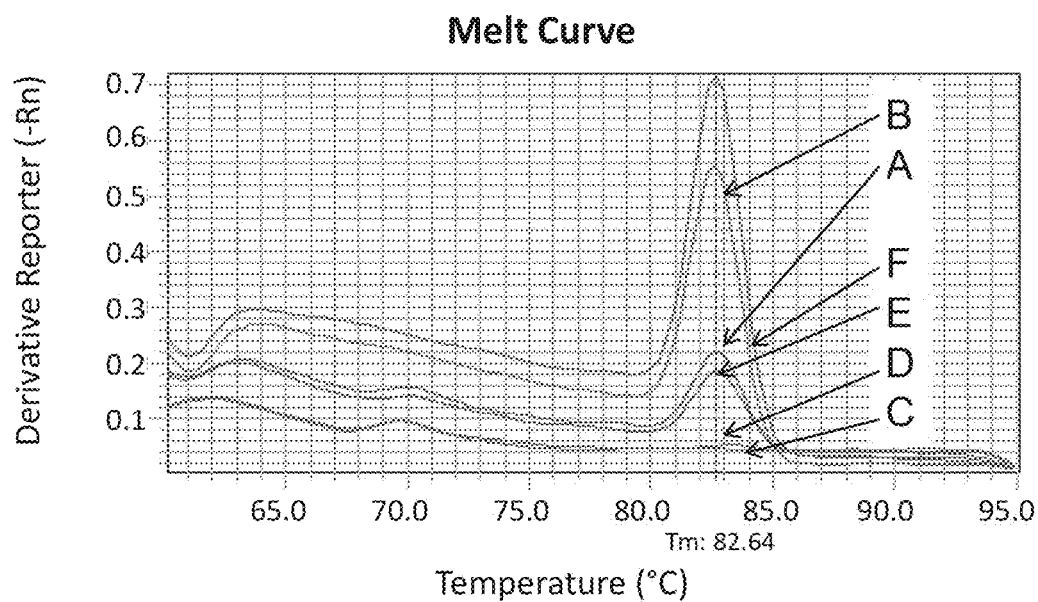
FIGS. 14D and 14E provide graphic depictions of example melting curve analyses of various reaction mixtures and tables summarizing the contents of the various reaction mixtures as described in Example 5.
Figure 14E:
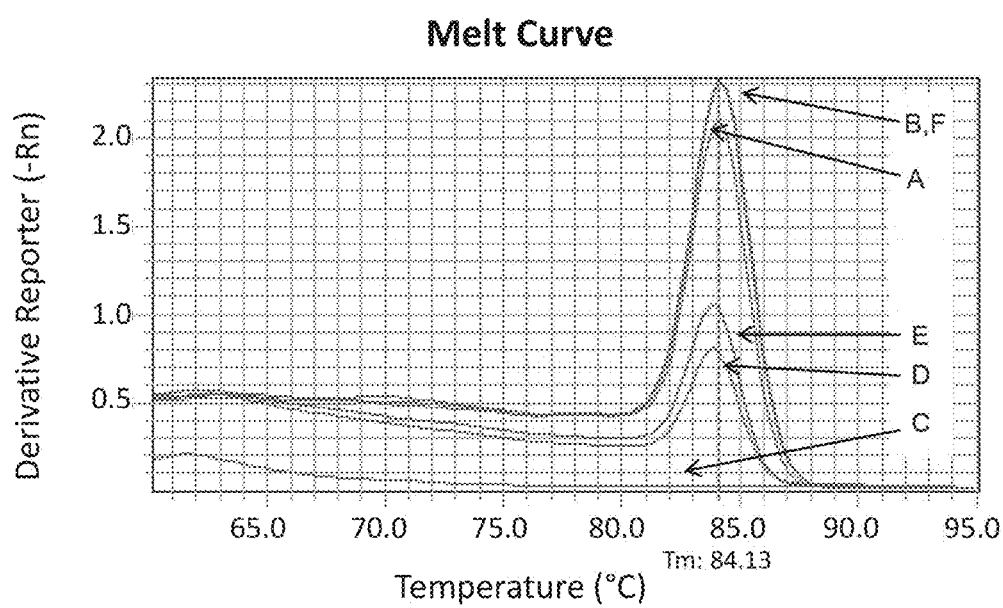

After the thermal cycling program was completed, a melting curve analysis for each reaction mixture was completed. Plots depicting the results of the melting curve analyses for each set of reaction mixtures are shown in FIG. 14D (for reaction mixtures evaluating A-forward/A-reverse) and FIG. 14E (for reaction mixtures evaluating G-forward/G-reverse). In each of FIG. 14D and FIG. 14E, a table is shown indicating which target nucleotide was in the SNP site of the target nucleic acid molecule and the copy number of the appropriate target nucleic acid molecule in each reaction mixture (A-F). In FIG. 14D and FIG. 14E, the melting curve analysis for each reaction mixture is shown in the plots with letter for each labeled curve corresponding to the appropriate reaction mixture in the table.

As shown in FIG. 14D, similar changes in fluorescence were observed during melting curve analysis for target nucleic acid molecules comprising an A in the SNP site at substantially lower copy numbers of the target nucleic acid molecule when the forward-A and reverse-A primers were used for amplification. For example, a similar change in fluorescence was observed for the reaction mixture (A) comprising 100 copies of the target nucleic acid molecule with A in the SNP site as was observed for the reaction mixture (E) comprising 100000 copies of the target nucleic acid molecule with G in the SNP site. In addition, a similar change in fluorescence was observed for the reaction mixture (B) comprising 1000 copies of the target nucleic acid molecule with A in the SNP site as was observed for the reaction mixture (F) comprising 1000000 copies of the target nucleic acid molecule with G in the SNP site. In both comparisons, about 1000 fold discrimination in detecting the target SNP was observed based on the copy numbers of each target nucleic acid molecule in the two reaction mixtures.

Similarly, as shown in FIG. 14E, similar changes in fluorescence were observed during melting curve analysis for target nucleic acid molecules comprising an G in the SNP site at substantially lower copy numbers of the target nucleic acid molecule when the forward-G and reverse-G primers were used for amplification. For example, a higher change in fluorescence was observed for the reaction mixture (A) comprising 100 copies of the target nucleic acid molecule with G in the SNP site as was observed for the reaction mixture (E) comprising 100000 copies of the target nucleic acid molecule with A in the SNP site. In addition, a similar change in fluorescence was observed for the reaction mixture (B) comprising 1000 copies of the target nucleic acid molecule with G in the SNP site as was observed for the reaction mixture (F) comprising 1000000 copies of the target nucleic acid molecule with A in the SNP site. In both comparisons, at least 1000 fold discrimination in detecting the target SNP was observed based on the copy numbers of each target nucleic acid molecule in the two reaction mixtures.

Figure 11A:
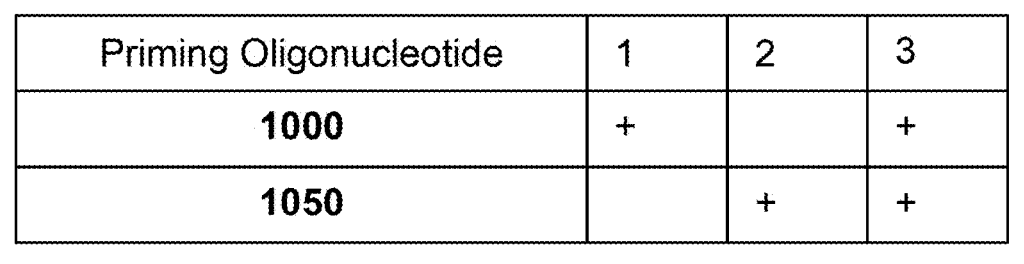

Example 6: Nested Amplification Reaction with Activatable and Inactivatable Priming Oligonucleotides The inactivatable priming oligonucleotide 1000, activatable priming oligonucleotide 1050 and reverse primer 1060 as described elsewhere herein and depicted in FIG. 10A-C were used to amplify a target nucleic acid molecule in a series of three sets of reaction mixtures. Each set of reaction mixtures was subject to a particular processing program (A, B or C) and included a reaction mixture comprising reverse primer 1060 and inactivatable priming oligonucleotide 1000; a reaction mixture comprising reverse primer 1060 and activatable priming oligonucleotide 1050; and a reaction mixture comprising reverse primer 1060, inactivatable priming oligonucleotide 1000 and activatable priming oligonucleotide 1050. Thus, a total of nine reaction mixtures (3 sets×3 reaction mixtures each) were evaluated. A summary for each reaction mixture in a set of reaction mixtures is shown in the table in FIG. 11A.

Each reaction mixture had a total volume of 20 µL containing 1× Phusion flash PCR reagent (made from 2× master mix from New England Biolabs), about 100 picograms ("pg") of human DNA as background, about 1000 copies of the target nucleic acid molecule. Where a reaction mixture included inactivatable priming oligonucleotide 1000, the inactivatable priming oligonucleotide 1000 was included at a concentration of 0.1 µM. Where a reaction mixture included activatable priming oligonucleotide 1050, activatable priming oligonucleotide 1050 was included at a concentration of 0.5 µM. Reverse primer 1060 was included in reaction mixtures at a concentration of 0.5 µM. Where a reaction mixture included RNase HII or where RNase HII was added, RNase was present at a concentration of 0.125 units/µL.

Figure 11B:
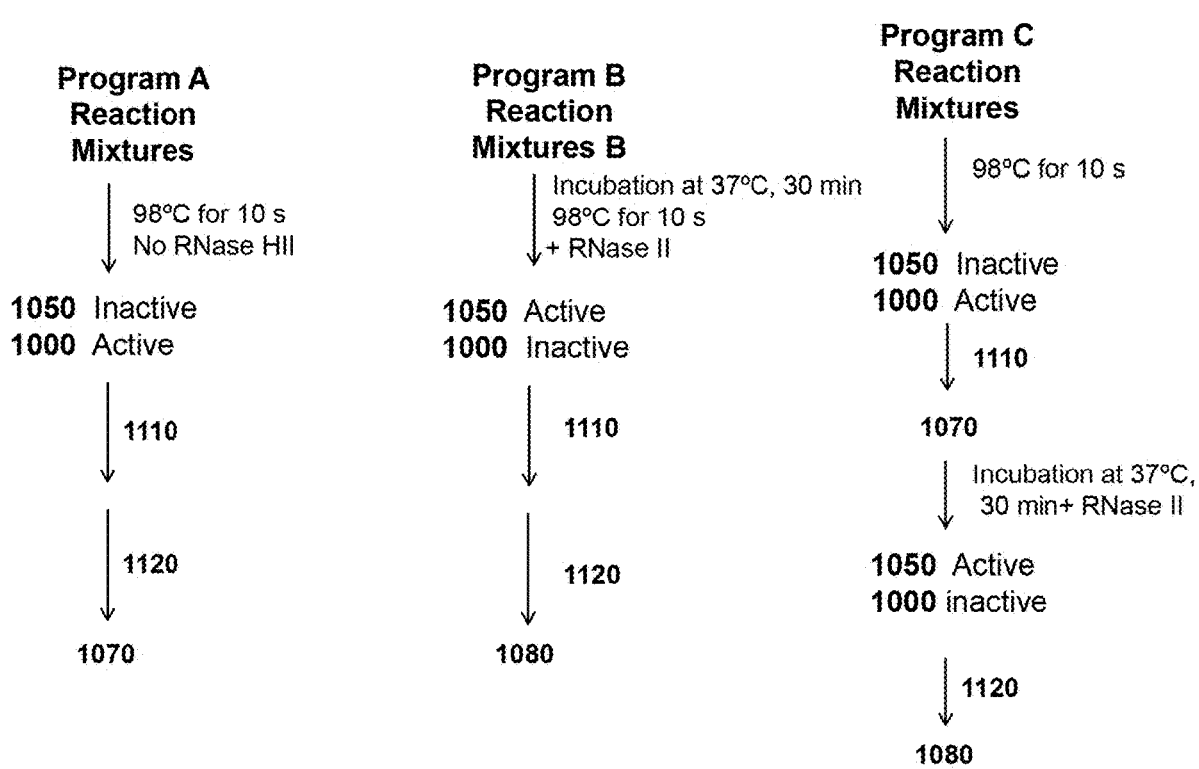
FIG. 11B schematically depicts example processing programs as described experiments described in Example 6.

Each set of three reaction mixtures was subject to a particular processing program A, B or C. A summary of processing programs A, B and C is graphically depicted in FIG. 11B. As shown in FIG. 11B, program A reaction mixtures were provided at an initial temperature of 98° C. (for 10 s) and without RNase HII. At such reaction conditions, inactivatable priming oligonucleotide 1000 is active and can participate in an amplification reaction to amplify the target nucleic acid molecule. Moreover, at such conditions, activatable priming oligonucleotide 1050 is not active and cannot participate in an amplification reaction to amplify the target nucleic acid molecule. The reaction mixtures were then subject to two series of amplification cycles 1110 and 1120. Series 1110 included 15 cycles of 98° C. for 1 s, 60° C. for 5 s and 72° C. for 10 seconds. Series 1120 included 30 cycles of 98° C. for 1 s, 60° C. for 5 s and 72° C. for 10 seconds. As inactivatable priming oligonucleotide 1000 was active and activatable priming oligonucleotide 1050 was inactive, amplification products similar to those of amplification product 1070 (e.g., approximately 100 bp) in FIG. 10C were expected in reaction mixtures including inactivatable priming oligonucleotide 1000.

As shown in FIG. 11B, program B reaction mixtures were provided with RNase HII and incubated at 37° C. for 30 min. At such reaction conditions, inactivatable priming oligonucleotide 1000 is inactivated and cannot participate in an amplification reaction to amplify the target nucleic acid molecule. Moreover, at such conditions, activatable priming oligonucleotide 1050 is activated and its nucleic acid sequence 1050A' can participate in an amplification reaction to amplify the target nucleic acid molecule. The reaction mixtures were then subject to series 1110 and 1120 amplification cycles. As inactivatable priming oligonucleotide 1000 was inactive and activatable priming oligonucleotide 1050 was active, amplification products similar to those of amplification product 1080 (e.g., approximately 70 bp) in FIG. 10C were expected in reaction mixtures including activatable priming oligonucleotide 1050.

As shown in FIG. 11B, program C reaction mixtures were provided at an initial temperature of 98° C. (for 10 s) and subject and conditions modulated such that amplification of the target nucleic acid molecule was achieved via both inactivatable priming oligonucleotide 1000 and activatable priming oligonucleotide 1050. At the initial condition, inactivatable priming oligonucleotide 1000 is active and activatable priming oligonucleotide 1050 is not active as described above. For the reaction mixtures RNase HII was added initially. In reaction mixture 1 (having inactivatable priming oligonucleotide 1000 only), RNase was active initially and, thus, the inactivatable priming oligonucleotide was inactive and amplification was not expected to proceed. The reaction mixtures were then subject to series 1110 amplification cycles to generate amplified products 1070. The reaction mixtures were then incubated at 37° C. for 30 minutes and RNase HII activated (or alternatively, added to the reaction mixture) to activate activatable priming oligonucleotide 1050 and inactivate inactivatable priming oligonucleotide 1000. The reaction mixtures were then subject to series 1120 amplification cycles in order to generate amplification products. As priming oligonucleotide 1050 was active in reaction mixtures 2 (including activatable priming oligonucleotide 1050 only) and 3 (including both inactivatable priming oligonucleotide 1000 and activatable priming oligonucleotide 1050), amplification products similar to those of amplification products 1080 in FIG. 10C were expected. As inactivatable priming oligonucleotide 1000 was inactive in reaction mixture 1 (having inactivatable priming oligonucleotide 1000 only), no amplification products were expected.

Figure 11C:
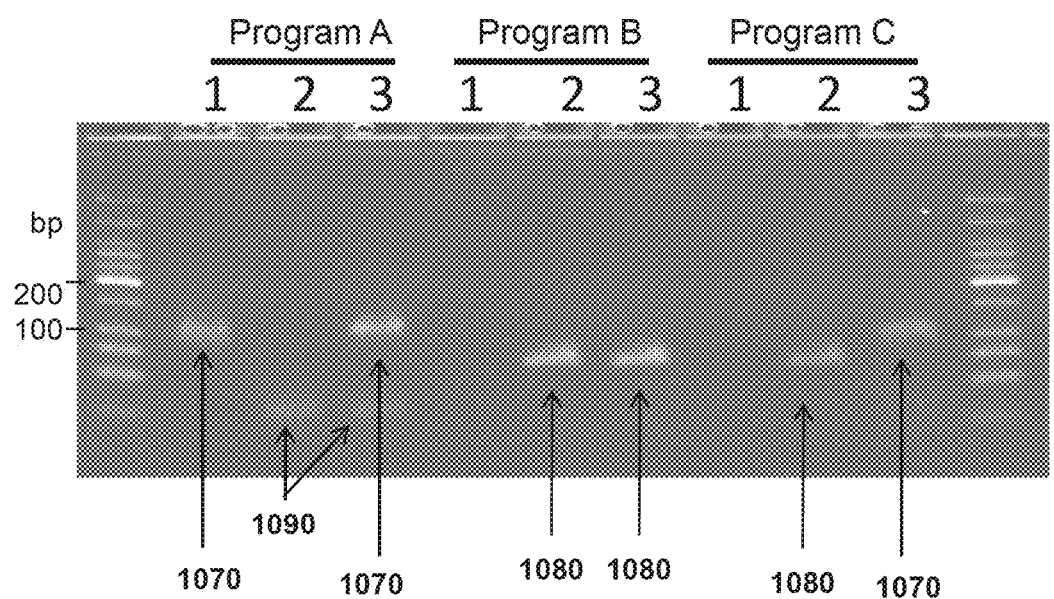
FIG. 11C is a photograph of a gel electrophoresis analysis as described in Example 6.

After amplification reactions were completed, 10 μL of each reaction mixture was analyzed by 4% agarose gel electrophoresis in the presence of Ethidium Bromide. As noted above, the expected product size of amplification products 1070 was approximately 100 bp and the expected product size of amplification products 1080 was approximately 75 bp. The results of the gel electrophoresis analysis are shown in FIG. 11C. As shown in FIG. 11C, amplification products 1070 at approximately 100 bp were observed in program A reaction mixtures where inactivatable priming oligonucleotide 1000 was present (e.g., reaction mixtures 1 and 3). Where inactivatable priming oligonucleotide 1000 was not present (e.g., reaction mixture 2), amplification products 1070 at 100 bp were not observed. In some of the reaction mixtures, shorter products 1090 were observed and may have been primer-dimer by-products.

As shown in FIG. 11C, amplification products 1080 at approximately 75 bp were observed in program B reaction mixtures where activatable priming oligonucleotide 1050 was present (e.g., reaction mixtures 2 and 3). Where activatable priming oligonucleotide 1050 was not present (e.g., reaction mixture 1), amplification products 1080 at 75 bp were not observed. Moreover, as shown in FIG. 11C, amplification products 1080 at approximately 75 bp were observed in the second reaction mixture for program C reaction mixtures where activatable priming oligonucleotide 1050 was present and active in the absence of inactivatable priming oligonucleotide 1000 (e.g., reaction mixture 2). Where inactivatable priming oligonucleotide 1000 was also present and active (e.g., reaction mixture 3), amplification products 1070 at 100 bp were observed. Where inactivatable priming oligonucleotide 1000 was present in the absence of activatable priming oligonucleotide 1050 and inactivated (e.g., reaction mixture 1), no amplification products were observed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method, comprising:
   (a) providing a reaction mixture comprising:
      (i) a single-stranded target DNA molecule comprising a single nucleotide polymorphism (SNP) site and
      (ii) a probe, wherein said probe has (1) a known DNA sequence (2) at least one cleavable moiety, (3) a detectable moiety, and (4) a quencher, wherein said probe is complementary to said single-stranded target DNA molecule, and wherein said quencher quenches said detectable moiety when said probe is not hybridized to said single-stranded target DNA molecule; wherein the probe is not capable of intramolecular hybridization;
   (b) hybridizing said probe to said single-stranded target DNA molecule such that, said cleavable moiety is situated at the SNP site of said single-stranded target DNA molecule, wherein complementarity of the cleavable moiety with a nucleotide of the SNP site allows cleavage of the cleavable moiety and separation of the quencher from the detectable moiety; and
   (c) detecting a signal from said probe that is indicative of a presence of said nucleotide in said SNP site;
   wherein (b) and (c) are performed without the aid of an enzyme;
   wherein the method is configured to detect the SNP in a target DNA.

2. The method of claim 1, further comprising maintaining a pH of said reaction mixture at above 7.

3. The method of claim 1, wherein said single-stranded target DNA molecule does not contain a detectable moiety.

4. The method of claim 1, wherein said probe comprises a nucleotide sequence A and a nucleotide sequence B flanking said at least one cleavable moiety, and wherein said nucleotide sequence A and nucleotide sequence B are each complementary to a portion of said single-stranded target DNA molecule.

5. The method of claim 1, wherein said probe is immobilized on a substrate of an array.

6. The method of claim 5, wherein said probe is immobilized in a well of said array.

7. The method of claim 1, wherein said cleavable moiety is adapted to provide said signal upon an intermolecular hybridization of said probe to said single-stranded target DNA molecule.

8. The method of claim 1, wherein said at least one cleavable moiety is a ribose moiety.

9. The method of claim 1, wherein said single-stranded DNA molecule is derived from an amplified nucleic acid.

10. The method of claim 1, wherein said reaction mixture further comprises an activatable priming oligonucleotide, comprising:
    (a) a priming region having (i) a nucleic acid sequence A that is hybridizable to the single-stranded target DNA molecule and (ii) a cleavable moiety, wherein said nucleic acid sequence A has a 3' end that is adapted to be extended in a primer extension reaction to form a complement nucleic acid strand of said single-stranded target DNA molecule only upon cleavage of said cleavable moiety; and
    (b) a nucleic acid sequence B that is 3' to said priming region and exhibits sequence complementarity to said priming region.

11. The method of claim 10, wherein at least one cleavable moiety is a ribose.

12. The method of claim 10, wherein the activatable priming oligonucleotide comprises plurality of cleavable moiety.

13. The method of claim 1, wherein said reaction mixture further comprises an activatable priming oligonucleotide comprising:
    a) a priming region having (i) a nucleic acid sequence A that is hybridizable to a single-stranded target DNA molecule and (ii) at least one cleavable moiety, wherein said nucleic acid sequence A has a 3' end that is adapted to be extended in a primer extension reaction to form a complement nucleic acid strand of said single-stranded target DNA molecule only upon cleavage of said cleavable moiety; and
    b) a nucleic acid sequence B that is 3' to said priming region, wherein said priming region has a first melting temperature and said nucleic acid sequence B has a second melting temperature that is less than said first melting temperature.

* * * * *